(12) United States Patent
Kasahara et al.

(10) Patent No.: US 7,077,803 B2
(45) Date of Patent: Jul. 18, 2006

(54) LIVING TISSUE HARVESTING APPARATUS

(75) Inventors: Hideyuki Kasahara, Musashino (JP); Takahiro Kogasaka, Hino (JP); Shuhei Iizuka, Hachioji (JP); Masayuki Irie, Hachioji (JP)

(73) Assignees: Olympus Corporation (JP); Terumo Kabushiki Kaisha (JP)

( * ) Notice: Subject to any disclaimer, the term of this patent is extended or adjusted under 35 U.S.C. 154(b) by 574 days.

(21) Appl. No.: 10/329,947

(22) Filed: Dec. 24, 2002

(65) Prior Publication Data

US 2003/0130675 A1    Jul. 10, 2003

(30) Foreign Application Priority Data

Dec. 28, 2001 (JP) ............................ 2001-401940
Apr. 18, 2002 (JP) ............................ 2002-116512
Jun. 3, 2002 (JP) ............................ 2002-161572

(51) Int. Cl.
*A61B 1/00* (2006.01)

(52) U.S. Cl. ..................... 600/104; 600/106; 600/107
(58) Field of Classification Search ............... 600/104, 600/106, 107; 606/159, 157, 190
See application file for complete search history.

(56) References Cited

U.S. PATENT DOCUMENTS

| 5,913,866 A | 6/1999 | Ginn et al. |
| 5,916,233 A * | 6/1999 | Chin .......................... 606/190 |
| 5,938,680 A * | 8/1999 | Ginn .......................... 606/190 |
| 5,993,384 A | 11/1999 | Lunsford et al. |

FOREIGN PATENT DOCUMENTS

| JP | 2000-37389 | 2/2000 |
| WO | WO 97/26831 | 7/1997 |
| WO | WO 00/40160 | 7/2000 |

* cited by examiner

*Primary Examiner*—Beverly M. Flanagan
(74) *Attorney, Agent, or Firm*—Ostrolenk, Faber, Gerb & Soffen, LLP

(57) ABSTRACT

There is disclosed a living tissue harvesting apparatus according to one aspect of the present invention, comprising a sheath which can be inserted in a body through a cut skin portion, an endoscope inserted through the sheath, a cutting device which is disposed at the sheath and which can cut a living tissue, and a holder which is disposed at the sheath to hold a harvesting object tissue in the body and which includes a press discharge portion to press-discharge the harvesting object tissue in a direction detached from the cutting device, wherein the holder includes a hook portion to catch the living tissue in a position disposed opposite to the cutting device, and the cutting device and hook portion can move with respect to each other.

30 Claims, 35 Drawing Sheets

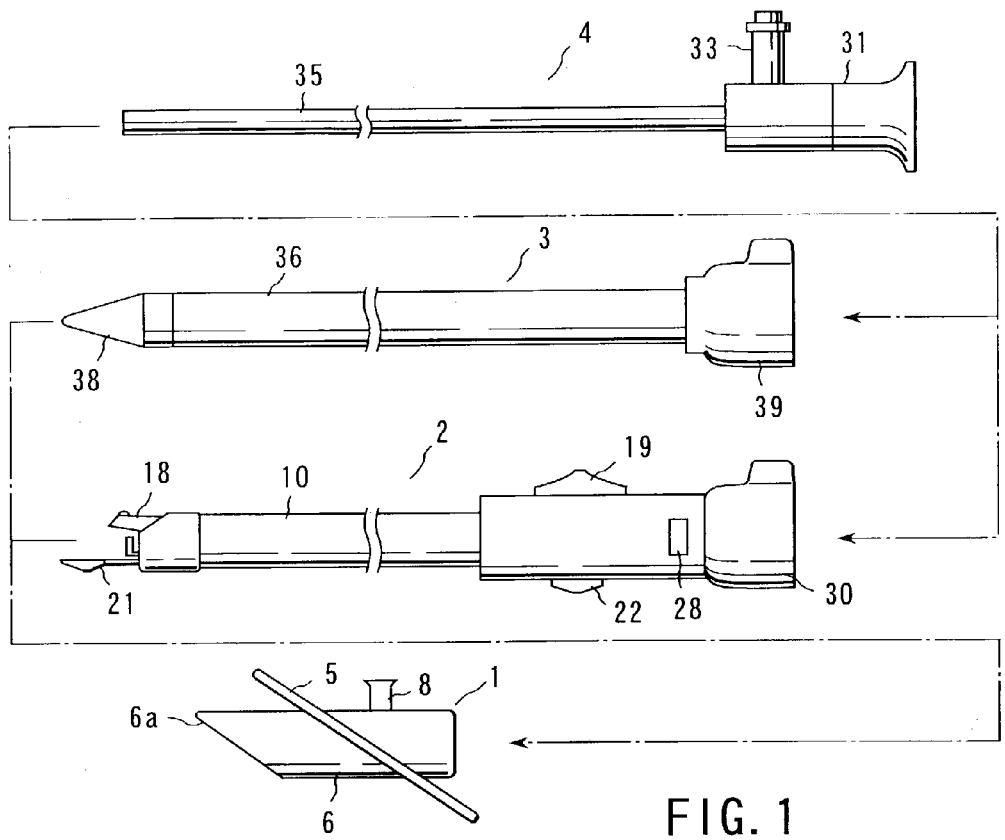
FIG. 1
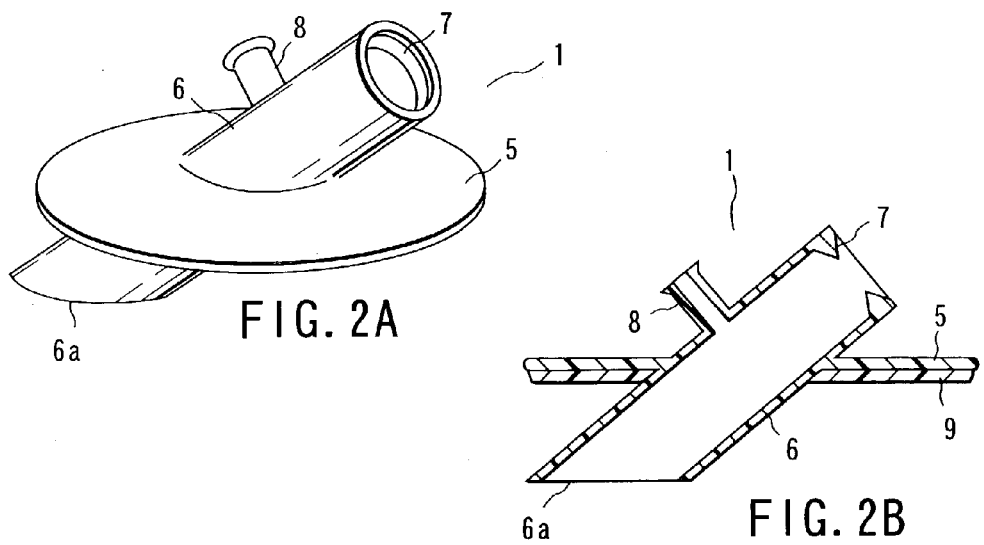
FIG. 2A
FIG. 2B

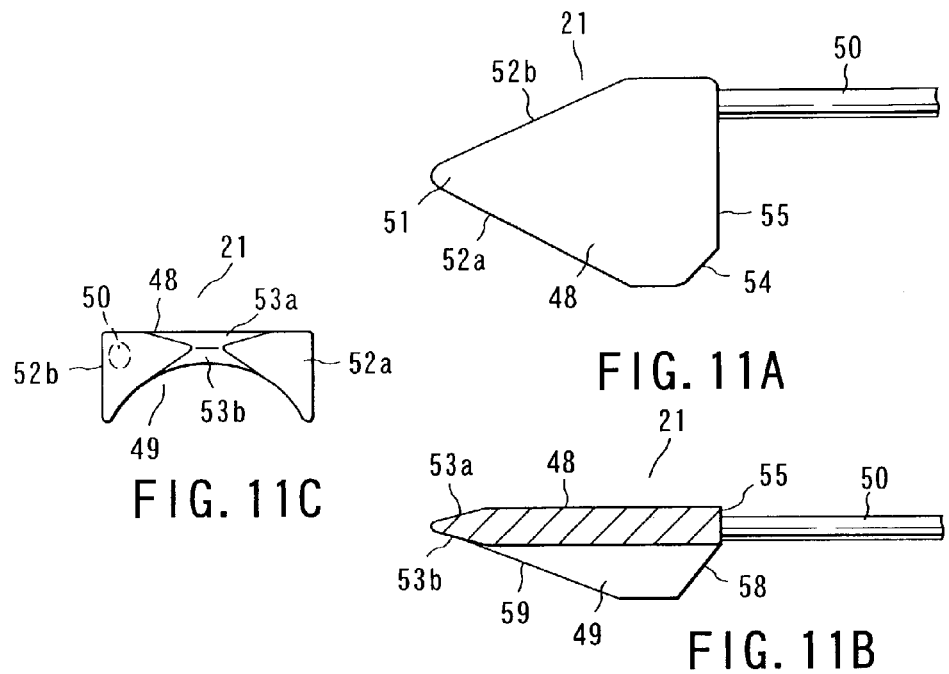
FIG. 11A
FIG. 11C
FIG. 11B
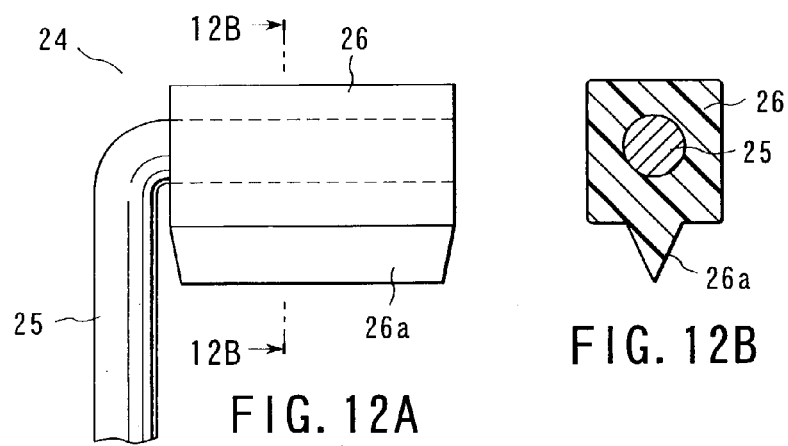
FIG. 12A
FIG. 12B
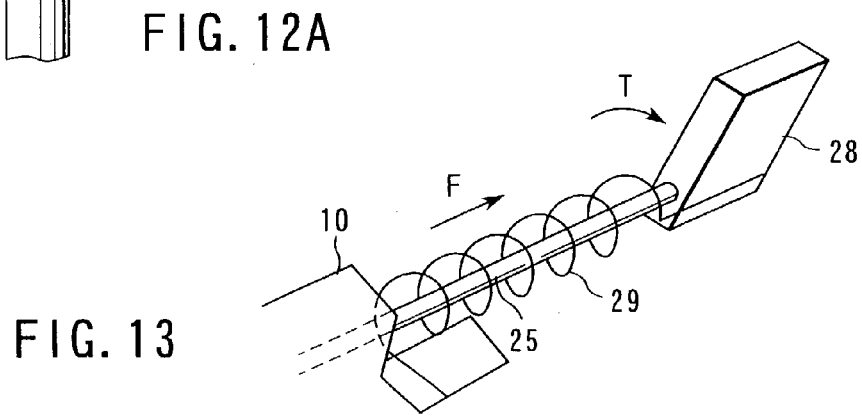
FIG. 13

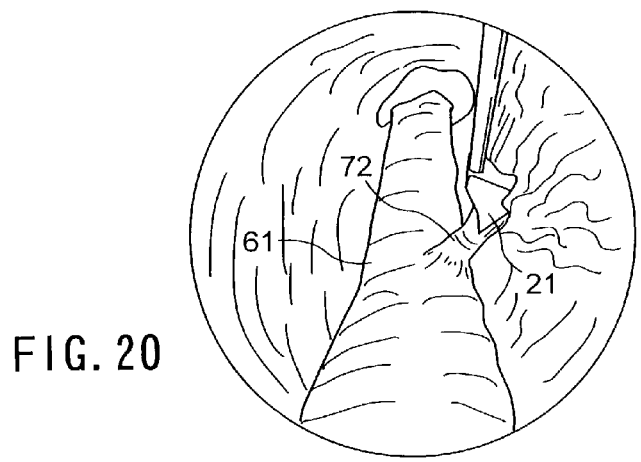
FIG. 20
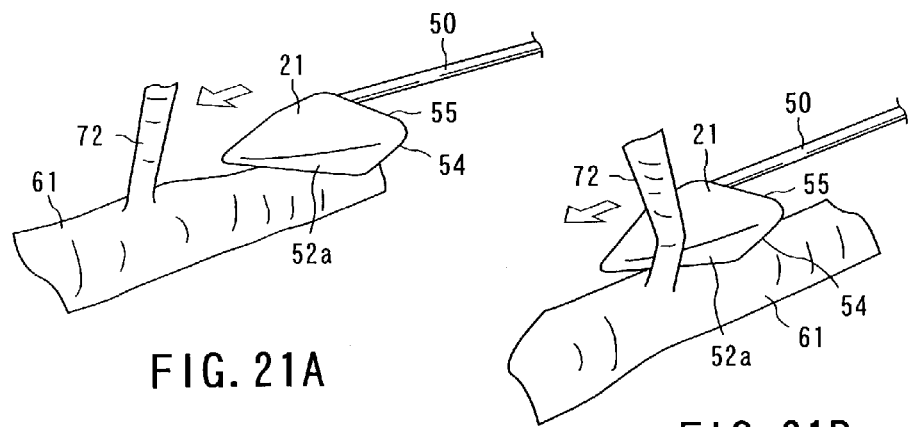
FIG. 21A
FIG. 21B
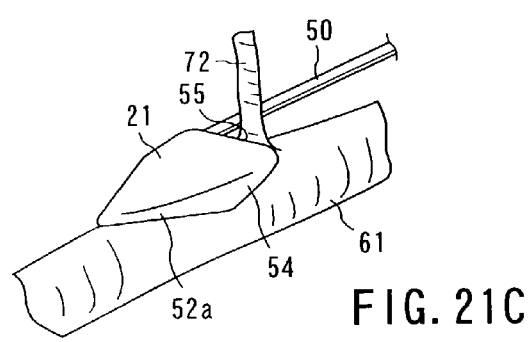
FIG. 21C

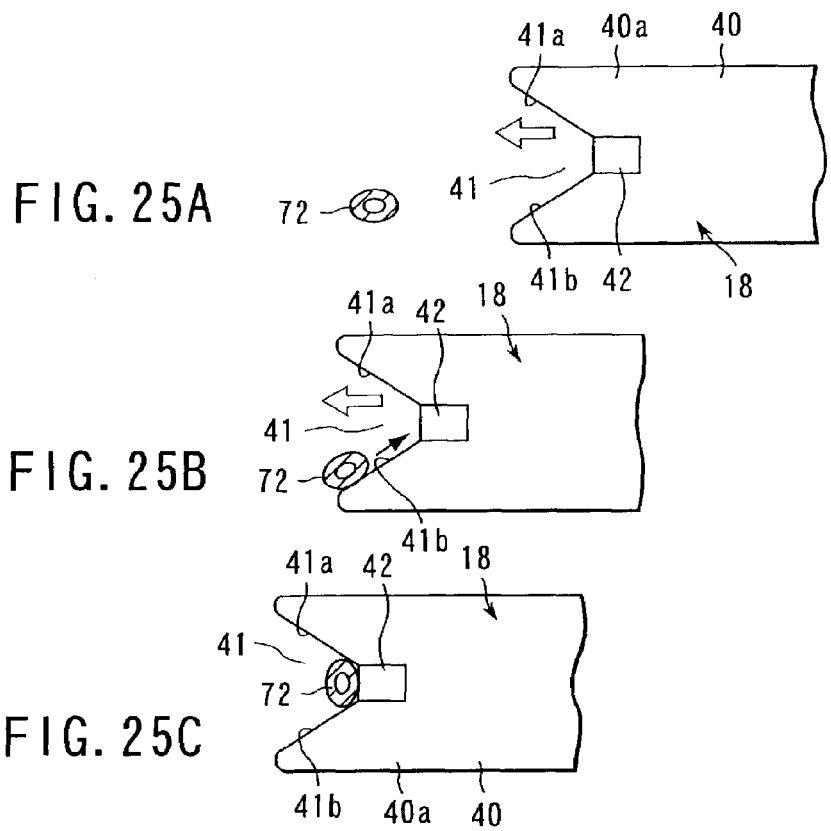
FIG. 25A
FIG. 25B
FIG. 25C
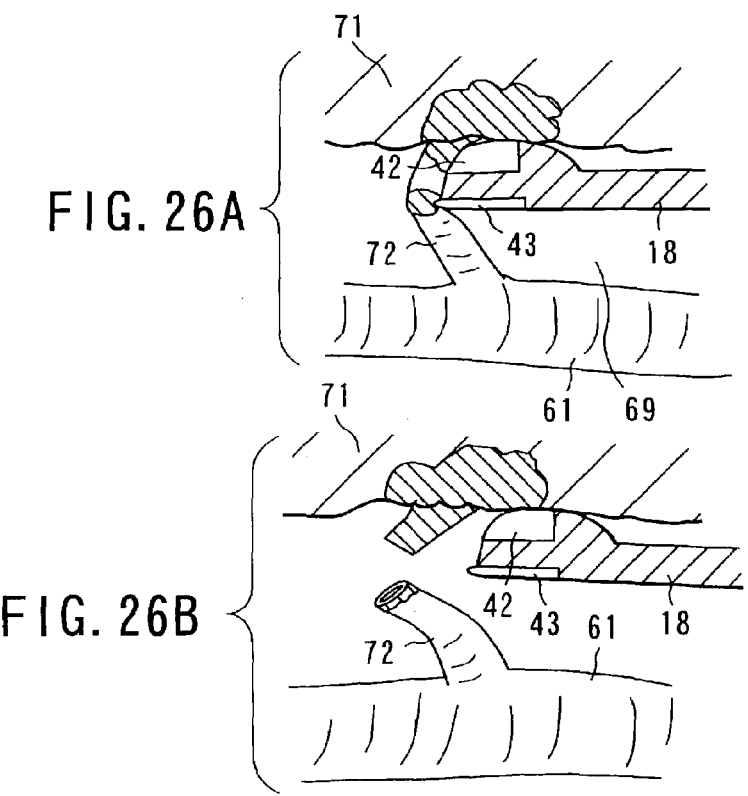
FIG. 26A
FIG. 26B

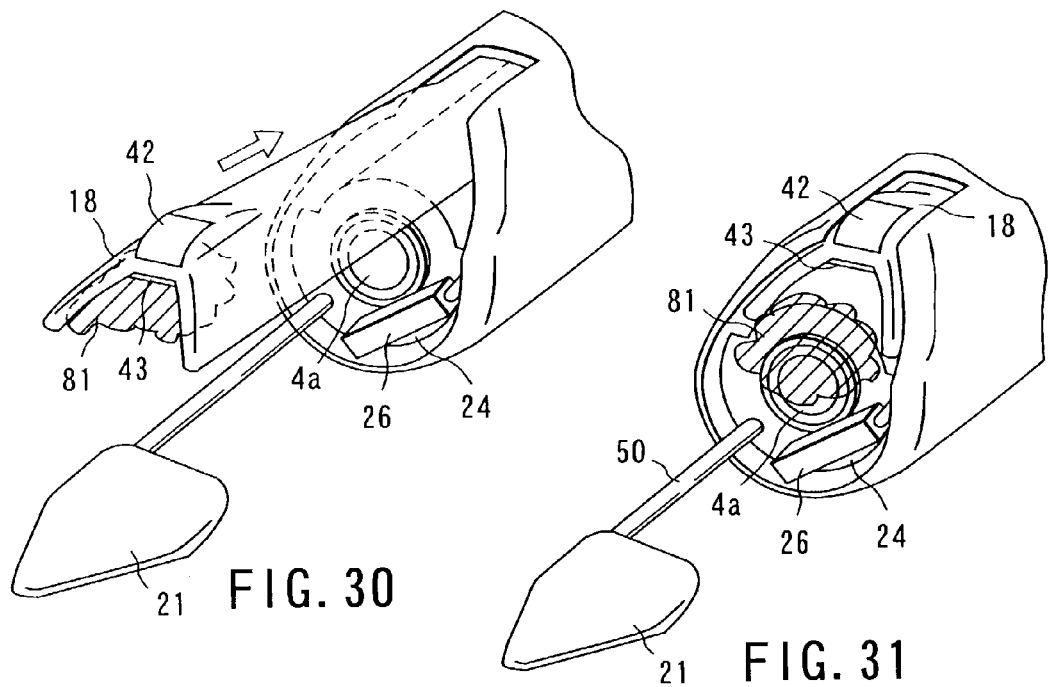
FIG. 30
FIG. 31
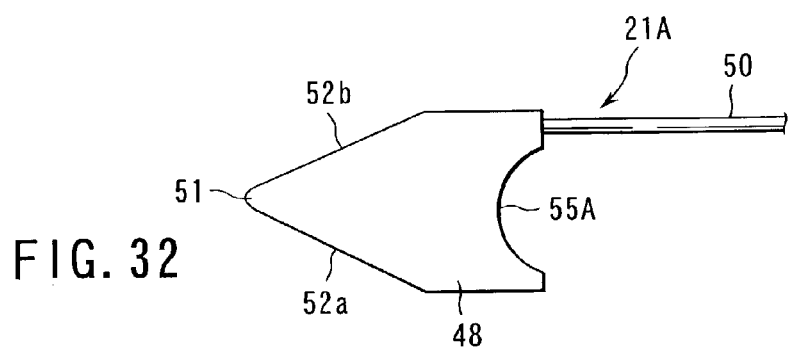
FIG. 32
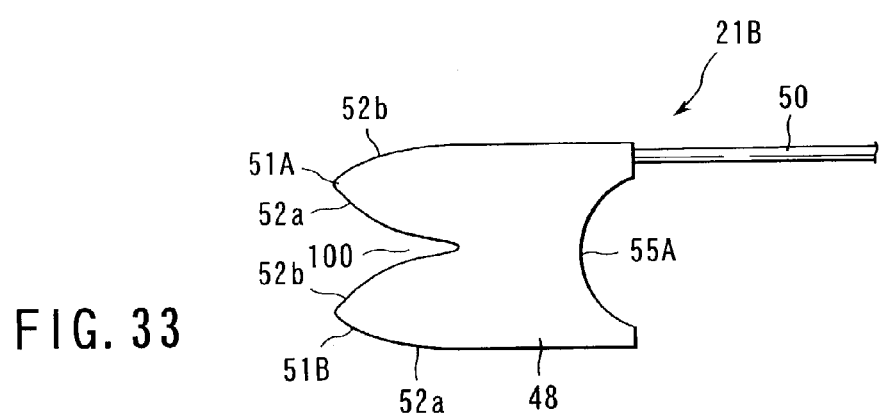
FIG. 33

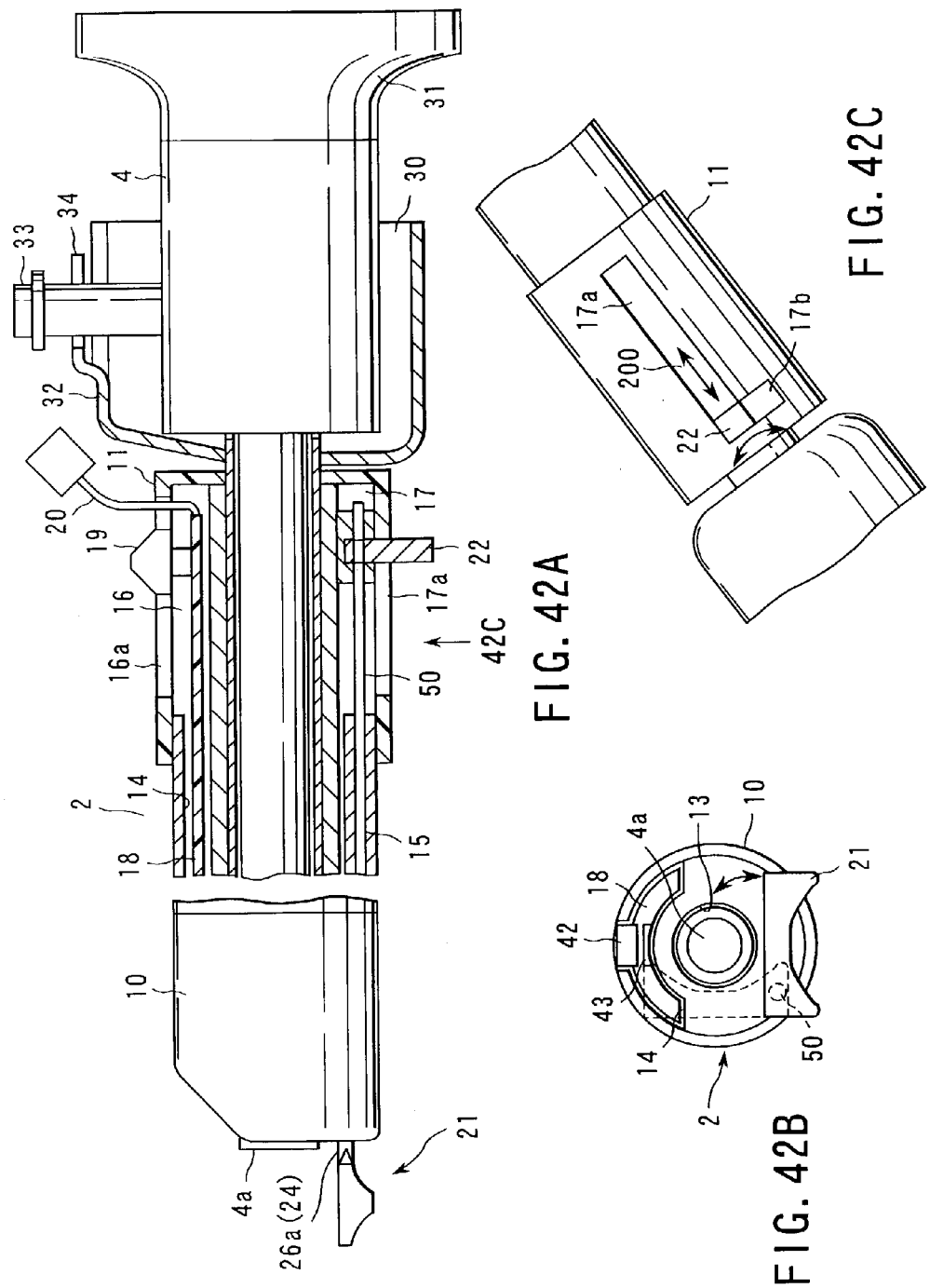

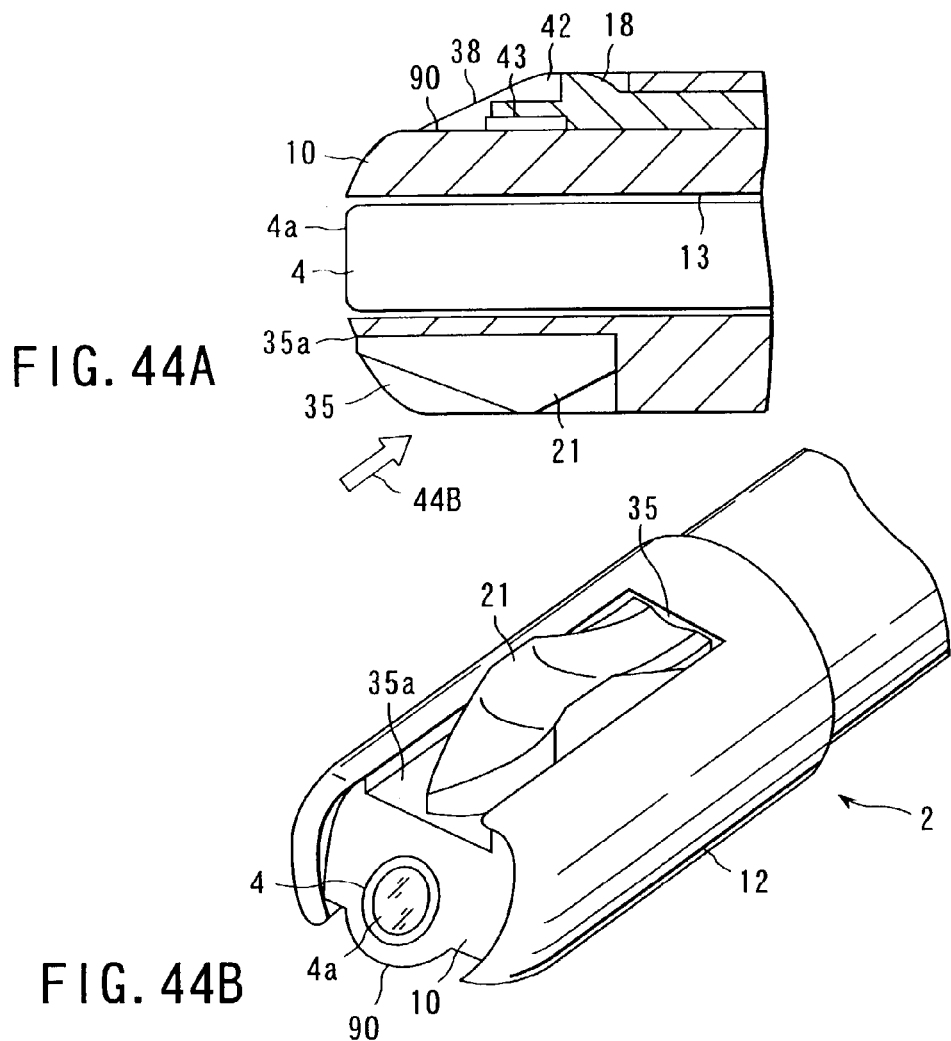
FIG. 44A
FIG. 44B
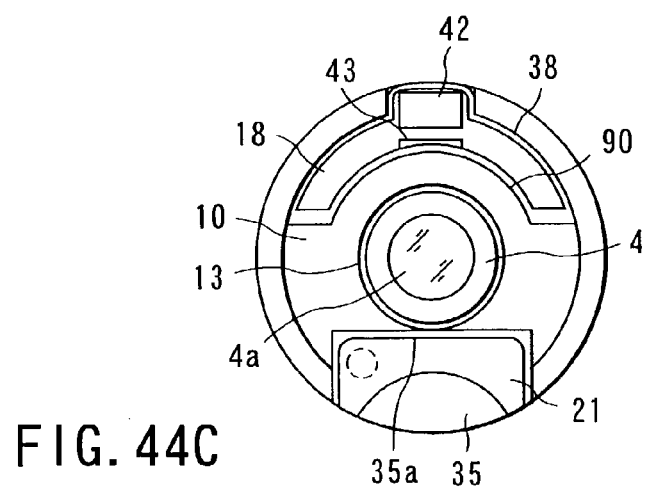
FIG. 44C

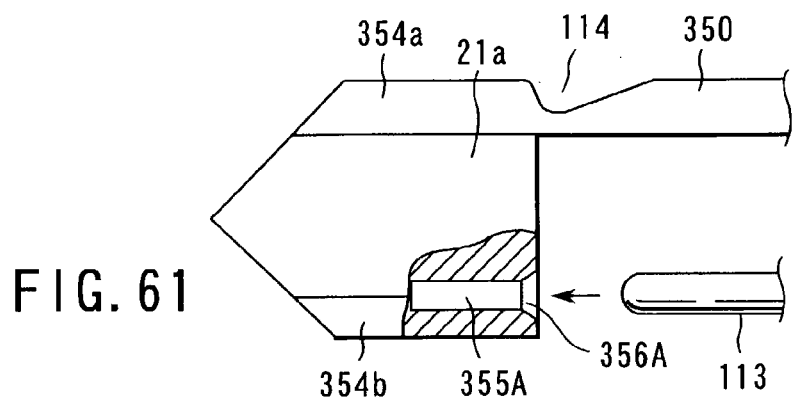
FIG. 61
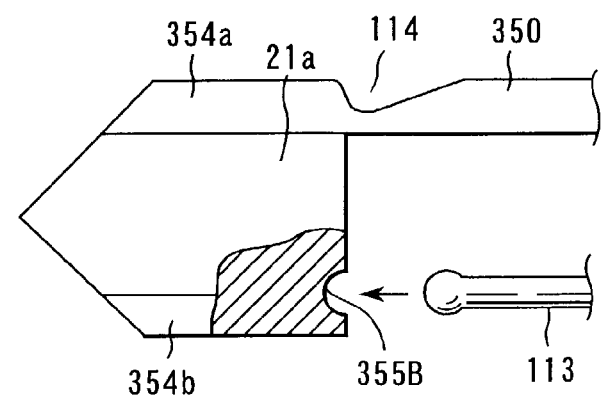
FIG. 62
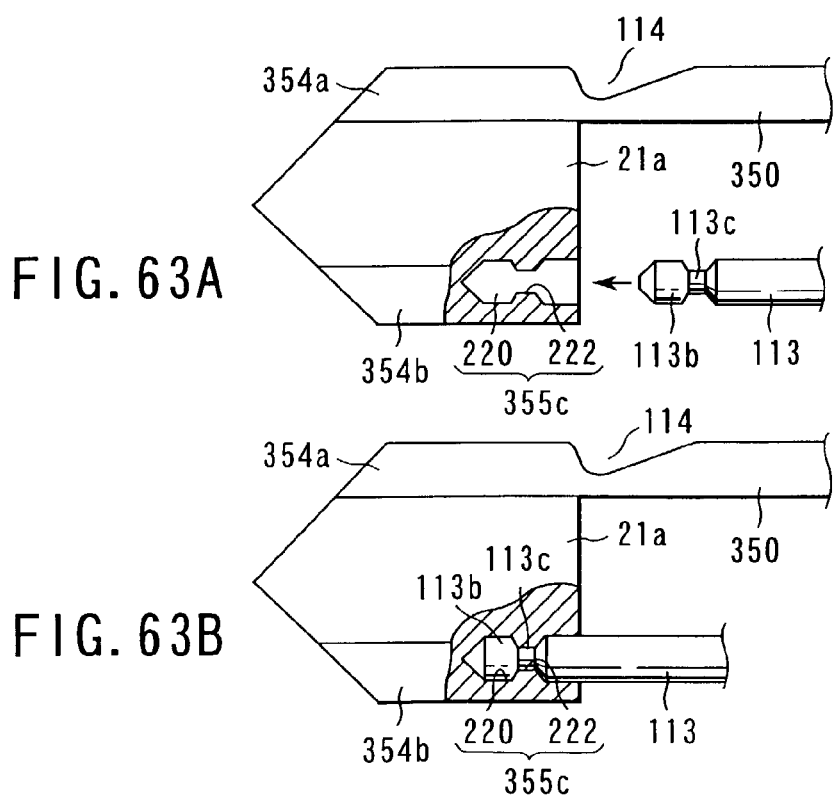
FIG. 63A
FIG. 63B

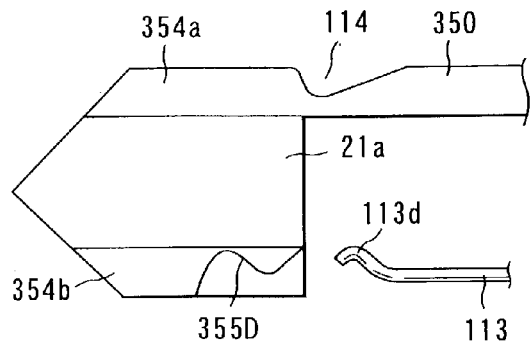
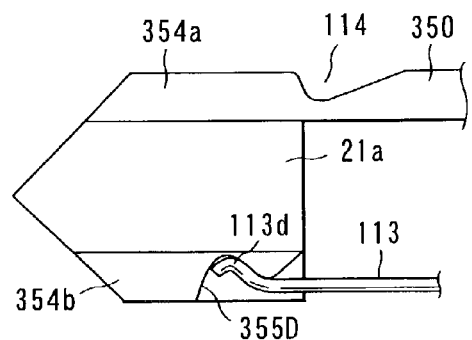
FIG. 64A          FIG. 64B
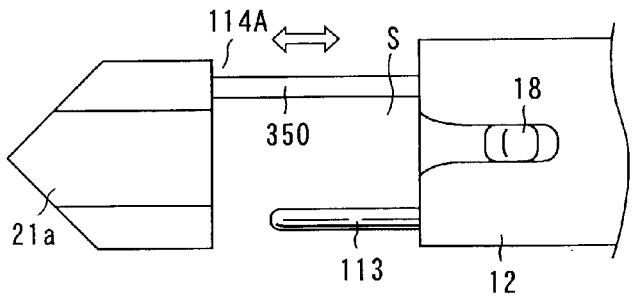
FIG. 65
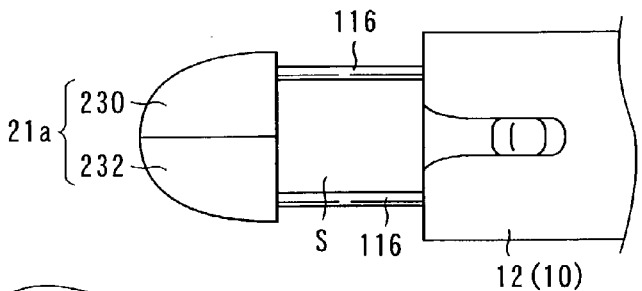
FIG. 66A
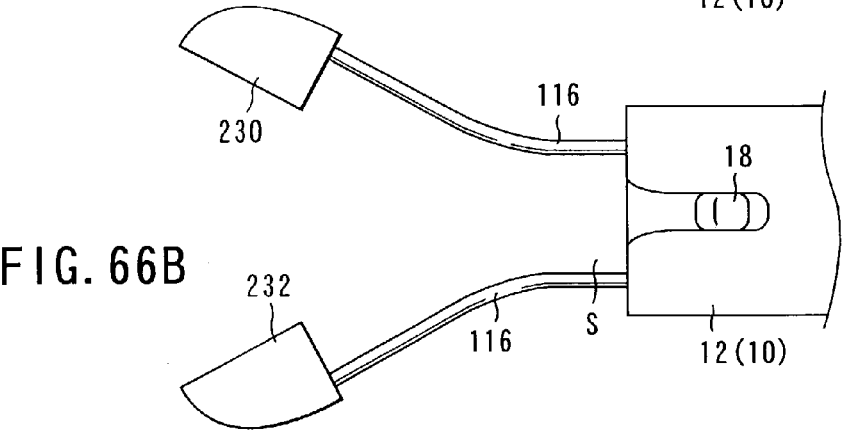
FIG. 66B

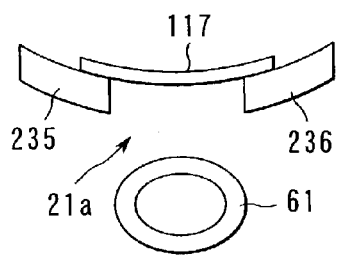
FIG. 67A
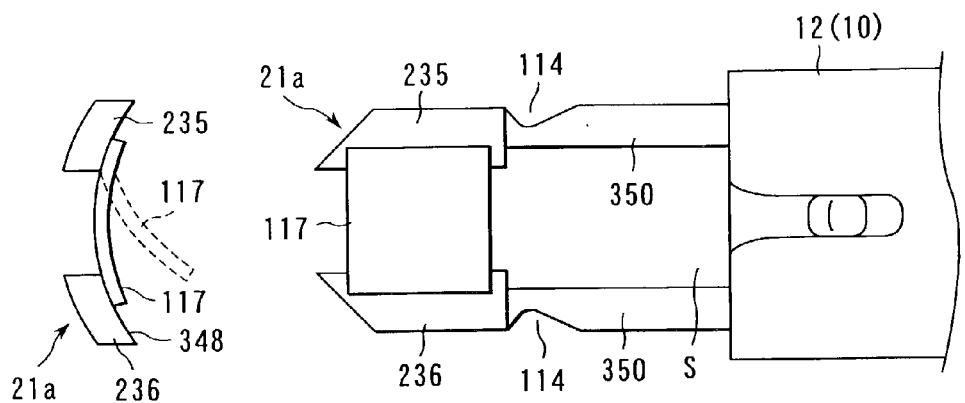
FIG. 67B
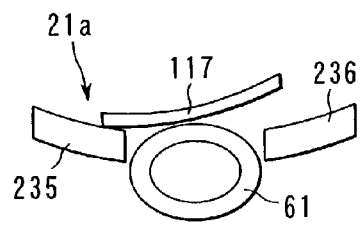
FIG. 68A
FIG. 68B
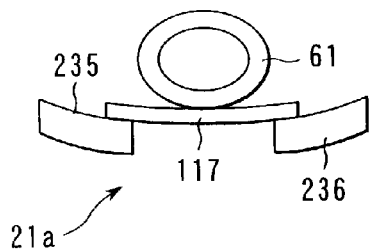
FIG. 68D
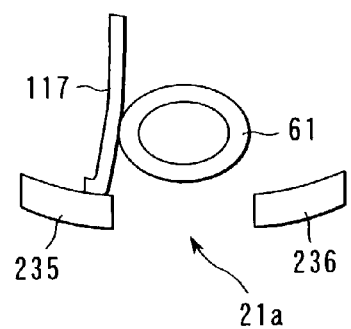
FIG. 68C

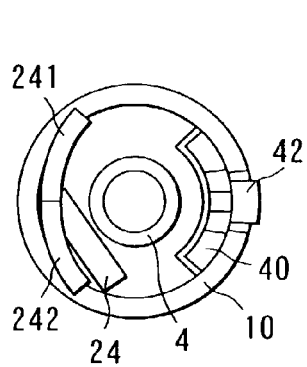
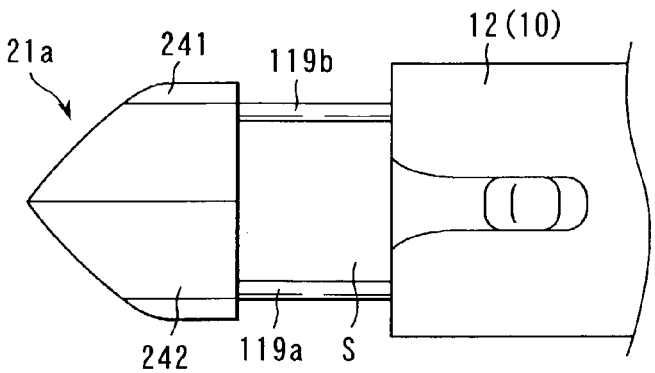
FIG. 69A          FIG. 69B
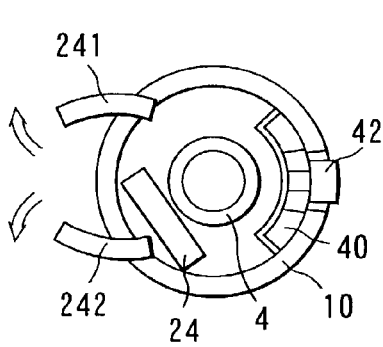
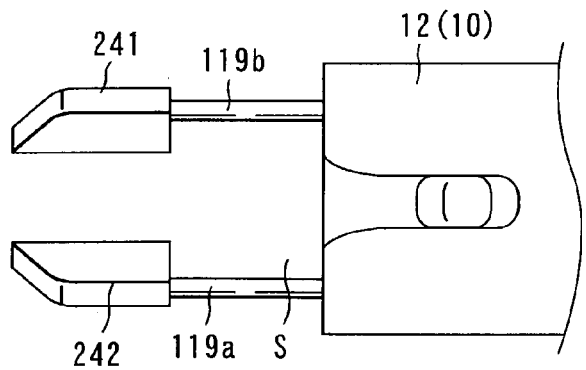
FIG. 70A          FIG. 70B
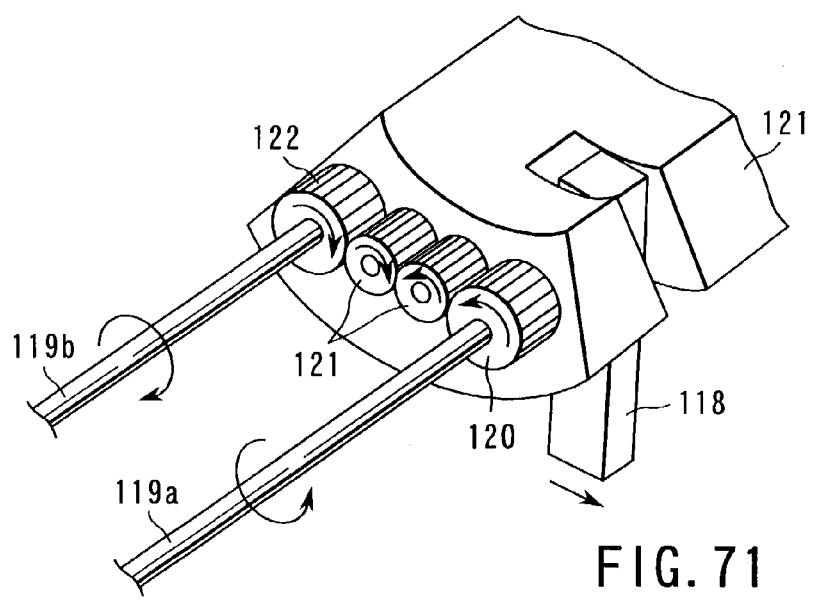
FIG. 71

LIVING TISSUE HARVESTING APPARATUS

CROSS-REFERENCE TO RELATED APPLICATIONS

This application is based upon and claims the benefit of priority from the prior Japanese Patent Applications No. 2001-401940, filed Dec. 28, 2001, No. 2002-116512, filed Apr. 18, 2002; and No. 2002-161572, filed Jun. 3, 2002, the entire contents of all of which are incorporated herein by reference.

BACKGROUND OF THE INVENTION

1. Field of the Invention

The present invention relates to a living tissue harvesting apparatus which harvests living tissues, for example, subcutaneous blood vessels such as a great saphenous vein under observation of an endoscope, particularly to an improvement of a holder assembled in this living tissue harvesting apparatus.

2. Description of the Related Art

A cannula and surgical method for use in drawing and harvesting subcutaneous blood vessels such as a great saphenous vein in an endoscopic manner are known, for example, by PCT/US99/31242 and Jpn. Pat. Appln. KOKAI Publication No. 2000-37389.

The cannula is a straight tubular member which has a device inserting path inside, and includes an operation portion in a proximal end. Through the device inserting path of the cannula, from an operation portion side, a traction portion, rigid endoscope, and incision forceps are detachably inserted. The traction portion includes a loop portion projecting from a tip end of the cannula and having an angle with respect to an axial direction of the cannula in a distal end.

When the cannula is used to harvest the subcutaneous blood vessels such as the great saphenous vein in the endoscopic manner, the following surgical method is used. That is, as shown in FIG. 73, a reference numeral 100 denotes a leg. To harvest a harvesting object blood vessel (hereinafter referred to as the blood vessel) C such as the great saphenous vein which extends over the whole length to an ankle B from an upper part of an inguinal portion A of a femoral region, a cut skin portion E1, E2, or E3 is made by a scalpel, for example, in any one portion of an upper portion of the inguinal portion A, knee D, and ankle B immediately above the blood vessel C.

Subsequently, the blood vessel C is exposed in a position of each cut skin portion E1, E3, or E3 by a dissector. Furthermore, a tissue right above the blood vessel C is exfoliated by the similar dissector with respect to a distance from each cut skin portion E1, E2, or E3, which can be observed with the naked eye.

FIG. 74 is a sectional view taken along line 74—74 of FIG. 73, reference numeral 101 denotes a scurf skin, 102 denotes a subcutaneous tissue, 103 denotes a connective tissue on the blood vessel, and the blood vessel C exists under the connective tissue on the blood vessel 103. First, a cannula including a conical chip on the tip end of the cannula is used as the dissector to strip the blood vessel C and peripheral tissue and to form a cavity G. Here, the harvesting of the blood vessel C extending toward the inguinal portion A through the cut skin portion E2 of the knee D will be described. The harvesting comprises: removing the conical chip from the cannula tip end; inserting the cannula into the cavity G from the cut skin portion E2; and inserting the cannula toward the cut skin portion E1 of the knee D along the upper portion of the blood vessel C during observation with the rigid endoscope.

In the process of the inserting of the cannula into the cavity G, an operation comprises: operating the operation portion in the proximal end of the cannula to move the traction portion forwards/backwards; holding the blood vessel C with the loop portion in the distal end to strip the vessel from the subcutaneous tissue 102 and connective tissue on the blood vessel 103; and cutting a plurality of side branches F branched from the middle of the blood vessel C by the incision forceps. This operation is repeated to harvest the blood vessel C between the cut skin portion E2 and inguinal portion A.

Moreover, in the great saphenous vein extraction system, the blood vessel C has to be prevented from being damaged when the side branches F are cut from the blood vessel C to be extracted. To safely cut the branches it is important to operate the blood vessel C by the traction portion in an arbitrary direction and to hold the vessel at a distance from incision forceps. When the blood vessel C is operated and held by the traction portion in this manner, tension is applied to the side branches F to be cut. Therefore, the side branches F can clearly be identified, and the side branches F can be cut without damaging the blood vessel C.

However, in the related-art manual operation, when the blood vessel C is held and pressed by the traction portion, a hand side of root portions of the side branches F is pressed with respect to the view field in accordance with a shape of the traction portion. Therefore, when the blood vessel C is pushed in a front surface direction of the view field in this state, the blood vessel C is bent, and rises on the back side of the side branch F. At this time, the incision forceps are projected forwards to cut the side branches F, and the blood vessel C which has risen may be damaged by mistake.

When the traction portion for holding the blood vessel C exists before the side branch F in this manner, the portion obstructs the front observation view field, and the positional states of the side branches F and blood vessel C cannot satisfactorily be confirmed. Therefore, also in this case, the blood vessel C may be damaged by mistake.

Since all the side branches F branched from the blood vessel C are searched under the endoscope and cut one by one in the above-described great saphenous vein extraction system, it takes considerable time to extract the blood vessel C. Moreover, to cut the side branches F, the side branches F cannot be held by the loop portion. Therefore, there is possibility that the treatment is performed in the unstable state. In this case, the blood vessel C may be damaged.

BRIEF SUMMARY OF THE INVENTION

An object of the present invention is to provide a living tissue harvesting apparatus which can safely hold living tissues such as a blood vessel without obstructing an observation view field and easily cut the living tissues.

The object of the present invention is achieved by the following living tissue harvesting apparatus. That is, according to one aspect of the present invention, there is provided a living tissue harvesting apparatus comprising: a sheath which can be inserted into a body through a cut skin portion; an endoscope inserted through the sheath; a cutting device which is disposed at the sheath and which can cut a living tissue; and a holder which is disposed at the sheath to hold a harvesting object tissue in the body and which includes a press discharge portion to press-discharge the harvesting object tissue in a direction detached from the cutting device, wherein the holder includes a hook portion to catch the living tissue in a position disposed opposite to the cutting device so that the cutting device and hook portion can move with respect to each other.

A living tissue harvesting apparatus according to another aspect of the invention comprises a tissue-holding space for holding a tissue harvested and tissue-catching means for opening and closing the tissue-holding space, thereby to catch the living tissue.

BRIEF DESCRIPTION OF THE SEVERAL VIEWS OF THE DRAWING

FIG. 1 is an exploded side view of a living tissue harvesting apparatus according to a first embodiment of the present invention;

FIG. 2A is a perspective view of a trocar;

FIG. 2B is a longitudinal sectional side view of the trocar;

FIG. 11A is a top plan view of a blood vessel holder;

FIG. 11B is a longitudinal sectional side view of the blood vessel holder;

FIG. 11C is a front view of the blood vessel holder;

FIG. 12A is a top plan view of a wiper;

FIG. 12B is a sectional view taken along a line 12B—12B of FIG. 12A;

FIG. 13 is a perspective view of a wiper operation portion;

FIG. 20 is a diagram showing the monitor image;

FIGS. 21A to 21C are perspective views showing a function of the blood vessel holder;

FIGS. 25A to 25C are plan views showing the function of the bipolar cutter;

FIGS. 26A and 26B are sectional views inside the body showing the function of the bipolar cutter;

FIG. 30 is a perspective view of the tip end of the treatment sheath;

FIG. 31 is a perspective view of the tip end of the treatment sheath;

FIG. 32 is a plan view of the blood vessel holder according to a first modification example of the first embodiment;

FIG. 33 is a plan view of the blood vessel holder according to a second modification example of the first embodiment;

FIG. 42A is a side sectional view of an embodiment in which the blood vessel holder also functions as the wiper;

FIG. 42B is a front view of an apparatus of the embodiment of FIG. 42A;

FIG. 42C is a 42C direction arrow view of FIG. 42A;

FIG. 44A is a longitudinal sectional side view of the tip end of the treatment sheath, showing the constitution for scraping off the foreign materials sticking to the holder;

FIG. 44B is a perspective view seen from an arrow 44B direction of FIG. 44A;

FIG. 44C is a front view of the treatment sheath of FIG. 44A;

FIG. 61 is a partially sectional plan view showing a first example of an engagement constitution of a holding rod and blood vessel holder main unit;

FIG. 62 is a partially sectional plan view showing a second example of the engagement constitution of the holding rod and blood vessel holder main unit;

FIG. 63A is a partially sectional plan view (open state) showing a third example of the engagement constitution of the holding rod and blood vessel holder main unit;

FIG. 63B is a partially sectional plan view (closed state) showing a third example of the engagement constitution of the holding rod and blood vessel holder main unit;

FIG. 64A is a partially sectional plan view (open state) showing a fourth example of the engagement constitution of the holding rod and blood vessel holder main unit;

FIG. 64B is a partially sectional plan view (closed state) showing the fourth example of the engagement constitution of the holding rod and blood vessel holder main unit;

FIG. 65 is a plan view of a first modification example of the blood vessel holder of a second embodiment;

FIG. 66A is a plan view (closed state) of a second modification example of the blood vessel holder of the second embodiment;

FIG. 66B is a plan view (open state) of the second modification example of the blood vessel holder of the second embodiment;

FIG. 67A is a front view of a third modification example of the blood vessel holder of the second embodiment;

FIG. 67B is a plan view of the blood vessel holder of FIG. 67A;

FIGS. 68A to 68D are explanatory views of a function of the blood vessel holder of FIGS. 67A and 67B;

FIG. 69A is a front view of the blood vessel holder in the closed state according to a fourth modification example of the second embodiment;

FIG. 69B is a plan view of the blood vessel holder of FIG. 69A;

FIG. 70A is a front view of the blood vessel holder in the open state according to the fourth modification example of the second embodiment;

FIG. 70B is a plan view of the blood vessel holder of FIG. 70A;

FIG. 71 is a perspective view showing an opening/closing mechanism of the blood vessel holder according to the fourth modification example of the second embodiment;

DETAILED DESCRIPTION OF THE INVENTION

Figure 3B:
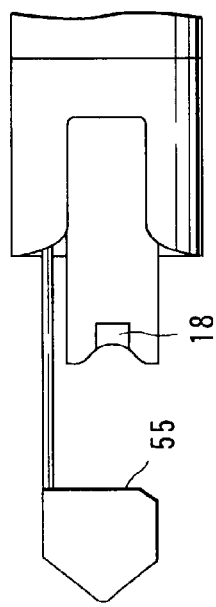
FIG. 3B is a plan view of a tip end of the treatment sheath of FIG. 3A.

Embodiments of the present invention will be described hereinafter with reference to the drawings.

FIG. 1 shows an endoscopic blood vessel harvesting apparatus as a living tissue harvesting apparatus in which a holder (blood vessel holder) according to a first embodiment of the present invention is incorporated. This apparatus is constituted of a trocar 1, treatment sheath 2, dissector 3 as expansion means, and rigid endoscope 4 as an endoscope.

As shown in FIGS. 2A and 2B, the trocar 1 is integrally molded of a synthetic resin material, and a cylindrical guide tube 6 is obliquely inserted through a substantially disc-shaped flange 5. The inner and outer surfaces of the guide tube 6 are coated with a lubricant in order to improve slip at an insertion time. A tip end 6a of the guide tube 6 is cut at an acute angle, and the end surface of the tip end 6a is formed substantially in parallel to the flange 5.

Furthermore, an airtight ring portion 7 is integrally disposed in an inner peripheral surface in a base end of the guide tube 6, and an air supply head 8 is integrally disposed in a middle portion. Moreover, an adhesive layer 9 such as an adhesive tape is disposed on the lower surface of the flange 5, and the trocar 1 can be fixed so as to adhere to a scurf skin.

Figure 3A:
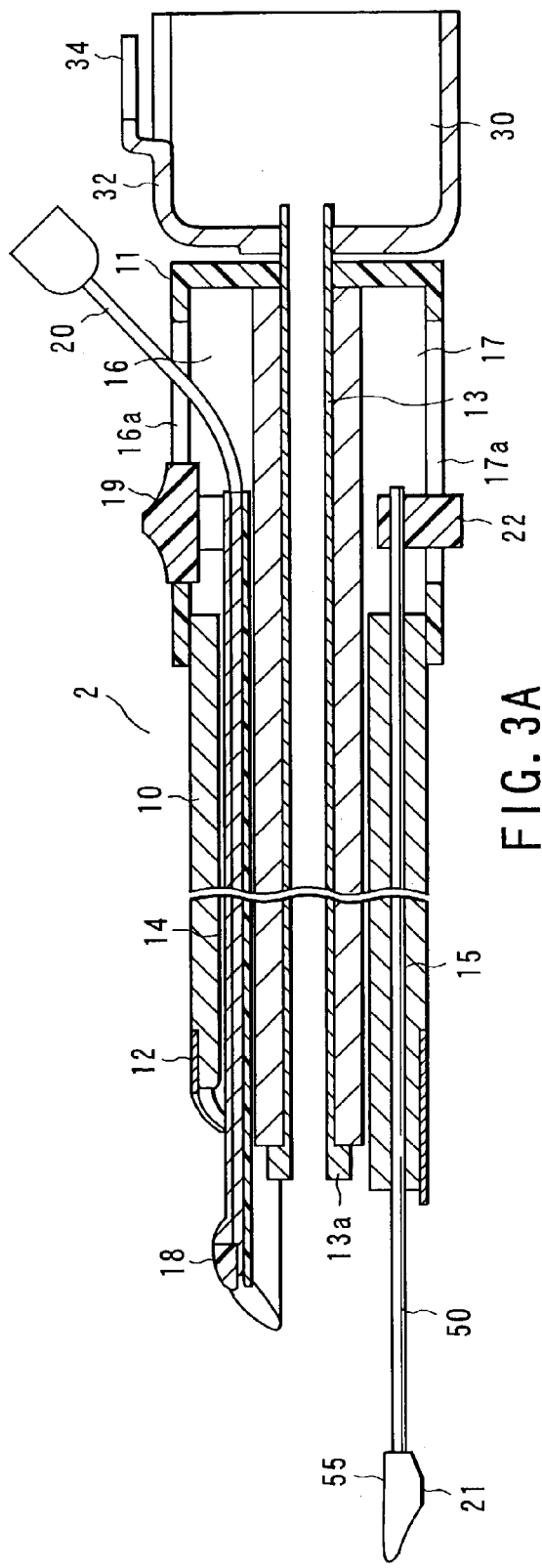
FIG. 3A is a longitudinal sectional side view of a treatment sheath from which a rigid endoscope is removed.
Figure 4:
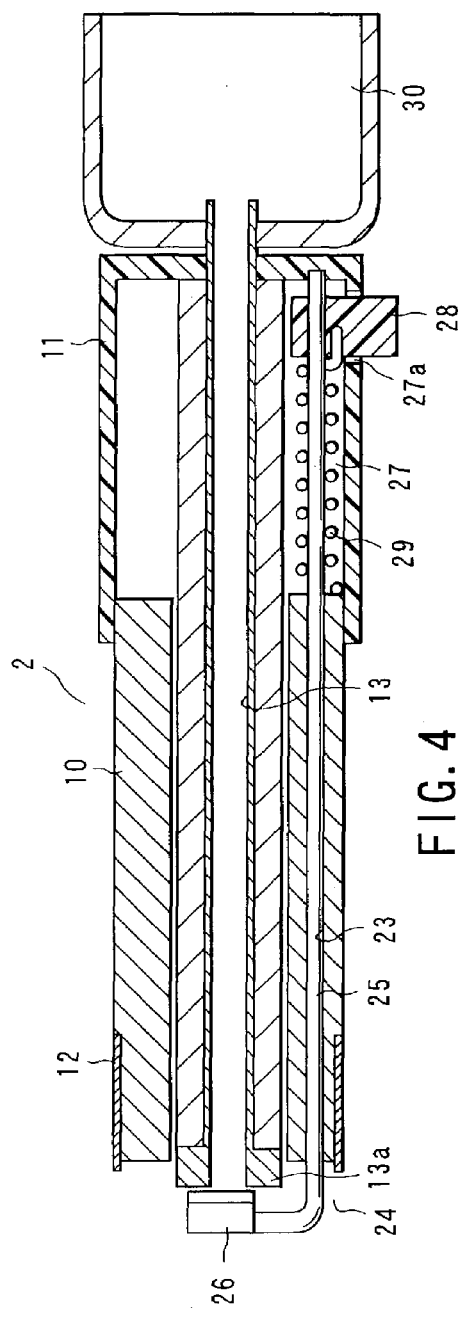
FIG. 4 is a longitudinal sectional plan view of the treatment sheath from which the rigid endoscope is removed.

The treatment sheath 2 will next be described. The sheath is constituted as shown in FIGS. 3A, 3B and 4. A sheath main unit 10 is a straight cylindrical member formed of a synthetic resin material, and the surface of the unit is coated with a lubricant to improve slip at an insertion time. An operation portion cover 11 constituting a grasp portion is attached to a proximal end of the sheath main unit 10, and a tip end cover 12 is attached to a distal end.

As shown in FIGS. 3A and 3B, an endoscope channel 13 is disposed over the whole length of an axial center portion of the sheath main unit 10. The proximal end of the endoscope channel 13 projects on a hand side through the operation portion cover 11, and a flange portion 13a projecting from the front end surface of the sheath main unit 10 is disposed in a distal end. A first treatment device channel 14 is disposed in a portion eccentric upwards and a second treatment device channel 15 is disposed in a portion eccentric downwards so that the endoscope channel 13 is held between the channels in the sheath main unit 10. Therefore, the first treatment device channel 14 and second treatment device channel 15 are substantially symmetrically arranged in positions most apart from each other via the endoscope channel 13.

The proximal end of the first treatment device channel 14 opens in a first slide operation portion 16 inside the operation portion cover 11, and the proximal end of the second treatment device channel 15 opens in a second slide operation portion 17 in the operation portion cover 11. A bipolar cutter 18 as a cutting apparatus described later is inserted through the first treatment device channel 14 so that the cutter can move forwards/backwards in an axial direction, and a treatment device operation portion 19 is disposed in a range of an elongate hole 16a of the first slide operation portion 16 in the proximal end so that the portion can slide in the axial direction. When the treatment device operation portion 19 is pulled to the proximal end, the distal end of the bipolar cutter 18 can be held in the first treatment device channel 14. Moreover, the bipolar cutter 18 is connected to a bipolar cable 20, and the bipolar cable 20 is derived toward the outside through the elongate hole 16a.

A blood vessel holder 21 as a blood vessel holding member described later is inserted through the second treatment device channel 15 in such a manner that the holder can move forwards/backwards in the axial direction, and a holder operation portion 22 is disposed in a range of an elongate hole 17a of the second slide operation portion 17 in the proximal end in such a manner that the portion can slide in the axial direction.

Furthermore, as shown in FIG. 4, a through hole 23 is disposed in the axial direction in one side portion of the endoscope channel 13 inside the sheath main unit 10. A wiper rod 25 of a wiper 24 described later is inserted through the through hole 23 in such a manner that the rod can rotate. The distal end of the wiper rod 25 is bent substantially in an L shape, and a wiper rubber 26 is disposed on the tip end of the rod.

The proximal end of the wiper rod 25 extends to a rotating operation portion 27 inside the operation portion cover 11, and is rotatably supported on the inner wall of the operation portion cover 11. A wiper operation portion 28 is fixed to the proximal end of the wiper rod 25, and the wiper operation portion 28 can rotate in a range of an elongate hole 27a which extends in a peripheral direction of the operation portion cover 11.

Moreover, an endoscope holding portion 30 is disposed on the hand side of the operation portion cover 11 in a fixed state with respect to the endoscope channel 13. The endoscope holding portion 30 includes a sufficient cavity for containing an eyepiece portion 31 of the rigid endoscope 4, and a cutout portion 34 into which a light guide head 33 disposed on the eyepiece portion 31 is inserted/engaged is formed in a part (upper part) of a peripheral wall 32.

Figure 6:
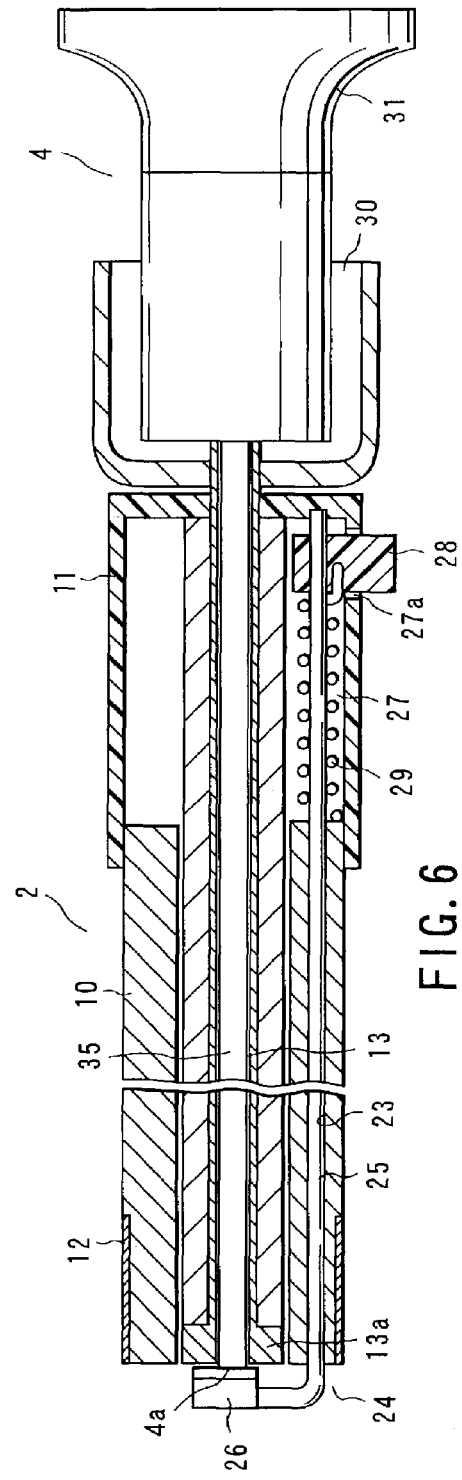
FIG. 6 is a longitudinal sectional plan view of the treatment sheath through which the rigid endoscope is inserted.
Figure 5:
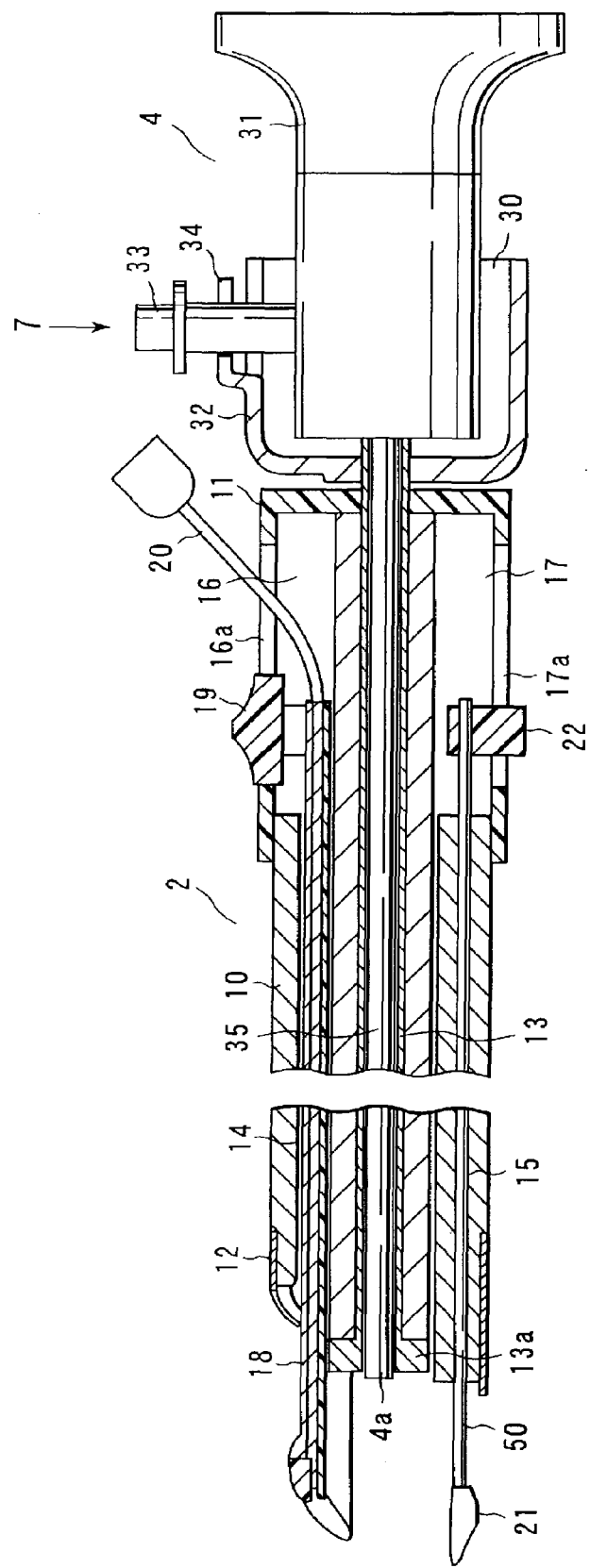
FIG. 5 is a longitudinal sectional side view of the treatment sheath through which the rigid endoscope is inserted.
Figure 7:
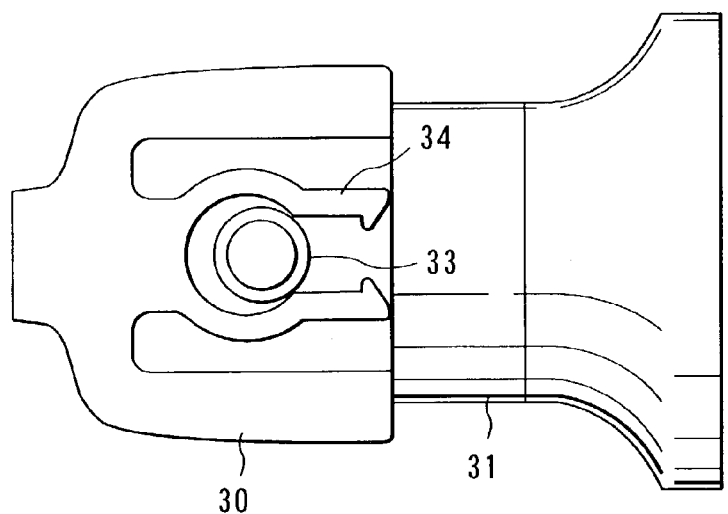
FIG. 7 is a diagram seen from an arrow 7 direction of FIG. 5.

Therefore, as shown in FIGS. 5 to 7, an insertion portion 35 of the rigid endoscope 4 is inserted into the endoscope channel 13, the light guide head 33 is inserted/engaged into the cutout portion 34 so as to hold the eyepiece portion 31 in the endoscope holding portion 30, the rigid endoscope 4 is then held with respect to the treatment sheath 2 and positioned in the axial direction. The sheath main unit 10 and the operation portion cover 11 are secured to the endoscope channel 13 and can rotate. The endoscope channel 13 and endoscope holding portion 30 are fixed. Hence, that part of the treatment sheath 2 which is more distal from the cover 11 than the rigid endoscope 4 can be held and rotate in rotatable state, as long as the treatment sheath 2 and the rigid endoscope 4 remain coupled together.

The bipolar cutter 18 will next be described.

As shown in FIGS. 9A to 10C, the bipolar cutter 18 includes: a cutter main unit 40 which is inserted in a body; a tip-end treatment portion 40a which is disposed in the tip end of the cutter main unit 40 to cut the blood vessel; and electrodes 42, 43 which are disposed in the tip-end treatment portion 40a to electrically cut the blood vessel. The cutter main unit 40 is formed of an insulating member (including a ceramic member) such as a synthetic resin material, and has a shape of a strip plate member bent in a arc shape along a arc inner peripheral surface of the sheath main unit 10. The curved shape (roof shape) of the cutter main unit 40 prevents the tissue from sagging from the upper side (presses/discharges a fat tissue in a body cavity) as described later, and is useful for securing the view field of the rigid endoscope 4.

A guide portion for guiding the blood vessel into the electrodes 42 and 43 with the movement of the cutter main unit 40 in the axial direction is formed in the tip-end treatment portion 40a of the cutter main unit 40. In the present embodiment, the guide portion is formed by a notch groove (slit) 41 cut in a V shape. In this case, sides 41a, 41b forming the V shape extend upwards to the top portion of the arc portion on the proximal-end side from opposite edges of the distal end of the cutter main unit 40, and form a tissue guide surface of the notch groove (hereinafter referred to as the V groove) 41 which tapers on the proximal-end side.

A pair of electrodes 42, 43 disposed opposite to each other are fixed/disposed on a bottom of the V groove 41, that is, an intersection of the respective sides 41a, 41b forming the V shape. The electrodes 42, 43 are not disposed in the same plane, and are positioned vertically opposite to each other.

Of these two electrodes, the upper electrode 42 has a surface area larger than that of the lower electrode 43. That is, the area of the upper electrode 42 in contact with the tissue is large. On the other hand, the area of the lower electrode 43 in contact with the tissue is small. Thereby, a current flows in the lower electrode 43, increasing the current density in the lower electrode 43. Therefore, the lower electrode 43 functions as an incision (cutting) electrode. The current density in the upper electrode 42 does not increase until the cutting starts. The upper electrode 42 therefore functions as a coagulation electrode. Hereinafter, the upper electrode 42 will be referred to as "body-side electrode," and the lower electrode 43 will be referred to as "cut electrode."

The body-side electrode 42 and cut electrode 43 are connected to lead wires 44, 45, and these lead wires 44, 45 are laid along the upper and lower surfaces of the cutter main unit 40, and connected to the bipolar cable 20. Furthermore, the lead wires 44, 45 are coated with insulating films 46, 47, and insulated. It is to be noted that portions of the bipolar cutter 18 other than the electrodes 42, 43 may also be formed by a transparent material (acryl, and the like).

The blood vessel holder 21 according to the present embodiment will next be described in detail with reference to FIGS. 11A to 11C. As shown in FIGS. 11A to 11C, the blood vessel holder 21 includes one operation rod 50 as a shaft portion which is moved forwards/backwards in the sheath main unit 10, and a main unit which is disposed in the tip end of the operation rod 50 to hold the harvesting object blood vessel 61. The main unit is formed of the synthetic resin material substantially in a triangular shape in a plan view, the upper surface is formed in a flat surface 48, and the lower surface is formed in a arc concave surface 49 which forms a press groove to press the harvested blood vessel 61. This arc concave surface 49 functions as a press discharge portion which presses/discharges the harvested blood vessel 61 in a direction apart from the bipolar cutter 18 as described later. Moreover, the operation rod 50 is connected to a lopsided position in a rear-end portion of the blood vessel holder 21 (the operation rod 50 is connected to a position eccentric from a center axis of the main unit of the blood vessel holder 21). It is to be noted that the operation rod 50 is inserted through the second treatment device channel 15 so as to be movable forwards/backwards.

The tip end of the blood vessel holder 21 is formed as an acute-angled stripping portion 51 for stripping the tissue. Moreover, first left and right taper surfaces 52a, 52b are symmetrically formed in the blood vessel holder 21 so as to be linked from the stripping portion 51. That is, the tip end of the main unit is formed in a taper shape which tapers at the acute angle. Furthermore, inclined surfaces 53a, 53b are formed in upper and lower surfaces of the stripping portion 51 toward the tip end so that the upper and lower surfaces have a small width. A hem portion of the first taper surface 52a on a side opposite to the connected portion of the blood vessel holder 21 to the operation rod 50 is formed on a second taper surface 54 which has a arc shape, and the second taper surface 54 is continued to a hook portion 55 including a flat surface which is positioned in the rear end of the blood vessel holder 21 so as to catch the blood vessel. That is, the main unit further includes the rear end for catching the living tissue. Concretely, as shown in FIG. 3B, the hook portion 55 is disposed in a position opposite to the bipolar cutter 18 in the axial direction.

Opposite side walls of the blood vessel holder 21 forming the arc concave surface 49 include a third taper surface 59 which extends downwards from the stripping portion 51, and a fourth taper surface 58 which extends downwards from the hook portion 55.

The wiper 24 will be described in detail. The wiper is constituted as shown in FIGS. 12A and 12B. That is, the wiper rubber 26 fixed to the distal end of the wiper rod 25 is fixed to an L-shaped folded portion of the wiper rod 25 by adhesion or insert molding, and is disposed at right angles to the axial direction. The wiper rubber 26 includes a scraping portion 26a which has a triangular section and flexibility. Thereby, by rotation of the wiper rubber 26, foreign particles sticking to the objective lens surface 4a of the rigid endoscope 4, such as blood, mucosa, and fat, can be scraped off. In this case, the scraping portion 26a has flexibility. Therefore, even when a stepped portion is generated between the tip end surface of the sheath main unit 10 and the objective lens surface 4a, the rubber goes beyond the stepped portion and slides against the objective lens surface 4a.

As shown in FIG. 13, one end of the torsion coil spring 29 including the coil spring disposed on the wiper rod 25 of the wiper 24 abuts on the end surface of the sheath main unit 10, and the other end is disposed between the unit and the wiper operation portion 28 in a compressed state and is further engaged with the side surface of the wiper operation portion 28. Therefore, the torsion coil spring 29 generates a rotation torque T for rotating the wiper rod 25 in one direction, and a force F for urging the wiper rod 25 toward the proximal end direction of the sheath main unit 10. Thereby, the wiper rubber 26 is urged in a direction in which the rubber retreats to the side of the objective lens surface 4a of the rigid endoscope 4, and a direction in which the rubber contacts the objective lens surface 4a.

Figure 9A:
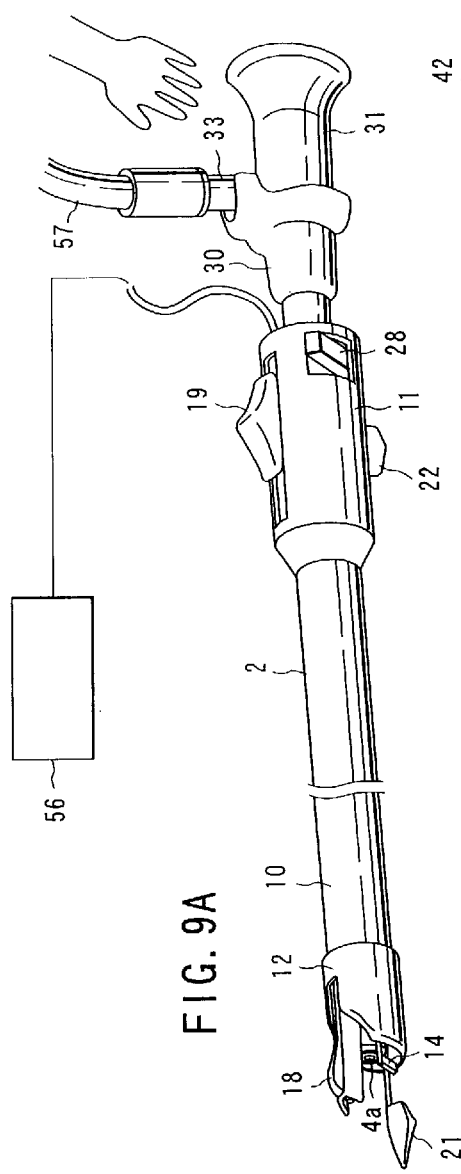
FIG. 9A is a perspective view of a blood vessel harvesting apparatus.
Figure 9C:
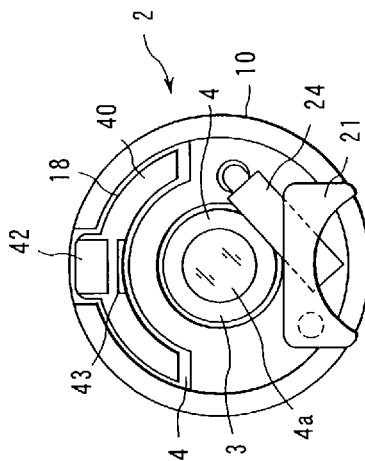
FIG. 9C is a front view of the tip end of the blood vessel harvesting apparatus.
Figure 9B:
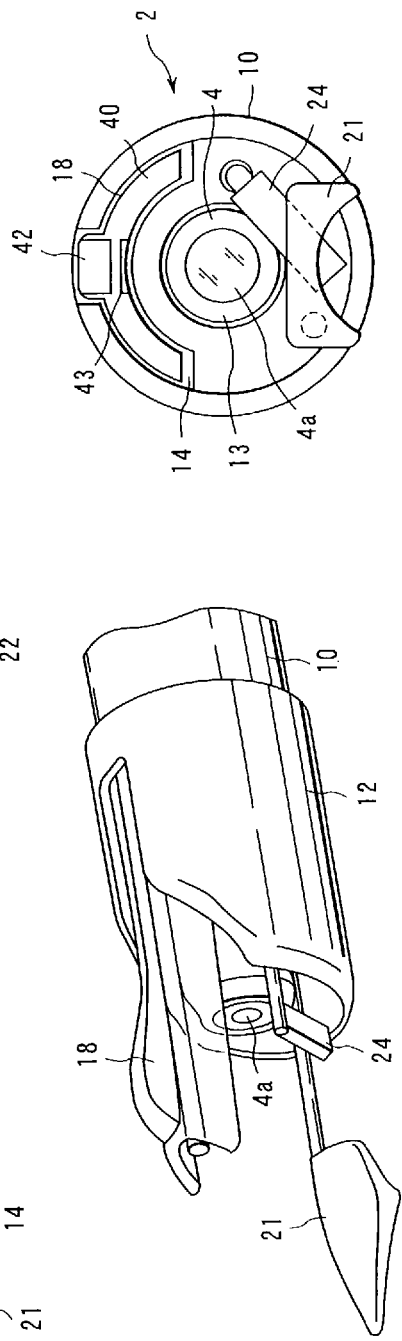
FIG. 9B is a perspective view of a tip end of the blood vessel harvesting apparatus.
Figure 10A:
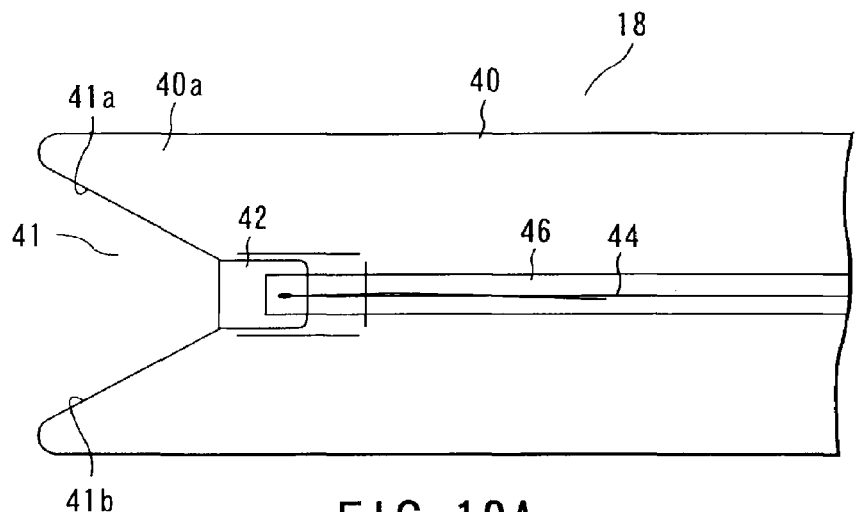
FIG. 10A is a top plan view of a bipolar cutter.
Figure 10B:
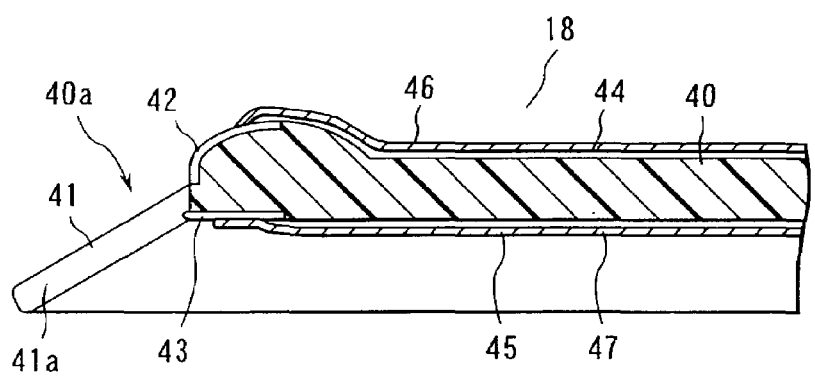
FIG. 10B is a longitudinal sectional side view of the bipolar cutter.
Figure 10C:
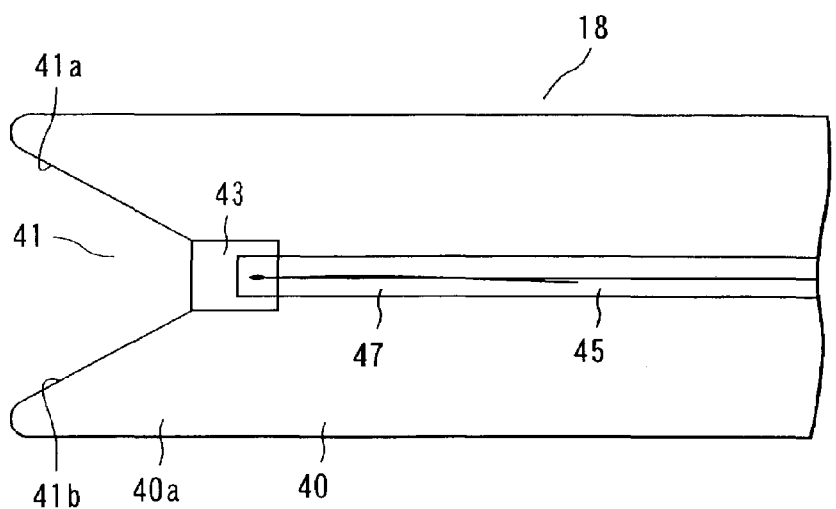
FIG. 10C is a lower surface view of the bipolar cutter.

FIGS. 9A and 9B show that the insertion portion 35 of the rigid endoscope 4 is inserted into the endoscope channel 13 of the treatment sheath 2. In this state, the bipolar cutter 18 and blood vessel holder 21 projects from the tip end of the treatment sheath 2. The bipolar cable 20 is connected to a high-frequency generation apparatus 56, and a light guide cable 57 is connected to the light guide head 33.

Figure 8:
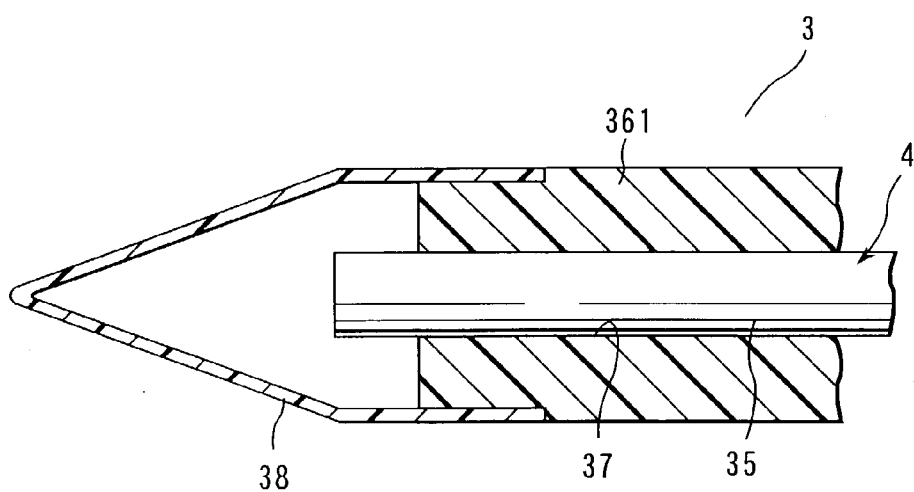
FIG. 8 is a longitudinal sectional side view of the tip end of a dissector.

The dissector 3 will next be described. As shown in FIG. 8, an insertion path 37 for passing through the insertion portion 35 of the rigid endoscope 4 is disposed in the axial center portion of an insertion cylindrical portion 36 which has a straight cylindrical shape. Hydrophilic coating is provided on the surface of the insertion cylindrical portion 36 in order to improve the slip at the insertion time. A stripping member 38 formed in a conical shape by a transparent synthetic resin material is fixed to the distal end of the insertion cylindrical portion 36. An endoscope holding portion 39 is disposed in the proximal end of the insertion cylindrical portion 36 so that the eyepiece portion 31 of the rigid endoscope 4 is held. It is to be noted that the endoscope holding portion 39 preferably includes the same constitution as that of the endoscope holding portion 30 of the treatment sheath 2.

A case will be described in which the blood vessel harvesting apparatus constituted as described above is used to harvest a blood vessel as a harvesting object (hereinafter referred to as the blood vessel) such as a great saphenous vein extending over the whole length including a inguinal portion A of a thigh of a leg and an ankle.

Figure 14:
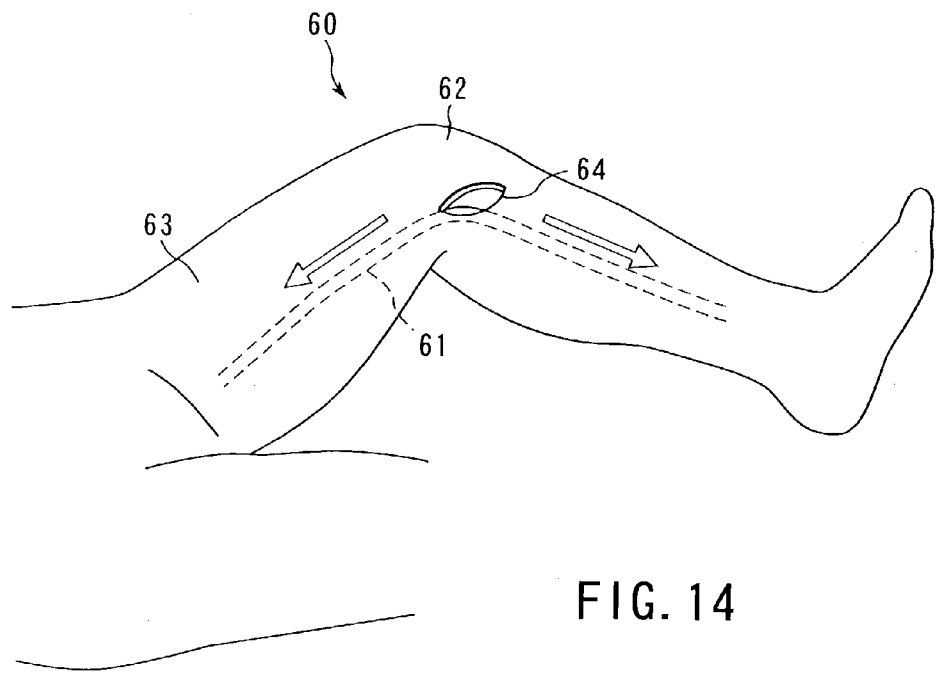
FIG. 14 is a diagram of a state in which a cut skin portion is formed in a leg.

FIG. 14 shows a leg 60 and blood vessel 61. First, when the blood vessel 61 between a knee 62 and inguinal portion 63 is harvested, a cut skin portion 64 is made in one portion of the knee 62 right above the blood vessel 61 by a scalpel.

Subsequently, the blood vessel 61 is exposed in the cut skin portion 64 by a forceps. Furthermore, a tissue right above the blood vessel 61 is stripped by a distance which can be observed through the cut skin portion 64 with the naked eyes with a similar forceps.

Figure 15:
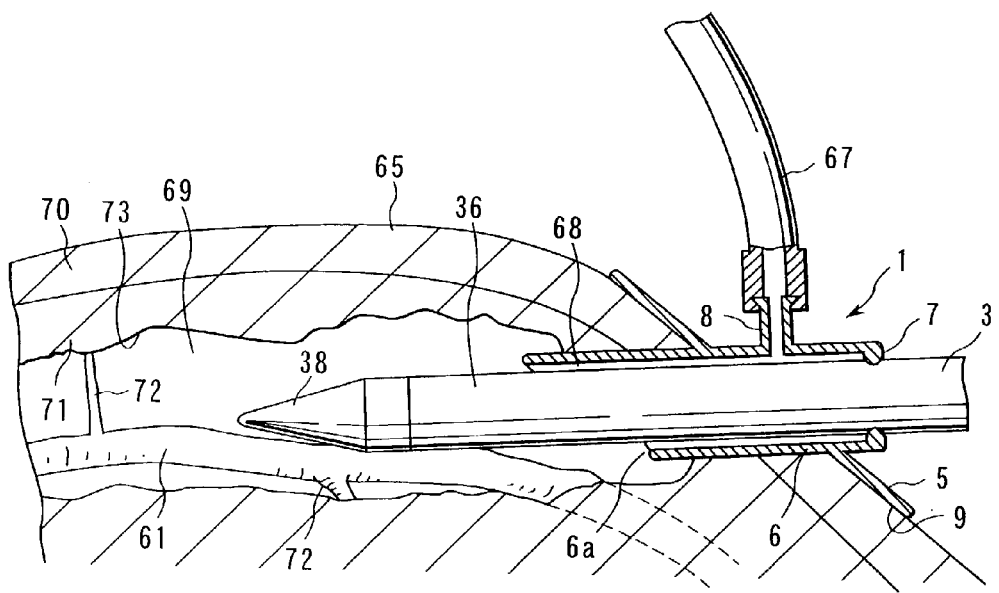
FIG. 15 is a sectional view of a state in which the trocar is attached to the cut skin portion of the leg and the trocar is used as a guide to insert the dissector into a cavity.

Subsequently, the rigid endoscope 4 is inserted into the dissector 3. The endoscope 4 is thereby held in the endoscope holding portion 39 and secured to the light guide head 33. The stripping member 38 is passed is photographed by a TV camera 75 coupled to a TV camera head 74 that is connected to the eyepiece portion 31 of the rigid endoscope 4 inserted in the insertion cylindrical portion 36. A monitor 76 displays the image of the member 38 thus photographed. As shown in FIG. 15, the stripping member 38 is inserted along the blood vessel 61. Where the member is little inserted, the guide tube 6 of the trocar 1 is obliquely inserted toward the inguinal portion 63 (substantially in parallel to the blood vessel 61, the tip end 6a is turned downwards, and the adhesive layer 9 in the lower surface of the flange 5 is bonded/fixed to a scurf skin 65. In this state, an air supply tube 67 connected to an air supply pump 66 is connected to the air supply head 8.

In this case, since the outer peripheral surface of the insertion cylindrical portion 36 is closely attached to the airtight ring portion 7, the inside of the guide tube 6 and cavity 69 is brought into an airtight state, and an air supply path 68 is secured between the guide tube 6 and insertion cylindrical portion 36.

The light guide head 33 of the rigid endoscope 4 is connected to a light source apparatus 78 via the light guide cable 57. Therefore, the cavity 69 can be irradiated and illuminated with an illuminating light from the tip end of the rigid endoscope 4. When the air supply pump 66 is driven, air is supplied into the cavity 69 via the air supply tube 67, air supply head 8, and air supply path 68, and the cavity 69 is expanded. At this time, since the insertion cylindrical portion 36 of the dissector 3 adheres to the airtight ring 7, gas does not leak to the outside, and the cavity 69 can therefore securely be expanded.

Figure 17:
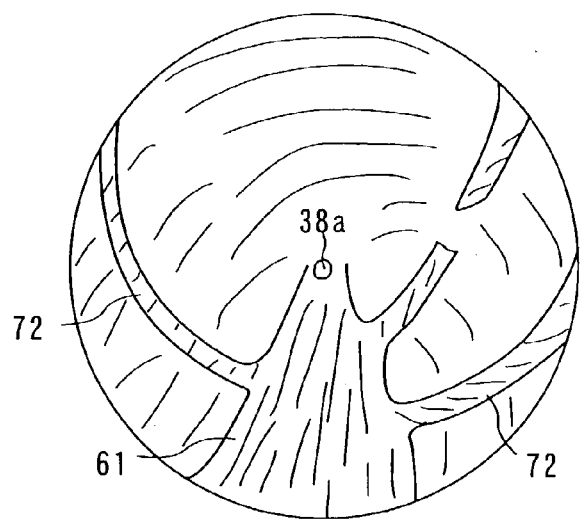
FIG. 17 is a diagram showing a monitor image.

A subcutaneous tissue 70 as a lower layer of the scurf skin 65 and connective tissue on the blood vessel 71 exist in the cavity 69. Moreover, the blood vessel 61 exists in the lower part of the connective tissue on the blood vessel 71, a plurality of side branches 72 are branched from the blood vessel 61, and the other ends of the side branches 72 are connected to the connective tissue on the blood vessel 71. Moreover, a subcutaneous fat 73 is attached to the connective tissue on the blood vessel 71. At this time, when the monitor image is checked, the image is displayed as shown in FIG. 17. The operator can clearly observe the blood vessel 61 and side branches 72 by the monitor 76. It is to be noted that a reference numeral 38a in FIG. 17 denotes the image of the tip end of the stripping member 38 of the dissector 3.

In this way, during the inserting of the dissector 3, in a state in which the cavity 69 is observed by the monitor 76, the connective tissue on the blood vessel 71, blood vessel 61, and side branches 72 are stripped by the stripping member 38 without damaging the side branches 72, and the stripping member 38 is gradually moved forwards by an operation comprising: little pushing inwards; or little returning the member 38. At this time, even when the dissector 3 is vertically/transversely swung, the trocar 1 is not detached from the scurf skin 65. This is because the trocar 1 is fixed to the scurf skin 65 by the adhesive layer 9. In this manner, the dissector 3 is moved from the knee 62 toward the inguinal portion 63 along the blood vessel 61.

The operation described above is repeated several times on the tissue surrounding the blood vessel so that the blood vessel may be peeled off at the harvesting region.

Figure 16:
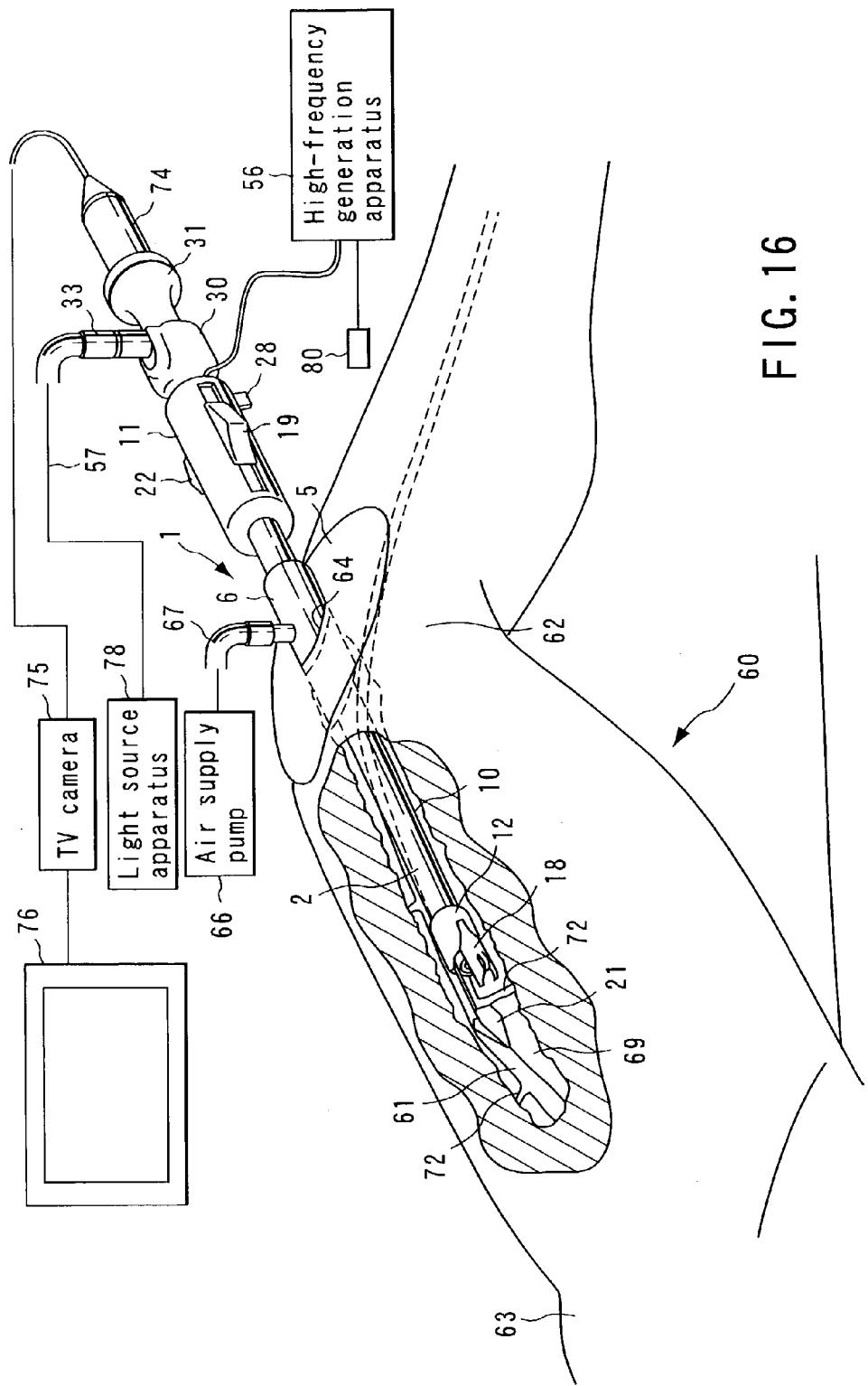
FIG. 16 is a whole constitution diagram of a state in which the trocar is used as the guide to insert the treatment sheath into the cavity.

When a manual stripping operation is completed by using the dissector 3, the dissector 3 is extracted from the trocar 1. The rigid endoscope 4 is detached from the dissector 3. As shown in FIG. 16, the endoscope 4 is inserted into the treatment sheath 2. The sheath 2 holding the rigid endoscope 4 is inserted into the guide tube 6 of the trocar 1. The operation then goes to a treatment step.

In the treatment step, air is applied from the air supply pump 66. The dissector 3 holds the tissue scraped. The treatment is performed in the view field of the endoscope, by using treatment sheath 2 inserted.

While the operation portion cover 11 of the treatment sheath 2 is grasped with operator's one hand, for example, the holder operation portion 22 is moved forwards with the operator's thumb, and the blood vessel holder 21 then projects from the tip end cover 12 of the sheath main unit 10. Moreover, the cutter operation portion 19 is moved forwards with the index finger of the hand in which the operation portion cover 11 is held, and the bipolar cutter 18 then projects from the tip end cover 12. That is, while the operator holds the operation portion cover 11 with one hand, the operator can move the blood vessel holder 21 or bipolar cutter 18 forwards/backwards.

Figure 18:
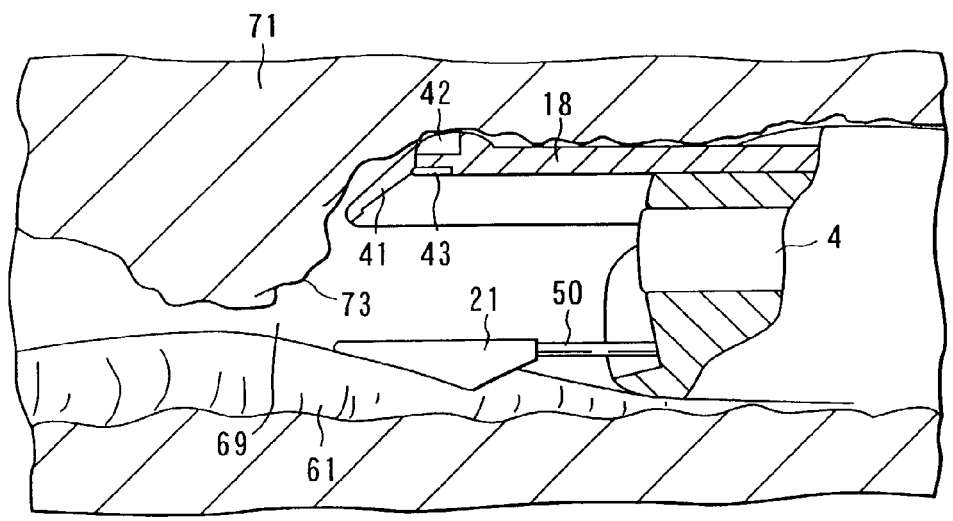
FIG. 18 is a sectional view of the state in which the treatment sheath is inserted in the cavity.

Therefore, as shown in FIG. 18, when a large amount of subcutaneous fat 73 exists in the connective tissue on the blood vessel 71 of the cavity 69, the treatment sheath 2 is pushed forwards to expand the cavity 69 in a projected state of the bipolar cutter 18. At this time, the bipolar cutter 18 prevents the tissue from sagging downwards (presses/discharges the fat tissue in the body cavity) by the curved shape (roof shape) of the cutter main unit 40, so that the view field of the rigid endoscope 4 can satisfactorily be secured. Also, at this time, since the lower surface of the blood vessel holder 21 is formed in the arc concave 49, the holder can be slid and moved forwards on the upper surface of the blood vessel 61, and the blood vessel 61 is not stopped from being damaged.

Figure 19:
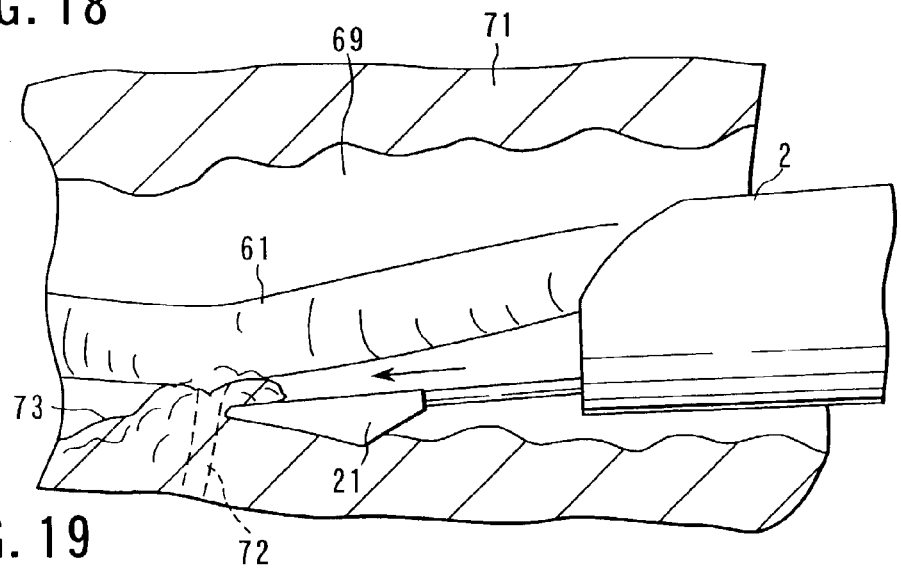
FIG. 19 is a sectional view of a treatment state in the cavity.

As shown in FIG. 19, the side branches 72 are buried in the subcutaneous fat 73 in some case. In this case, the blood vessel holder 21 is projected from the treatment sheath 2, and the stripping portion 51 of the blood vessel holder 21 is pressed onto the subcutaneous fat 73 to strip the subcutaneous fat 73 from the blood vessel 61 or the side branch 71. When the whole treatment sheath 2 is rotated in the peripheral direction in the guide tube 6 of the trocar 1, the blood vessel holder 21 can be rotated to exfoliate the subcutaneous fat 73 from the side branch 72. Since this state is displayed as the monitor image in the monitor 76 as shown in FIG. 20, the operator can confirm the posture of the blood vessel holder 21 by the monitor image, and the blood vessel 61 and side branch 72 are prevented from being damaged.

While the subcutaneous fat 73 of the cavity 69 is removed, the treatment sheath 2 is pushed into the cavity 69, and the blood vessel holder 21 is allowed to approach the side branch 72 as a target. Also in this case, the arc concave 49 is brought in contact with the upper surface of the blood vessel 61, the holder is slid on the upper surface of the blood vessel 61 and can be moved forwards, and the blood vessel 61 is prevented from being damaged.

FIGS. 21A to 21C show a manual operation of holding the side branch 72 by the blood vessel holder 21. The blood vessel holder 21 has the first taper surface 52a, and this surface is continued to the second taper surface 54, the blood vessel holder 21 is moved forwards, and the side branch 72 first is brought in contact with the first taper surface 52a (see FIG. 21B).

When the blood vessel holder 21 is further moved forwards, the side branch 72 contacts the second taper surface 52b from the first taper surface 52a falls, sliding on the hook portion 55, and caught by the hook portion 55 (see FIG. 21C). That is, the first taper surface 52a (or the second taper surface 52b) can allow the blood vessel holder 21 to contact the side branch 72, escape from the side branch 72, and easily move ahead of the side branch 72 (side opposite to the view field with respect to the side branch 72). Moreover, the third taper surface 59 also largely contributes to the ease of forward movement of the blood vessel holder 21. That is, because of the presence of the third taper surface 59, the blood vessel holder 21 can smoothly move forwards without being caught by the tissue which exists below. Therefore, the side branch 72 can easily be held by the forward operation of the blood vessel holder 21.

Figure 22:
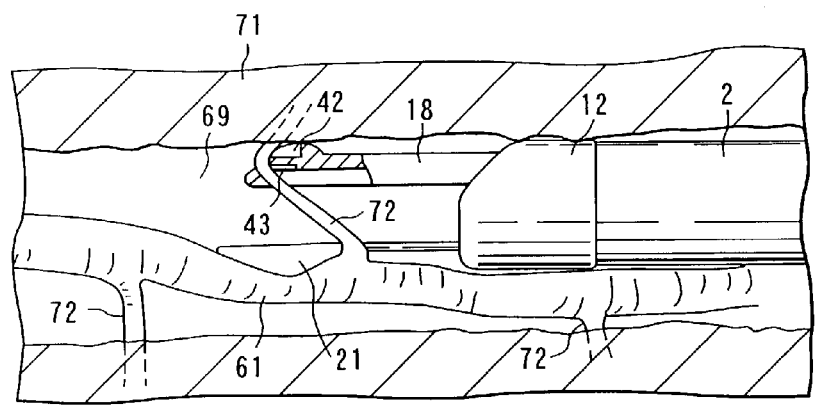
FIG. 22 is a sectional view inside the body in the treatment state.

When the middle of the side branch 72 is hooked on the hook portion 55 of the blood vessel holder 21 and the blood vessel holder 21 is drawn on the hand side (at this time, for example, the hook portion 55 is relatively moved with respect to the bipolar cutter 18), tension is applied to the side branch 72 as shown in FIG. 22. At this time, the blood vessel holder 21 can smoothly move toward the hand side without being caught by the tissue disposed below because of the presence of the fourth taper surface 58. Since one operation rod 50 is connected to the blood vessel holder 21 at this time, and the observation view field is satisfactory. The operation rod 50 is connected to the position eccentric from the center axis of the blood vessel holder 21, and the operation rod 50 lies right above the blood vessel 61. This broadens the observation view further. Therefore, the running of the blood vessel C can easily and clearly be conformed. Hence, the blood vessel holder 21 can hold the side branch 72 more readily and firmly. As a result, it is easy to apply the tension to the side branch 72. Particularly, if the blood vessel holder 21 is formed of the transparent material, the visibility of the blood vessel and tissue can further be improved (therefore, in another preferred embodiment of the present invention, the blood vessel holder 21 is formed by the transparent material).

Figure 23:
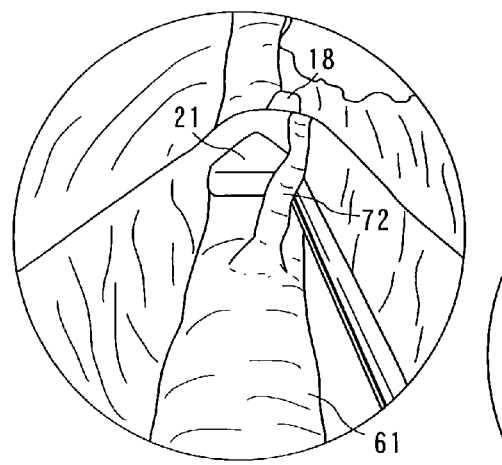
FIG. 23 is a diagram showing the monitor image.

FIG. 23 shows the monitor image in which the side branch 72 is hooked on the hook portion 55 of the blood vessel holder 21. An operator can check by this monitor image that the side branch 72 has been held. When the side branch 72 is held by the blood vessel holder 21 not on the hand side, but on the opposite side of the side branch 72, the side branch 72 is positioned on the hand side of the observation view field, and the periphery of the side branch 72 can clearly be confirmed by the rigid endoscope 4 (when the blood vessel holder 21 is disposed on the hand side of the side branch 72, the blood vessel holder 21 obstructs the front observation view field, and the positional states of the side branch 72 and blood vessel 61 cannot satisfactorily be confirmed). Therefore, as described later, the side branch 72 can safely be cut without damaging the blood vessel 61.

When the state shown in FIG. 23 is formed, next the bipolar cutter 18 is moved forwards (the bipolar cutter 18 is relatively moved with respect to the hook portion 55) and approaching the side branch 72 held by the blood vessel holder 21. The hook portion 55 of the holder 21 may not be used, depending upon the position that the side branch assumes. Rather, the side branch may be held at a position away from the hook portion 55. In this case, the blood vessel 61 can be held in the arc concave 49. Further, as seen from the monitor image of FIG. 24, the blood vessel 61 can be moved backwards from the bipolar cutter 18 by using the blood vessel holder 21, preventing the bipolar cutter 18 from contacting the blood vessel 61. This operation can easily be achieved by disposing the bipolar cutter 18 opposite to the blood vessel holder 21 as described above. By this arrangement, a predetermined distance can securely be kept between the incised/treated portion of the side branch 72 and the blood vessel 61, the side branch 72 is incised by the bipolar cutter 18 in the position apart from the blood vessel 61, and the blood vessel 61 can be prevented from being damaged. When the predetermined distance can be kept between the incised/treated portion of the side branch 72 and the blood vessel 61 in this manner, a knot margin can be secured in binding the cut portion of the side branch 72 left on the blood vessel 61 side with a ligature or the like, after the side branch 72 is cut and the blood vessel 61 is extracted. This constitution is therefore useful.

Figure 24:
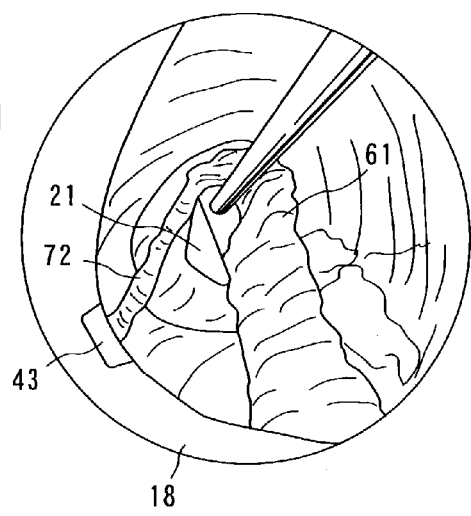
FIG. 24 is a diagram showing the monitor image.

As seen from the monitored image shown in FIG. 24, the hook portion 55 of the blood vessel holder 21 may not used, depending upon the positions that the blood vessel 61 and the side branch 72 take. Instead, the other part of the holder 21, located outside the portion 55, may be used to hold the side branch. In this case, the holder 21 can hold the blood vessel at its concave surface 49. Thus, the blood vessel 61 can be moved away from the bipolar cutter 18 by using the blood vessel holder 21, in order to prevent the cutter 18 from contacting the blood vessel 61.

FIGS. 25A to 25C show a manual operation of cutting the side branch 72 by the bipolar cutter 18. Since the V groove 41 is formed in the tip end of the bipolar cutter 18, and when the bipolar cutter 18 is moved towards the side branch 72, the side branch 72 is drawn toward the bottom of the V groove 41. Therefore, as shown in FIG. 26A, the side branch 72 contacts the cut electrode 43, and the body-side electrode 42 contacts the connective tissue on the blood vessel 71 or side branch 72. That is, in the bipolar cutter 18 according to the present embodiment, the side branch 72 can be guided into the electrodes 42, 43 substantially positioned in the intersection of the respective sides 41a, 41b by the wall surfaces of the V groove 41 corresponding to the respective sides 41a, 41b which form the V shape.

After confirming by the monitor image that the side branch 72 contacts the cut electrode 43 and the body-side electrode 42 contacts the connective tissue on the blood vessel 71 or side branch 72, the operator operates a foot switch 80 of the high-frequency generation apparatus 56 to supply a high-frequency current. The body-side electrode 42 contacts the blood vessel connecting tissue or the side branch 72 at a larger area than the cut electrode 43 contacts the tissue or the side branch 72. This means that the current density is higher in the cut electrode 43 than in the body-side electrode 42. Hence, the cut electrode 43 can cut the tissue efficiently. Then a region in contact with the body-side electrode 42 of the connective tissue on the blood vessel 71 or side branch 72 is coagulated, and the side branch 72 is cut by the cut electrode 43. That is, as FIG. 26B shows, the portion of the blood vessel 61 connected to the connective tissue on the blood vessel 71 by the side branch 72 is cut off by cutting the side branch 72. At this time, since the body-side electrode 42 having the large contact area is disposed on the upper side (body side) farther from the blood vessel 61 than the cut electrode 43, the thermal influence on the blood vessel 61 is minimized.

Since the bipolar cutter 18 is just pressed onto the blood vessel in this manner, the blood vessel can be cut by the presence of the V groove 41. That is, operation other than the forward/backward movement is not required in cutting the blood vessel. Therefore, the degree of freedom of the operation of the whole endoscopic blood vessel harvesting apparatus decreases (necessary operation is performed with a small degree of freedom), and operability is enhanced.

When the side branch 72 is cut as described above, as shown in FIG. 27, the blood vessel holder 21 is passed under the blood vessel 61 to lift up the blood vessel. It is confirmed by the monitor image shown in FIG. 28 whether or not the side branch 72 is completely cut/treated.

The treatment sheath 2 is further pushed forwards in the cavity 69. While observing the monitored image of the cavity 69, the surgeon may move the blood vessel holder 21 toward the next side branch 72. The surgeon repeats the above-mentioned manual operation, using the bipolar cutter 18, on all side branches 72. The blood vessel 61 is thereby cut completely from the connective tissue on the blood vessel 71.

Figure 29:
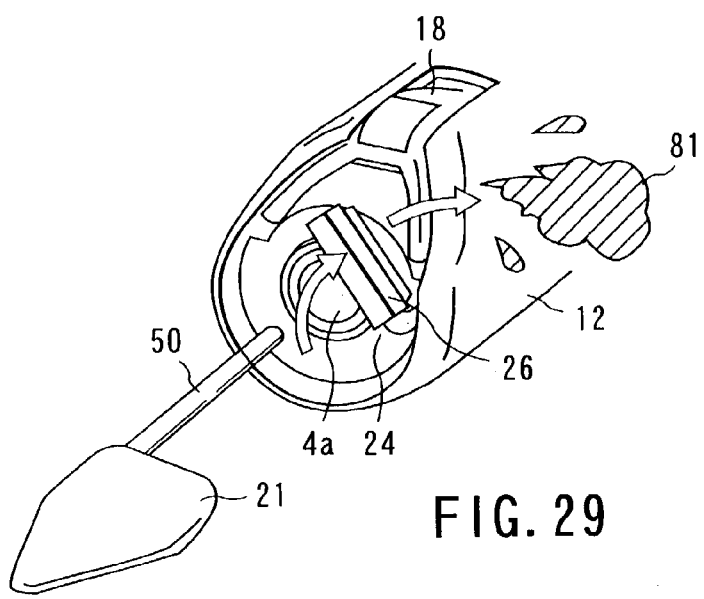
FIG. 29 is a perspective view of the tip end of the treatment sheath.

When the method of cutting the side branch 72 is repeated in this manner, the foreign materials 81 such as blood, mucosa, and subcutaneous fat 73 adhere to the objective lens surface 4a of the rigid endoscope 4, and the view field by the rigid endoscope 4 is sometimes obstructed. In this case, while the operation portion cover 11 remains to be grasped, and when the wiper operation portion 28 is manually rotated against an urging force of the torsion coil spring 29, as shown in FIG. 29, the wiper 24 rotates via the wiper rod 25, and the foreign materials 81 such as the blood, mucosa, and subcutaneous fat 73 sticking to the objective lens surface 4a can be scraped away by the scraping portion 26a of the wiper rubber 26.

The wiper 24 is urged by the torsion coil spring 29. When the wiper operation portion 28 is released from the fingers, the wiper is returned in a retreat direction from the objective lens surface 4a. Therefore, when the above-described operation is repeated several times, even the foreign materials 81 such as the subcutaneous fat 73 adhering to and not easily dropping from the objective lens surface 4a can cleanly be scraped off. Moreover, when the fingers are released from the wiper operation portion 28, the wiper 24 returns, moving a away from the objective lens surface 4a and is still biased. Hence, the wiper 24 would not project, by accident, into the view field. In other words, wiper 24 would not narrow the view field of the rigid endoscope 4.

Moreover, when the cutting of the side branch 72 by the bipolar cutter 18 is repeated, as shown in FIG. 30, the foreign materials 81 such as the mucosa and subcutaneous fat 73 also adhere to the inner surface of the bipolar cutter 18 because of the roof shape of the bipolar cutter 18. However, when the bipolar cutter 18 is moved backwards by the cutter operation portion 19 and drawn into the first treatment device channel 14, the mucosa and subcutaneous fat 73 are scraped off by the front end surface of the sheath main unit 10. Therefore, the foreign materials 81 adhering to the bipolar cutter 18 can easily be scraped off. It is to be noted that in the present embodiment, in order to scrape off the mucosa and subcutaneous fat 73 adhering to the bipolar cutter 18 by the front end surface of the sheath main unit 10, a clearance between the bipolar cutter 18 and sheath main unit 10 (clearance between the outer surface of the bipolar cutter 18 and the inner surface of the first treatment device channel 14) is set to be small.

As shown in FIG. 31, the scraped foreign materials 81 stick to the objective lens surface 4a of the rigid endoscope 4 and sometimes obstruct the view field. Even in this case, when the wiper operation portion 28 is operated to rotate the wiper 24 as described above, the foreign materials 81 sticking to the objective lens surface 4a can be scraped off.

While the operation of scraping off the foreign materials 81 sticking to the bipolar cutter 18 or objective lens surface 4a is repeated, the manual operation of cutting the side branch 72 to cut the blood vessel 61 from the connective tissue on the blood vessel 71 is repeated. When the operation reaches the inguinal portion 63, the cutting of the side branch 72 is terminated. Subsequently, the small incision is formed in the inguinal portion 63 right above the blood vessel 61 with the scalpel. The blood vessel 61 is pulled out through the cut skin portion and cut. The operator can cut the drawn portion of the blood vessel 61, and ligate both cut ends of the blood vessel 61 with a suture.

Subsequently, the harvesting operation of the blood vessel 61 extending toward the ankle from the cut skin portion 64 of the knee 62 is carried out and finally one blood vessel (about 60 cm) is harvested from the cut skin portion 64. The manual operation is basically similar to the manual operation performed on the blood vessel 61 extending to the inguinal portion 63 from the knee 62, and the description thereof is omitted. The vessel which is cut on its both sides is removed from the cut skin portion 64.

In the method of harvesting the blood vessel 61, a manual operation is performed on the inguinal portion 63, and another manual operation is performed at the ancle. Instead, the blood vessel 61 may be first scraped from the connecting tissue 71 at both the inguinal portion 63 and the ancle. Then, the treatment sheath 2 may be used in place of the dissector 3 when the blood vessel 61 is completely cut from the connecting tissue 71. This reduces the number of times the sheath 2 and the dissector 3 should be exchanged with each other. The manual operation can be more smoothly carried out than otherwise.

As described above, in the blood vessel harvesting apparatus of the present embodiment, the blood vessel holder 21 includes the hook portion 55 for catching the blood vessel in the position opposite to the bipolar cutter 18, and the bipolar cutter 18 and hook portion 55 can move with respect to each other. Therefore, when the side branch 72 is hooked on the hook portion 55 and the blood vessel holder 21 is pulled on the hand side, as shown in FIG. 22, the tension can be added to the side branch 72. Moreover, the blood vessel 61 can be retracted in a direction apart from the bipolar cutter 18 by the blood vessel holder 21 so as to prevent the bipolar cutter 18 from contacting the blood vessel 61. That is, the predetermined distance can securely be kept between the incised/treated portion of the side branch 72 and the blood vessel 61, and the side branch 72 can be incised by the bipolar cutter 18 in the position distant from the blood vessel 61 to prevent the blood vessel 61 from being damaged. If the predetermined distance is thus kept between the incised/treated portion of the side branch 72 and the blood vessel 61 the knot margin can be secured in binding the cut portion of the side branch 72 remaining on the blood vessel 61 side with the ligature, in the case where the blood vessel 61 harvested is used as a bypass vessel to the heart. This constitution is therefore useful.

Only one operation rod 50 as the shaft portion for supporting and moving forwards/backwards the main unit is attached to the main unit of the blood vessel holder 21 of the present embodiment. Therefore, the observation view field by the rigid endoscope 4 is not largely obstructed by the operation rod 50.

Furthermore, in the blood vessel holder 21 of the present embodiment, since the operation rod 50 is connected to the position eccentric from the center axis of the main unit, the observation view field further becomes satisfactory, and the holding property of the side branch 72 by the blood vessel holder 21 is also improved. As a result, the tension is easily applied to the side branch 72. Moreover, when the operation rod 50 is disposed in the position eccentric from the center axis of the blood vessel holder 21 in this manner, the operation rod 50 is not positioned on the blood vessel 61, and therefore the running of the blood vessel C can easily and clearly be confirmed.

Additionally, since the blood vessel holder 21 of the present embodiment has the tip end (stripping portion 51 and taper surfaces 52a, 52b) formed in the taper shape tapering at the acute angle, the holder contacts the side branch 72, escapes from the side branch 72, and can easily move ahead of the side branch 72 (on the opposite side of the view field with respect to the side branch 72). Therefore, the side branch 72 can easily be held by the blood vessel holder 21 not on the hand side of the side branch 72, but on the opposite side. As a result, the side branch 72 is position on the hand side of the observation view field, the periphery of the side branch 72 can clearly be confirmed by the rigid endoscope 4, and the side branch 72 can safely be cut without damaging the blood vessel 61.

A modification example of the blood vessel holder 21 will next be described with reference to FIGS. 32 to 41B. It is to be noted that the constituting portions common to those of the above-described embodiment are denoted with the same reference numerals and the description thereof is omitted in the following modification example.

For a blood vessel holder 21A according to a first modification example shown in FIG. 32, a hook portion 55A in the rear end substantially has a C shape. That is, the rear end of the main unit of the blood vessel holder 21A has a holding surface substantially having the C shape to hold the hooked living tissue (it is to be noted that the press discharge portion is also disposed). Therefore, according to this main unit shape, a holding force in holding the living tissue such as the side branch 72 can be improved.

Moreover, a blood vessel holder 21B according to a second modification example shown in FIG. 33 includes a groove 100 substantially having a V shape in the tip end of the holder. Therefore, two stripping portions 51A, 51B are formed in the front end, and first taper surfaces 52a, 52b are formed on opposite sides of the respective stripping portions 51A, 51B. Furthermore, the tissue hook portion 55A substantially having the C shape is formed in the rear end in the same manner as in FIG. 32 (it is to be noted that the press discharge portion is also disposed). Therefore, according to the main unit shape, the function/effect similar to that of FIG. 32 is obtained, and the function/effect similar to that of the V groove 41 of the bipolar cutter 18 according to the above-described embodiment can be obtained. That is, when the blood vessel holder 21 is just moved forwards, the tissue is easily drawn into the V groove 100, the tissue is thereby stripped/incised by two stripping portions 51A, 51B, and stripping property (incision property) is improved.

Figure 34:
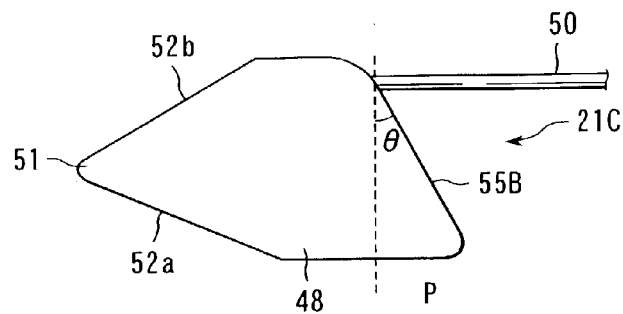
FIG. 34 is a plan view of the blood vessel holder according to a third modification example of the first embodiment.

Furthermore, for a blood vessel holder 21C according to a third modification example shown in FIG. 34, the rear end of the main unit is formed in a taper shape tapering at the acute angle. That is, a tissue hook portion 55B extends at a predetermined angle θ with respect to a surface P vertical to the operation rod 50 (it is to be noted that the press discharge portion is also disposed). Therefore, according to this main unit shape, the tissue hook portion 55B can easily be hooked on the side branch 72 on the front side of the side branch 72 (the opposite side of the view field with respect to the side branch 72). That is, the holding force of the side branch 72 is improved.

Figure 35:
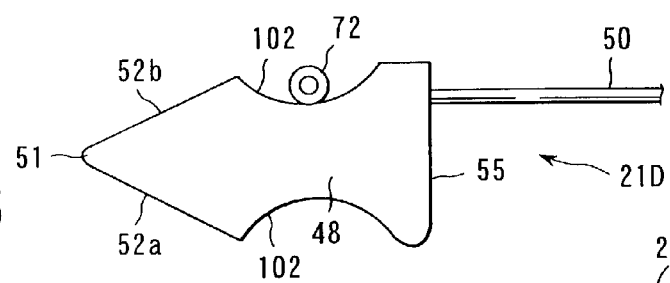
FIG. 35 is a plan view of the blood vessel holder according to a fourth modification example of the first embodiment.
Figure 45:
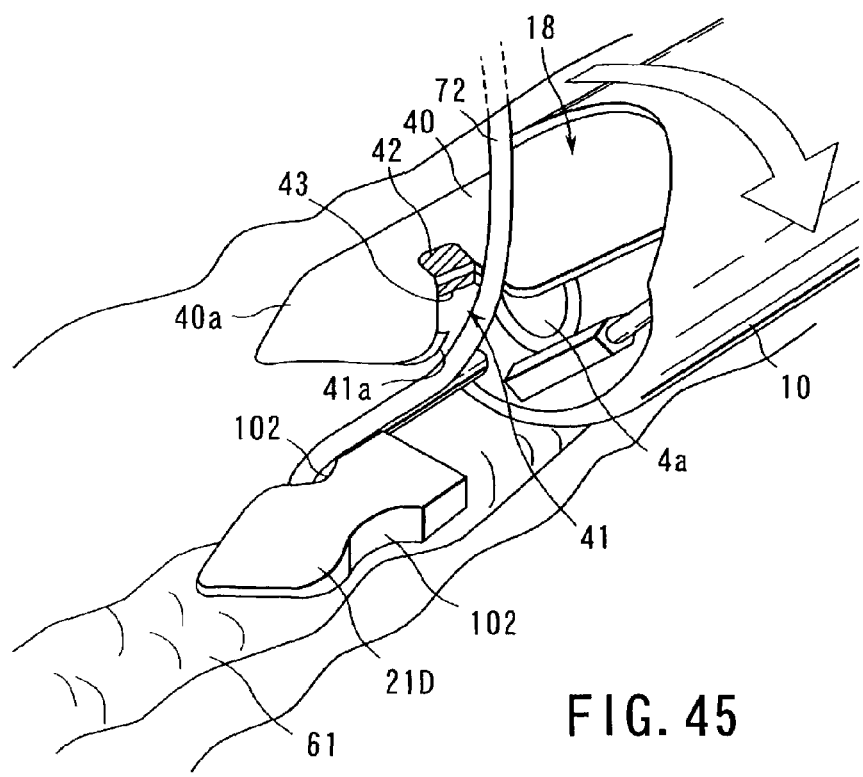
FIG. 45 is a perspective view showing one example of a treatment mode using the bipolar cutter which includes a V groove in a side portion and the holder.
Figure 46B:
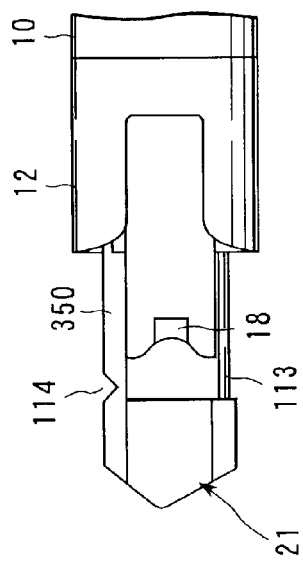
FIG. 46B is a plan view of the tip end of the treatment sheath of FIG. 46A.
Figure 46A:
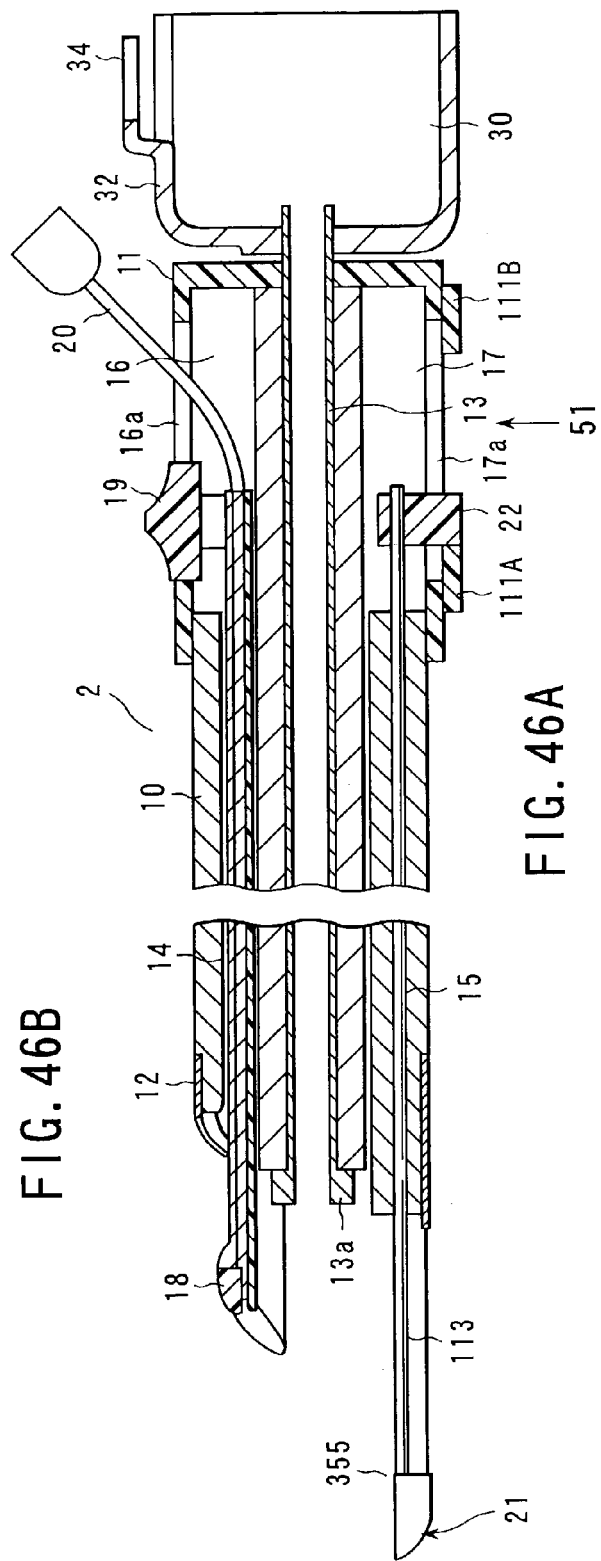
FIG. 46A is a longitudinal sectional side view of the treatment sheath from which the rigid endoscope is extracted in the living tissue harvesting apparatus according to a second embodiment of the present invention.
Figure 47:
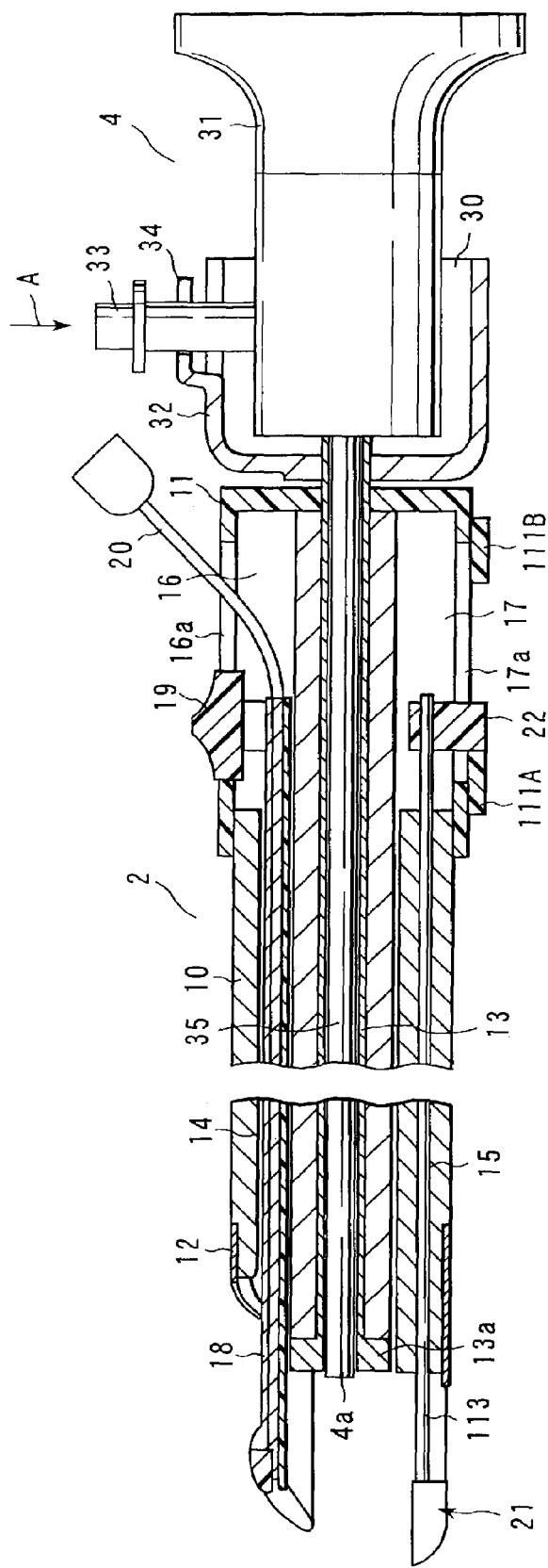
FIG. 47 is a longitudinal sectional side view of the treatment sheath through which the rigid endoscope is inserted.
Figure 48A:
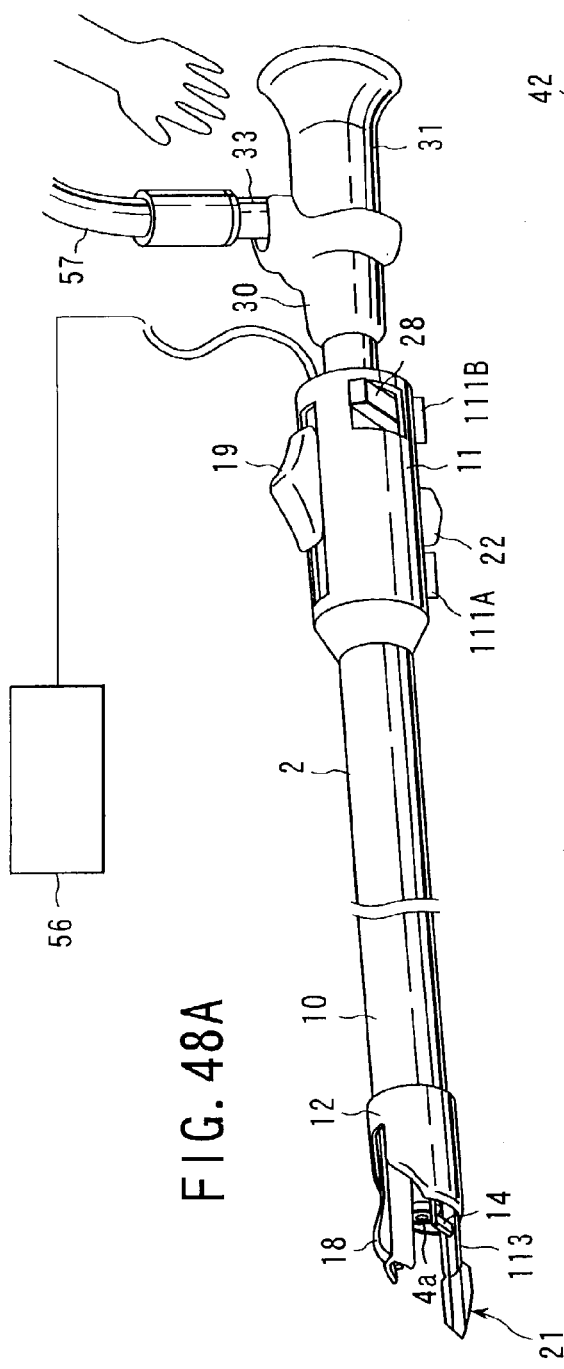
FIG. 48A is a perspective view of the blood vessel harvesting apparatus.
Figure 48B:
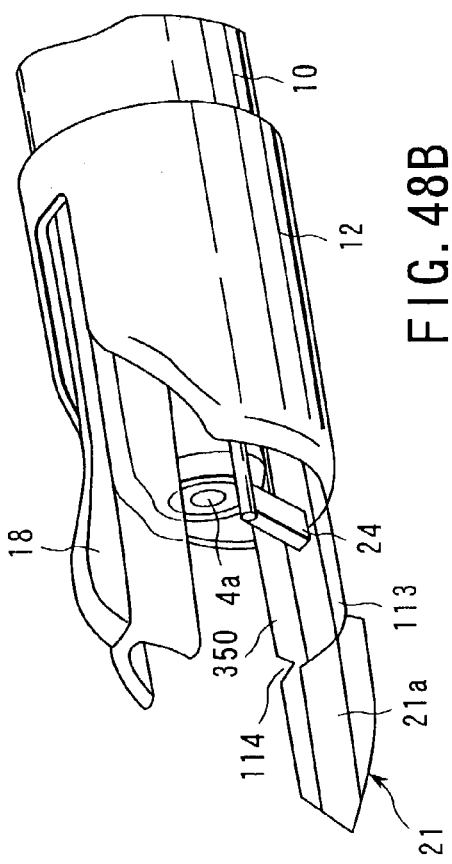
FIG. 48B is a perspective view of the tip end of the blood vessel harvesting apparatus.
Figure 48C:
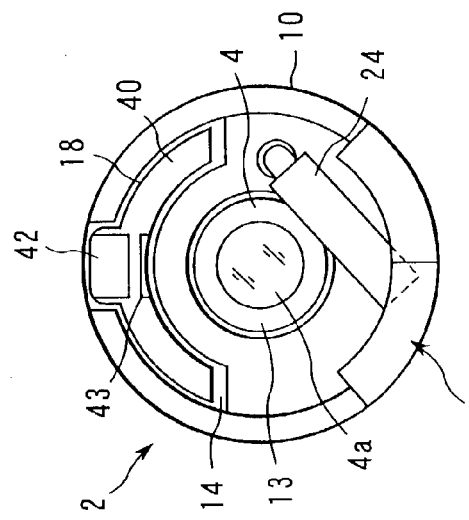
FIG. 48C is a front view of the tip end of the blood vessel harvesting apparatus.

Moreover, a blood vessel holder 21D according to a fourth modification example shown in FIG. 35 includes grooves 102, 102 each substantially having the C shape on opposite sides (it is to be noted that the press discharge portion is also disposed). Therefore, according to this main unit shape, the side branch 72 can be held in the groove 102. For example, as shown in FIG. 45, when the V groove 41 of the bipolar cutter 18 is disposed beside the cutter main unit 40, the side branch 72 can be cut from the side (during the cutting, the bipolar cutter 18 is rotated as shown by an arrow in the drawing). Therefore, the groove is useful. In this case, the V groove 41 guide the side branch 72 into the electrodes 42, 43 with the movement of the cutter main unit 40 in the direction substantially crossing at right angles to the axial direction, and the groove 102 of the blood vessel holder 21D can press the side branch 72 from the side (the tension is applied from the side).

Figure 36:
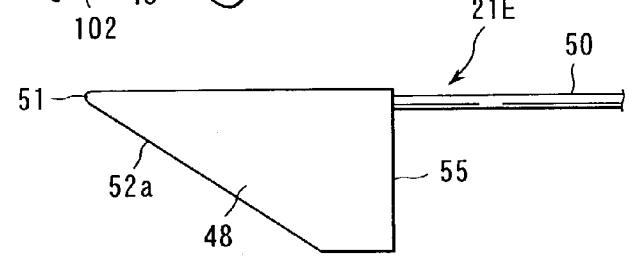
FIG. 36 is a plan view of the blood vessel holder according to a fifth modification example of the first embodiment.

For a blood vessel holder 21E according to a fifth modification example shown in FIG. 36, the stripping portion 51 is formed on an axial line of the operation rod 50 (it is to be noted that the press discharge portion is also disposed). Therefore, according to the main unit shape, since the operation force from the operation rod 50 can directly be transmitted to the stripping portion 51, stripping property is enhanced.

Figure 37:
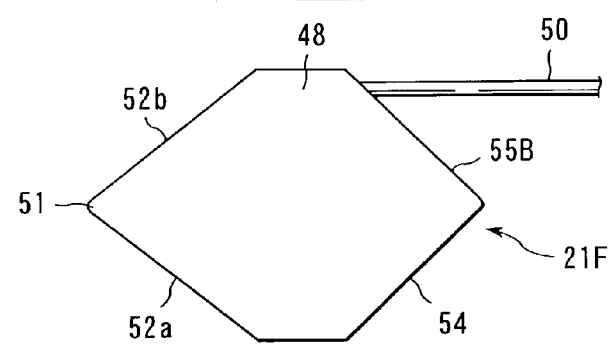
FIG. 37 is a plan view of the blood vessel holder according to a sixth modification example of the first embodiment.

For a blood vessel holder 21F according to a sixth modification example shown in FIG. 37, the rear end of the main unit is formed in the taper shape which tapers at the acute angle. That is, the tissue hook portion 55B extends at a predetermined angle with the operation rod 50 with respect to the vertical surface P, and the second taper surface 54 is formed longer than that of the above-described embodiment (it is to be noted that the press discharge portion is also disposed). Therefore, according to this main unit shape, the tissue hook portion 55B can easily be hooked on the side branch 72 on the front side of the side branch 72 (the opposite side of the view field with respect to the side branch 72) (the holding force is improved). Moreover, when the blood vessel holder 21 is returned on the hand side from the state of FIG. 21C, the holder can smoothly be drawn back without being caught by the tissue by the function of the taper shape of the rear end.

Figure 38:
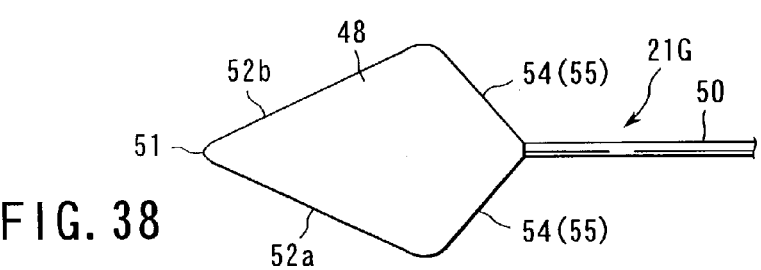
FIG. 38 is a plan view of the blood vessel holder according to a seventh modification example of the first embodiment.

For a blood vessel holder 21G according to a seventh modification example shown in FIG. 38, the operation rod 50 is disposed on the center axis of the main unit. Moreover, in this case, the stripping portion 51 is positioned on the axial line of the operation rod 50 (it is to be noted that the press discharge portion is also disposed). Therefore, according to this constitution, the main unit can be held with a good balance by the operation rod 50, the operation force from the operation rod 50 can directly be transmitted to the stripping portion 51, and the stripping property is enhanced.

Figures 39A, 39B:
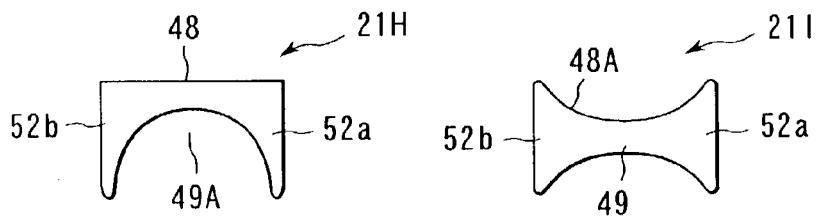
FIG. 39A is a front view of the blood vessel holder according to an eighth modification example of the first embodiment.
FIG. 39B is a front view of the blood vessel holder according to a ninth modification example of the first embodiment.

FIGS. 39A and 39B are diagrams of the blood vessel holder seen from the direction corresponding to FIG. 11C. A blood vessel holder 21H according to an eighth modification example shown in FIG. 39A has a arc concave surface 49A which has a curvature smaller than that of the arc concave surface 49 of the above-described embodiment. Therefore, according to this main unit shape, the holding force of the blood vessel 61 is enhanced.

Figure 27:
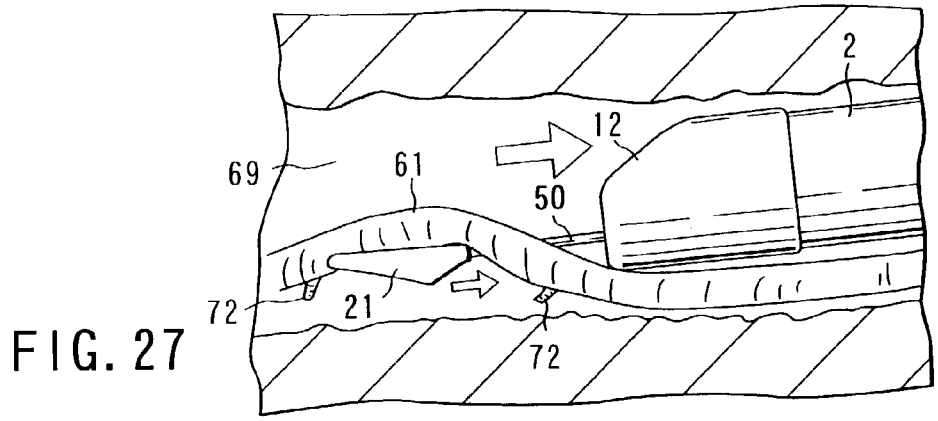
FIG. 27 is a sectional view inside the body in the treatment state.
Figure 28:
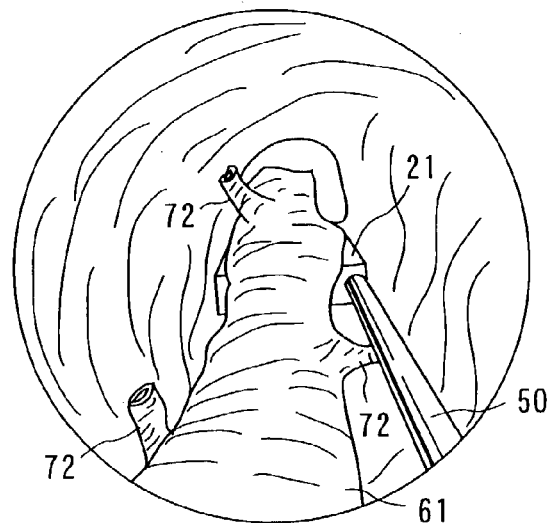
FIG. 28 is a diagram showing the monitor image.

Moreover, in a blood vessel holder 21I according to a ninth modification example shown in FIG. 39B, the arc concave surfaces are formed in opposite upper and lower surfaces of the main unit. That is, the flat upper surface of the main unit forms the arc shape. Therefore, according to the main unit shape, the blood vessel 61 can securely be held by the opposite upper and lower surfaces of the main unit. Particularly when the blood vessel holder 21 is passed under the blood vessel 61 to lift up the holder as shown in FIG. 27, and it is checked by the monitor image shown in FIG. 28 whether or not the side branch 72 is completely cut/treated, the blood vessel 61 can securely be held, and therefore these surfaces are useful.

Figure 40A:
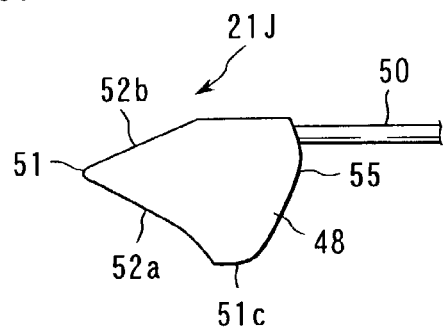
FIG. 40A a plan view of the blood vessel holder according to a tenth modification example of the first embodiment.
Figures 40B, 40C:
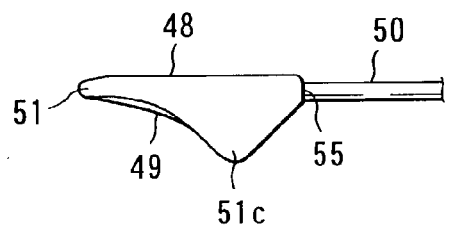
FIG. 40B is a side view of the blood vessel holder of FIG. 40A.
FIG. 40C is a front view of the blood vessel holder of FIG. 40A.

For a blood vessel holder 21J according to a tenth modification example shown in FIGS. 40A to 40C, the section curved downwards on one side substantially forms a hook or L shape, and the holder includes stripping portions 51, 51C in the tip and lower ends, respectively. Therefore, the portions can also bite and strip the tissue positioned under the blood vessel holder.

Figure 41A:
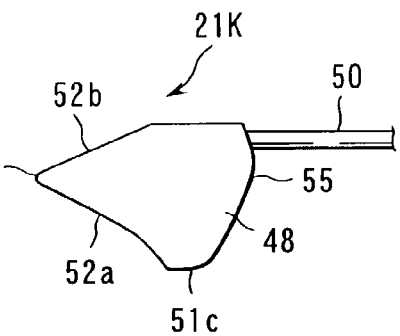
FIG. 41A is a plan view of the blood vessel holder according to an eleventh modification example of the first embodiment.
Figures 41B, 41C:
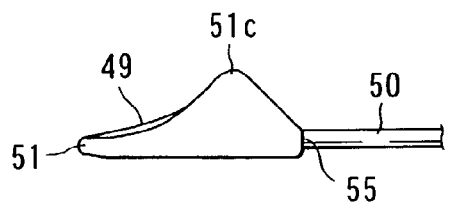
FIG. 41B is a side view of the blood vessel holder of FIG. 41A.
FIG. 41C is a front view of the blood vessel holder of FIG. 41A.

A blood vessel holder 21K according to an eleventh modification example shown in FIGS. 41A to 41C have a shape vertically inverse to that of FIGS. 40A to 40C, and the section curved upwards on one side substantially forms the hook or L shape. Therefore, the tissue positioned above the blood vessel holder can be bitten and stripped, and the blood vessel 61 can be held from below.

FIGS. 42A to 42C show an embodiment in which the blood vessel holder 21 also functions as the wiper 24. As shown, a scraping portion 26a of a wiper rubber 26 is disposed in the rear end surface of the main unit of the blood vessel holder 21. Moreover, a side flute 17b extending in a peripheral direction is formed in and linked with the proximal end of the elongate hole 17a formed in the axial direction of the second slide operation portion 17, and the holder operation portion 22 can move in the peripheral direction only in the range of the side flute 17b.

Therefore, in this constitution, while the holder operation portion 22 draws the blood vessel holder 21 on the hand side and the holder operation portion 22 is positioned in the side flute 17b, the blood vessel holder 21 is rotated, and the foreign materials such as the mucosa and subcutaneous fat adhering to the objective lens surface 4a of the rigid endoscope 4 can be scraped off by the scraping portion 26a of the blood vessel holder 21.

Figure 43:
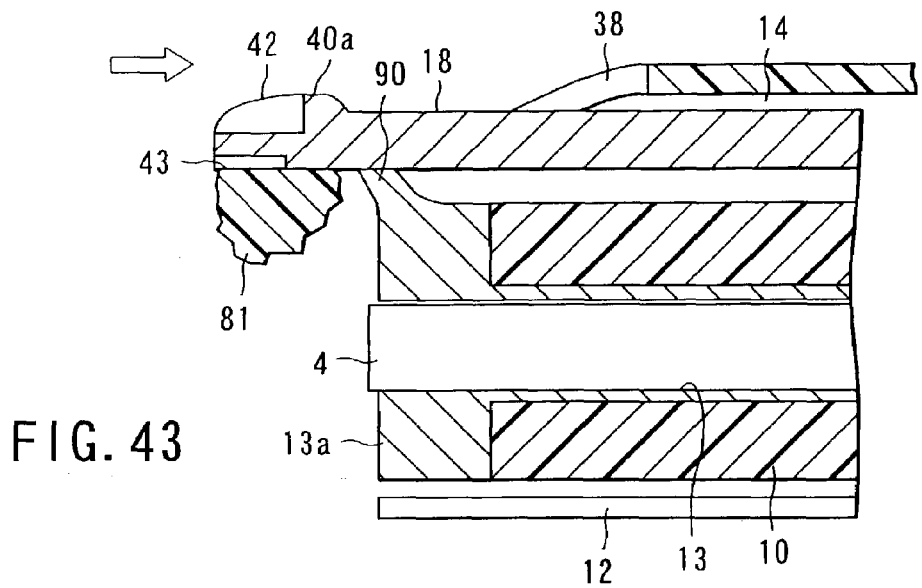
FIG. 43 is a sectional view showing another constitution for scraping off foreign materials sticking to the bipolar cutter.

FIG. 43 shows another constitution for scraping off the foreign materials 81 sticking to the bipolar cutter 18.

As shown, a cutter containing portion 38 connected to the first treatment device channel 14 is disposed in the tip end of the sheath main unit 10. This cutter containing portion 38 is formed so as to contain the whole tip-end treatment portion 40a, when the bipolar cutter 18 is drawn into the sheath main unit 10. A slide friction portion 90 projecting into the cutter containing portion 38 is formed in the flange portion 13a of the endoscope channel 13 which projects through the front end surface of the sheath main unit 10. When the tip-end treatment portion 40a is drawn into the cutter containing portion 38, the slide friction portion 90 slides onto the bipolar cutter 18 (tip-end treatment portion 40a), and the foreign materials 81 adhering to the bipolar cutter 18 (tip-end treatment portion 40a) can be scraped off the bipolar cutter 18 (tip-end treatment portion 40a). More precisely, the slide friction portion 90 is an elastic member or the like and always closely contacts the bipolar cutter 18. The slide friction portion 90 need not project so long as it remains in close contact with the bipolar cutter 18. In other words, the portion 90 can perform its function even if the clearance between it and the cutter 18 is small.

With this constitution, the foreign materials 81 can be scraped when the bipolar cutter 18 is drawn into the sheath main unit 10. Moreover, the foreign materials 81 can reliably be scraped from the slide friction portion 90 which is formed of the elastic member and constantly closely contacts the bipolar cutter 18 in a satisfactory state. Therefore, the foreign materials 81 from the bipolar cutter 18 can securely be removed. As a result, without obstructing the view field of the rigid endoscope 4 during the manual operation, the manual operation can be continued without being discontinued.

FIGS. 44A to 44C show the constitution for scraping off the foreign materials sticking to the holder 21 in addition to the constitution of FIG. 43.

As shown, for one side portion of the sheath main unit 10 of the treatment sheath 2, in the same manner as in the constitution of FIG. 43 (the same clearance constitution as that in the above-described embodiment may also be used . . . see FIG. 9C), the cutter containing portion 38 for containing the bipolar cutter 18 is disposed, and a holder containing portion 35 for containing the blood vessel holder 21 is disposed in the other side portion. A slide friction portion 35a having a small clearance from the blood vessel holder 21 is disposed in the holder containing portion 35.

In general, the blood vessel holder 21 is pressed onto the blood vessel 61, the holder is swung vertically and horizontally, and the blood vessel holder 21 is used to strip the side branch 72 from the subcutaneous fat 73. Then, the foreign materials 81 such as blood, mucosa, and subcutaneous fat 73 stick to the blood vessel holder 21, and the foreign materials 81 sometimes obstruct the view field of the rigid endoscope 4. In this case, in the present constitution, the blood vessel holder 21 is moved backwards by the blood vessel holder 21 so as to draw the holder into the holder containing portion 35 of the sheath main unit 10. Then, because of a slight clearance between the blood vessel holder 21 and holder containing portion 35, the blood vessel holder 21 is in the slide contact with the slide friction portion 35a, and the foreign materials 81 such as the mucosa and subcutaneous fat 73 sticking to the blood vessel holder 21 can be scraped off by the front end surface of the sheath main unit 10.

As described above, according to the present constitution, since the foreign materials 81 sticking to the blood vessel holder 21 can easily be scraped off, and the view field of the rigid endoscope 4 during the manual operation is not obstructed, the manual operation can be continued without being interrupted.

FIGS. 46A to 60 show a second embodiment of the present invention. It is to be noted that in the present embodiment, the parts common to those of the first embodiment are denoted with the same reference numerals hereinafter and the description thereof is omitted.

As shown in FIGS. 46A to 48C, in the present embodiment, a holding rod 113 described alter of the blood vessel holder 21 fixed onto the sheath main unit 10 is inserted through the second treatment device channel 15 so that the bar can move forwards/backwards in the axial direction. Moreover, the holder operation portion 22 which can slide in the axial direction in the range of the elongate hole 17a of the second slide operation portion 17 is disposed on the proximal end of the holding rod 113.

Figure 49:
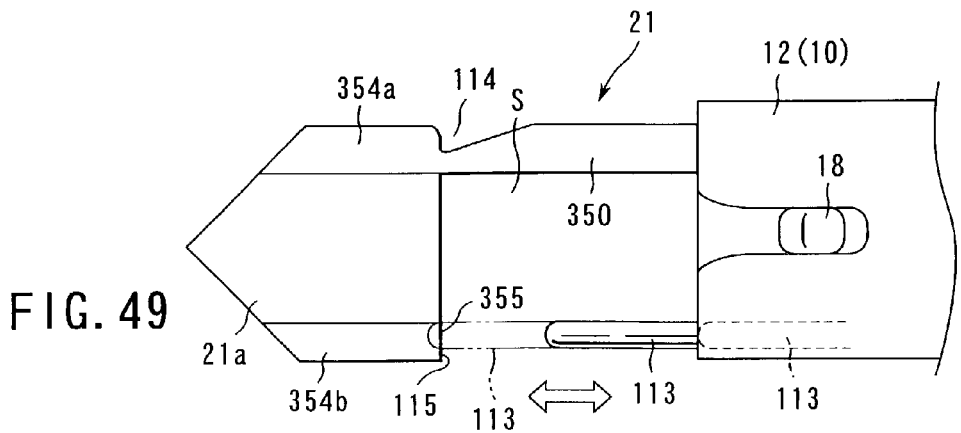
FIG. 49 is a plan view of the blood vessel holder.
Figure 50A:
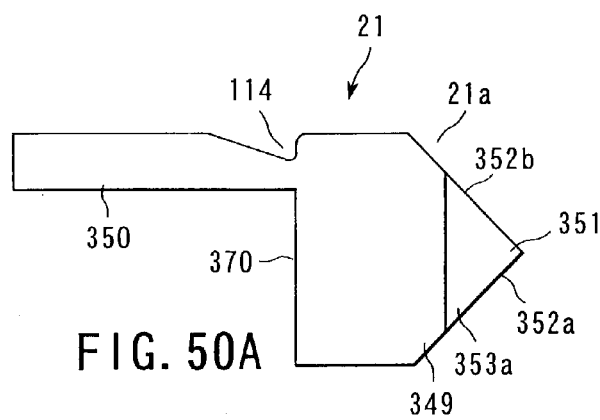
FIG. 50A is a lower surface view of the blood vessel holder of FIG. 49.
Figure 50B:
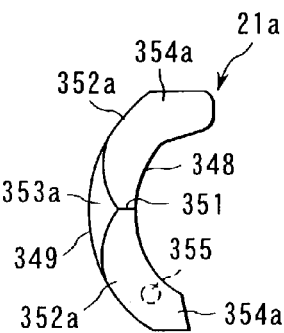
FIG. 50B is a front view of the blood vessel holder.
Figure 50C:
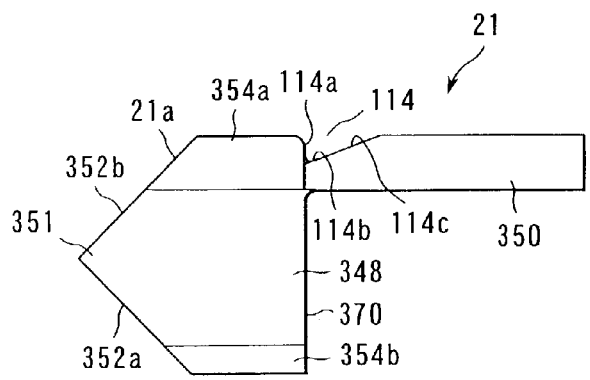
FIG. 50C is a top plan view of the blood vessel holder.
Figure 50D:
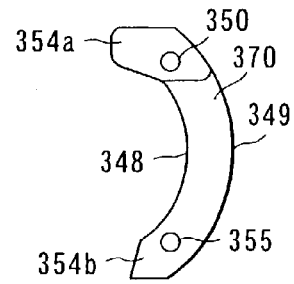
FIG. 50D is a rear view of the blood vessel holder.

As shown in FIG. 49, the blood vessel holder 21 includes: one shaft portion 350 fixed to the sheath main unit 10; the main unit 21a, disposed in the tip end of the shaft portion 350, for holding the harvesting object blood vessel 61; and the holding rod 113 which moves forwards/backwards in the second treatment device channel 15 of the sheath main unit 10 of the treatment sheath 2. In this case, the shaft portion 350 and holding rod 113 form a substantially symmetric positional relation with respect to the center axis and extend substantially in parallel to each other.

As shown in detail in FIGS. 50A to 50D, the main unit 21a made of synthetic resin and shaped like a pentagon as seen from above. A hook portion 370 is provided on the rear side of the main unit 21a. An upper surface 348 of the main unit 21a is formed as a arc concave surface which steadily holds the blood vessel to be harvested 61 from below (on which the blood vessel to be harvested 61 is steadily laid). Support walls 354a, 354b are formed on opposite sides of the upper surface 348 to hold the blood vessel to be harvested 61 laid on the upper surface 348 from the opposite sides. Among these support walls, one first support wall 354a is connected to the shaft portion 350. Moreover, the other second support wall 354b is formed opposite to the holding rod 113 which moves forwards/backwards, and includes an engagement hole 355 with which the tip end of the holding rod 113 is disengageably engaged.

A hook groove 114 is cut in a connecting portion of the shaft portion 350 and first support wall 354a on a side opposite to the upper surface 348 (on the opposite side of the upper surface 348 via the shaft portion 350). The hook groove 114 is shaped to hold a blood vessel (the side branch 72 described later in the present embodiment). For example, in the present embodiment, the hook portion is formed in a notch shape including a arc concave surface 114b which has substantially the same curvature radius as the outer diameter of the side branch 72 or a slightly larger curvature radius, a rear end surface 114a of the support wall 354a, and a taper surface 114c formed in the shaft portion 50.

The tip end of the main unit 21a is an acute-angle tip portion 351. The main unit 21a has first left and right taper surfaces 352a and 352b. The surfaces 352a and 352b are symmetrical to each other and continue to the tip portion 351. That is, the tip 37 of the main unit 21a is tapered at an acute angle. The lower surface of the tip portion 351 includes an inclined surface 353a. The inclined surface 353a is inclined, rising toward the tip of the tip portion 351. (The portion 351 gradually narrows from the lower end to the upper end.) Note that a lower surface 349 of the main unit 21a is formed as the arc concave surface along the shape of the upper surface 348. The tip of the main unit 21a being so shaped, the treatment sheath 2 can be smoothly inserted into a body cavity, without contacting the side branch 72 or the blood vessel 61.

As shown in FIG. 49, the main unit 21a of the blood vessel holder 21 and the shaft portion 350 cooperate with the tip end (tip-end cover 12) of the sheath main unit 10 of the treatment sheath 2 to form a concave space S for taking in the harvesting object blood vessel 61. This space S is opened/closed by the holding rod 113 which moves forwards/backwards in the second treatment device channel 15 of the sheath main unit 10. That is, the holding rod 113 is positioned in an opened position shown by a broken line, in which the tip end of the rod is sunk in the second treatment device channel 15, then the space S is completely opened, and this allows the blood vessel 61 to be drawn into the space S. On the other hand, the holding rod 113 is positioned in a closed position shown by a one-dot chain line, in which the tip end is engaged with the engagement hole 355 of the second support wall 354b of the main unit 21a, then the space S is completely closed, and the blood vessel 61 taken into the space S is held and securely captured. It is to be noted that the holding rod 113 is positioned in the closed position and engaged with the engagement hole 355, and then a stepped portion 115 having the function similar to that of the hook groove 114 is provided between the second support wall 354b and holding rod 113.

Figure 51:
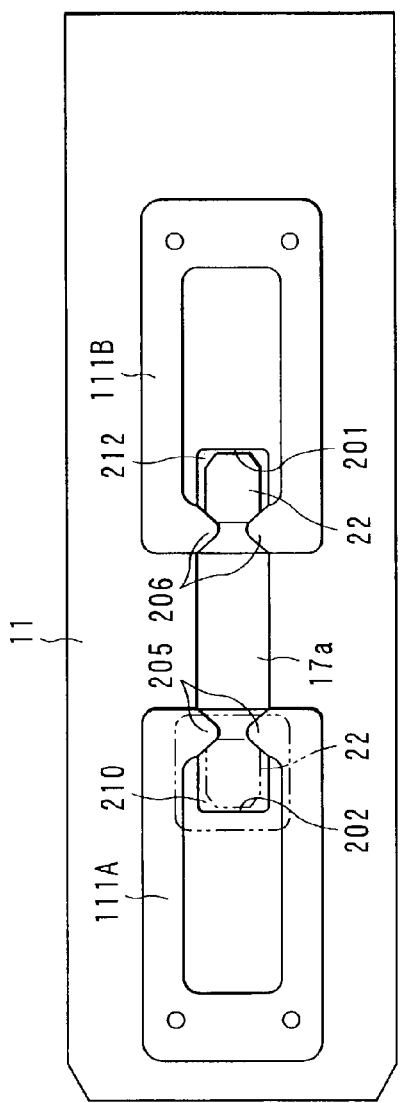
FIG. 51 is a view in a direction of arrow 51 of FIG. 46A.

In the present embodiment, a fixing mechanism is disposed to fix the holding rod 113 in the opened and closed positions. One example of this fixing mechanism is shown in FIG. 51 (view of FIG. 46A in the direction of the arrow 51). As shown, the fixing mechanism includes a pair of leaf springs 111A, 111B having forceps shapes disposed on opposite ends in the longitudinal direction of the elongate hole 17a of the second slide operation portion 17 in the operation portion cover 11 of the treatment sheath 2. In this case, the front-side leaf spring 111A defines the closed position of the holding rod 113, and includes a pair of claw portions 205, 205 projecting on opposite sides in the elongate hole 17a. Moreover, these claw portions 205, 205 form a first engagement space 210 which clicks/engages the holder operation portion 22 of the holding rod 113 between the portions and a front end surface 202 of the elongate hole 17a. Moreover, similarly, the rear-side leaf spring 111B defines the opened position of the holding rod 113, and includes a pair of claw portions 206, 206 projecting on the opposite sides in the elongate hole 17a. Moreover, these claw portions 206, 206 form a second engagement space 212 which clicks/engages the holder operation portion 22 of the holding rod 113 between the portions and a rear end surface 201 of the elongate hole 17a. That is, in the present embodiment, when the holder operation portion 22 is positioned (click-engaged) in the first engagement space 210, the space S for capturing the blood vessel is closed. When the holder operation portion 22 is positioned (click-engaged) in the second engagement space 212, the space S for capturing the blood vessel is opened.

Figure 53:
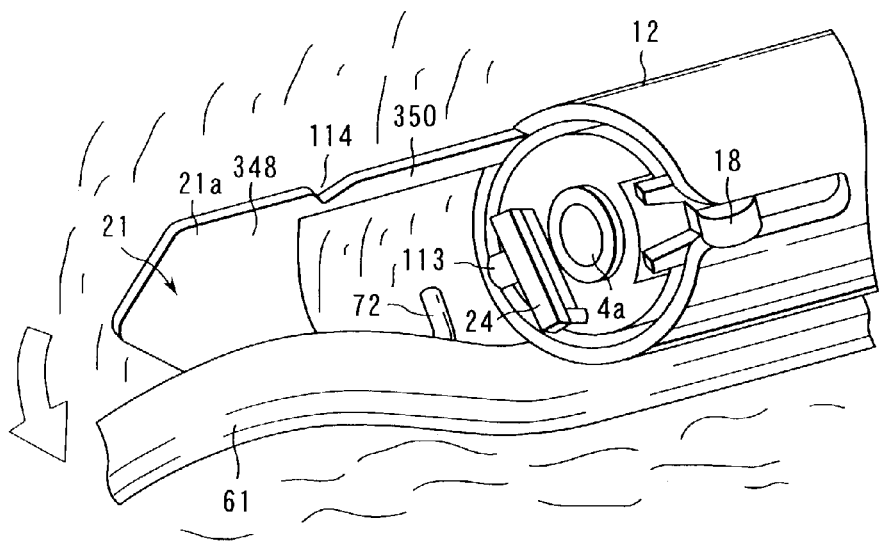
FIG. 53 is a perspective view showing a state in which a blood vessel is held by the blood vessel holder.
Figure 54:
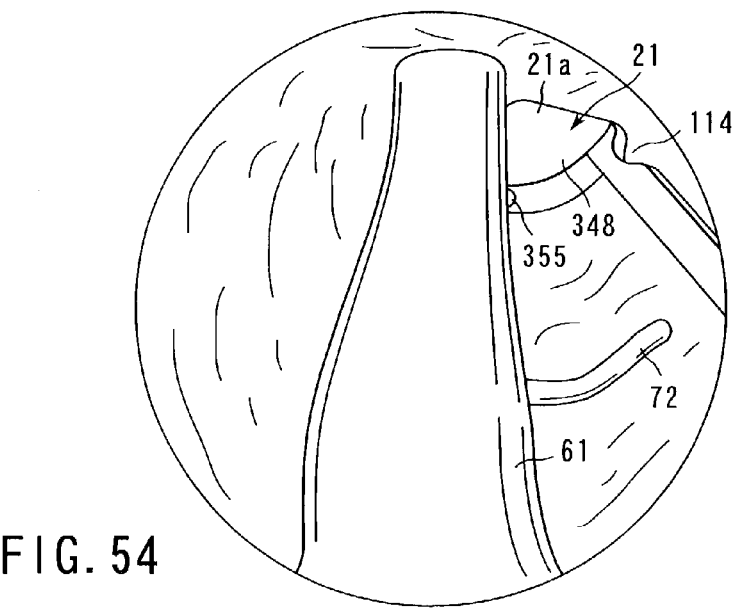
FIG. 54 is a view showing a monitor image of FIG. 53.

In this constitution, the blood vessel harvesting operation is performed by the following method. That is, first the dissector 3 is used to complete the stripping operation in the same manner as in the first embodiment. Subsequently, the treatment sheath 2 is inserted into the body cavity inflated with the air applied into it. The sheath 2 is inserted until its tip portion 351 reaches the that end of the scraped blood vessel 61 which lies at the inguinal portion 63. As shown in FIG. 53, the blood vessel holder 21 is rotated, together with the treatment sheath 2, in the end of the stripped blood vessel 61 on an inguinal portion 63 side. The main unit 21a is slipped under the blood vessel 61 so as to scoop up the blood vessel 61 from below by the main unit 21a. At this time, the holding rod 113 is of course held in an open position in which the tip end is sunk in the second treatment device channel 15 (the holder operation portion 22 is click-engaged in the second engagement space 212). FIG. 54 shows an observed image by the rigid endoscope 4 at this time, that is, a displayed image by the monitor 76.

Figure 52:
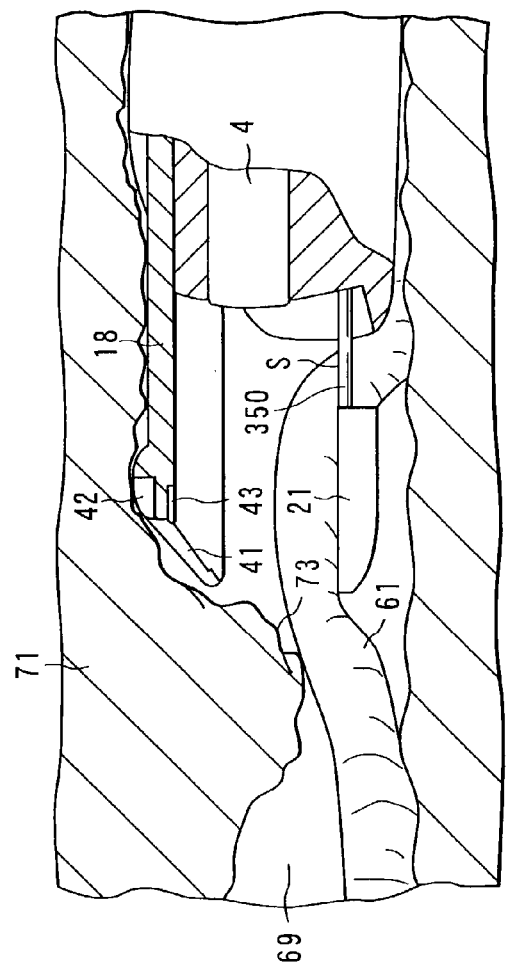
FIG. 52 is a sectional view of a state in which the treatment sheath is inserted in the body.
Figure 55:
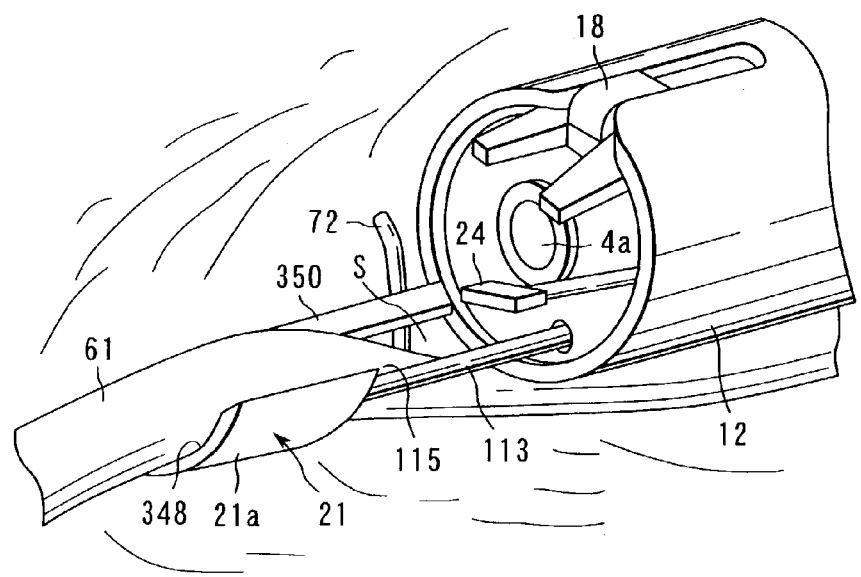
FIG. 55 is a perspective view showing a state in which a space for capturing the blood vessel is closed.
Figure 56:
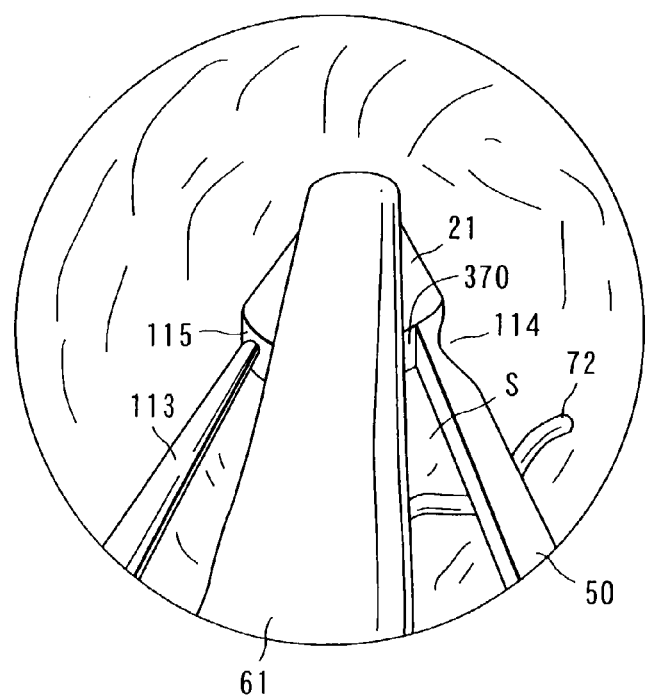
FIG. 56 is a view showing the monitor image of FIG. 55.

As shown in FIG. 52, the blood vessel 61 scooped up by the main unit 21a in this manner is laid on the upper surface 48 of the main unit 21a, and taken into a concave space S formed by the main unit 21a and shaft 350 of the blood vessel holder 21 and the tip end of the sheath main unit 10 of the treatment sheath 2. Subsequently, while the blood vessel 61 is taken into a space S, the holder operation portion 22 is moved forward, the holding rod 113 is projected from the tip end of the sheath main unit 10, and the tip end of the holding rod 113 is engaged in an engagement hole 355 of the main unit 21a (at this time, the holder operation portion 22 is click-engaged (stopped) in the first engagement space 210). Thereby, the space S is completely closed, and the blood vessel 61 taken into the space S is held from opposite sides by the holding rod 113 and shaft 350 and securely captured. This state is shown in FIGS. 55 and 56 (FIG. 56 shows the image displayed in the monitor 76 and observed by the rigid endoscope 4). As shown when the space S is completely closed, the stepped portion 115 is formed between the second support wall 354b and holding rod 113. That is, when the space S is closed by the holding rod 113, two hook grooves 114, 115 are formed disposed opposite to each other via the center axis of the rigid endoscope 4 on the opposite sides of the blood vessel holder 21.

After the blood vessel 61 is captured in the space S in this manner, the treatment sheath 2 is returned toward the cut skin portion 64 of the knee 62 on the hand side. At this time, the blood vessel holder 21 which has captured the blood vessel 61 is also returned together with the treatment sheath 2 along the blood vessel 61 under the blood vessel 61. In this case, the blood vessel holder 21, on whose upper surface 348 the blood vessel 61 is laid, can smoothly move forwards/backwards, because the upper surface 348 of the main unit 21a is formed in the arc concave surface. Moreover, the blood vessel 61 is prevented from being damaged.

When the blood vessel holder 21 is returned toward the hand side as described above, the hook groove 114 of the blood vessel holder 21 completely captures the blood vessel 61 from the opposite sides by the shaft 350 and holding rod 113. The holder 21 therefore reliably abuts on all the side branches 72 that extends from the blood vessel 61. That is, the blood vessel holder 21 is returned to the hand side. The side branch 72 is therefore be found. Then, the side branch 72 is cut with the bipolar cutter 18. At this time, the following operations are performed.

Figure 57:
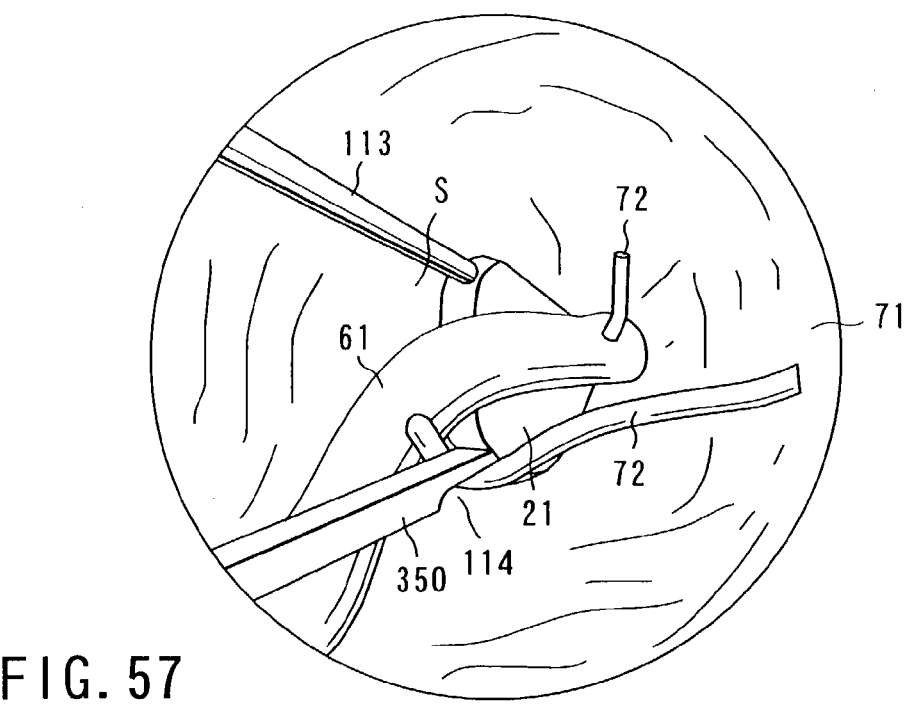
FIG. 57 shows the monitor image in which the blood vessel holder is rotated in one direction and tension is applied to a side branch.

For example, as shown in FIG. 57, when the hook portion 116 of the blood vessel holder 21 abuts on the side branch 72 positioned on the side of the shaft 350, the blood vessel holder 21 is rotated together with the treatment sheath 2 (twisted up) in a direction for pulling the side branch 72 with respect to the connective tissue on the blood vessel 71 (clockwise direction seen on the hand side in FIG. 57), and the tension is applied to the side branch 72. At this time, since the side branch 72 is caught and stably held by the hook groove 114 formed on the shaft 350 side, the tension is securely added to the side branch 72 simply by twisting up the blood vessel holder 21. Moreover, at this time, since the blood vessel 61 in the space S is held from the side by the shaft 350, the blood vessel does not come off from the space S with the twisting-up of the blood vessel holder 21. In addition, the side branch 72, which is placed in the hook groove 114, can be held firmly. A tension is applied to the side branch 72 as shown in FIG. 57, moving forward the bipolar cutter 18 now opposing the side branch 72. The bipolar cutter 18 cuts the side branch 72, as is illustrated in FIG. 58.

On the other hand, when the hook portion 370 of the blood vessel holder 21 abuts on the side branch 72 positioned on the side of the holding rod 113, the blood vessel holder 21 is rotated (twisted up) together with the treatment sheath 2 in a direction for pulling the side branch 72 with respect to the connective tissue on the blood vessel 71 (counterclockwise direction as seen on the hand side), and the tension is applied to the side branch 72. At this time, the side branch 72 is caught and stably held by the stepped portion 115 formed between the holding rod 113 and second support wall 354b. Therefore, when the blood vessel holder 21 is simply twisted up, the tension is securely applied to the side branch 72. Moreover, at this time, since the blood vessel 61 in the space S is supported from the side by the holding rod 113, the blood vessel does not come off from the space S with the twisting-up of the blood vessel holder 21. Furthermore, when the tension is applied to the side branch 72, the bipolar cutter 18 already positioned opposite to the side branch 72 is moved forwards, and the side branch 72 is cut by the bipolar cutter 18. This state is shown in FIG. 59.

Figure 58:
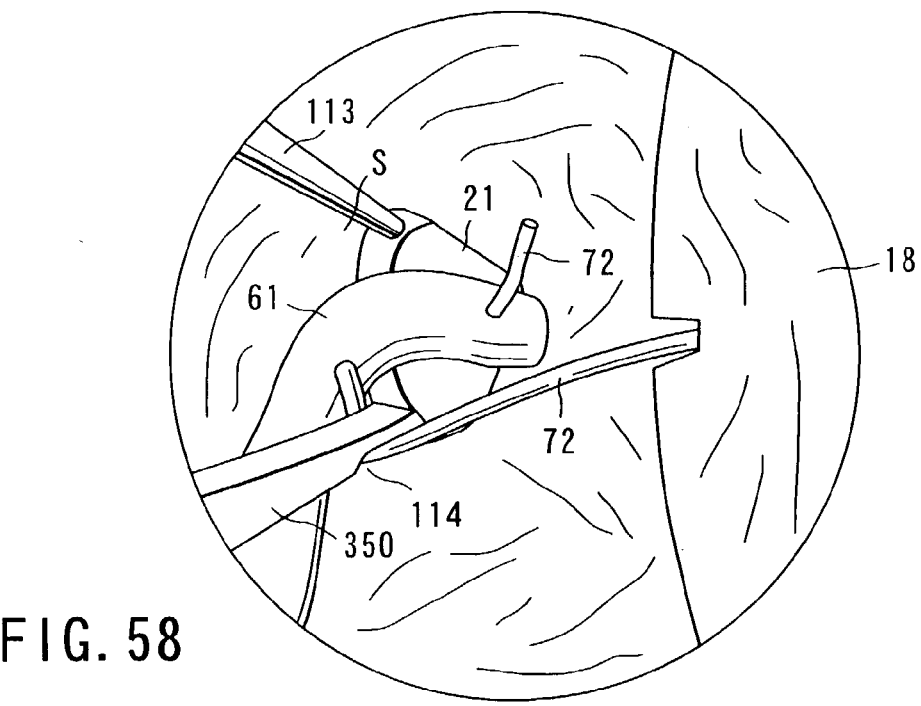
FIG. 58 shows the monitor image in which the side branch is cut by the bipolar cutter in the state of FIG. 57.
Figure 59:
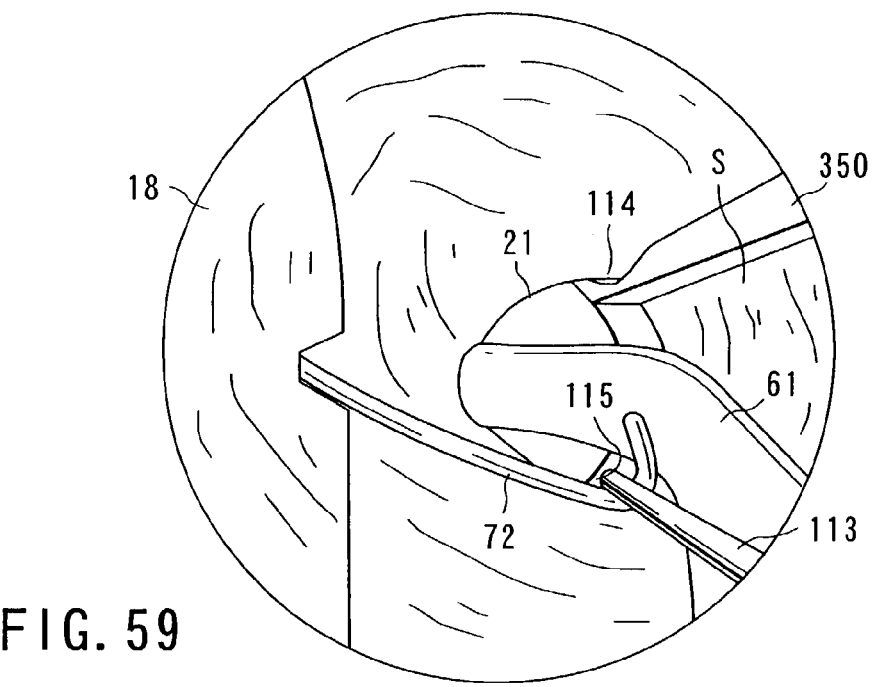
FIG. 59 shows the monitor image in which the blood vessel holder is rotated in a direction opposite to that of FIG. 57 and tension is applied to the side branch.

In the cases shown in FIGS. 58 and 59, to move forwards the bipolar cutter 18 to cut the side branch 72, the hook groove 114 and stepped portion 115 of the hook portion 370 hold the side branch 72 from a direction opposite to the advancing direction of the bipolar cutter 18. Therefore, the side branch 72 is pushed forwards by the bipolar cutter 18 and does not escape groove 114.

Figure 60:
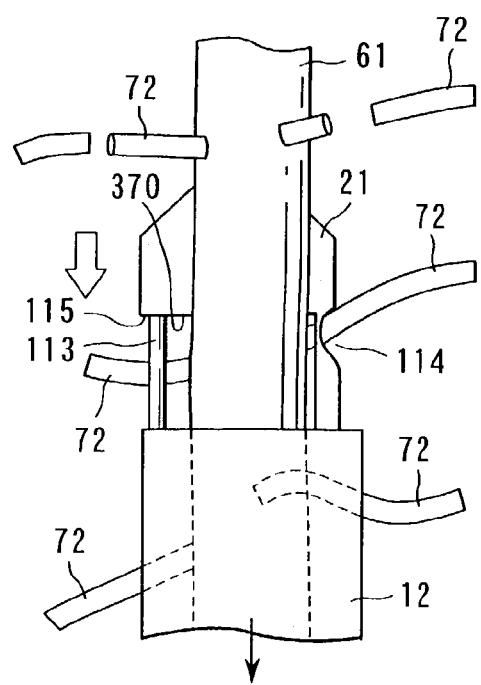
FIG. 60 is a plan view showing that the side branch is continuously treated.

Every time the blood vessel holder 21 abuts on the side branch 72, that is, every time a side branch 72 is found, the above-described operation is repeated (see FIG. 60). The blood vessel holder 21 is then returned to the cut skin portion 64. Thus, the side branch 72 on the blood vessel 61 can be cut and the blood vessel 61 can completely be separated from the living body.

As described above, the living tissue harvesting apparatus of the present embodiment includes: the treatment sheath 2 which can be inserted in the cavity through the cut skin portion; the rigid endoscope 4 as the endoscope inserted through the sheath 2; the bipolar cutter 18 as the cutting device which is disposed integrally with the sheath 2 and which can cut the living tissue; and the blood vessel holder 21 which is disposed integrally in the sheath 2 in order to hold the blood vessel 61 as the harvesting object tissue in the cavity. The blood vessel holder 21 includes the space S for taking in the blood vessel 61, and the holding rod 113 as a capturing member which openably closes the space S and captures the blood vessel 61 in the space S. Particularly in the present embodiment, the blood vessel holder 21 includes the main unit 21a which has the holding surface (upper surface) 348 which holds the blood vessel 61 before the sheath 2, and the space S is formed between the main unit 21a and sheath 2.

When the blood vessel 61 is taken into the space S formed by the holder 21 and can be captured in this manner, the holder 21 (sheath 2) is simply moved backwards, and the side branch 72 to be cut can be found. That is, instead of finding the side branches 72 one by one and treating these branches individually, an operation of moving forwards/backwards and rotating the holder 21 (sheath 2) in one direction along the blood vessel 61 is simply repeated, so that all the side branches 72 extending in various directions from the blood vessel 61 can securely be captured and can continuously be cut (like an assembly-line operation). Therefore, as compared with the related art, the time of the harvesting treatment can largely be shortened.

As FIG. 61 shows, the engagement hole 355A has a tapered rim 356A. The tapered rim 356A allows for displacement of the holding rod 113 with respect to the engagement hole 355A. FIG. 62 depicts a holding rod 113 that has a spherical distal end.

In the present embodiment, the opened and closed positions in the holding rod 113 are fixed by the click mechanism on the hand side, but the shape of the engagement hole 355 on the main unit 21a side of the blood vessel holder 21 may also be devised so as to fix at least the closed position of the holding rod 113. For example, as shown in FIG. 61, an engagement hole 355A which has an inner diameter smaller than the outer diameter of the holding rod 113 and in which the tip end of the holding rod 113 is elastically engaged may also be disposed in the main unit 21a. Alternatively, as shown in FIG. 62, an engagement hole 355B which has a spherical surface engaged with a spherical portion 113a formed in the tip end of the holding rod 113 may also be disposed in the main unit 21a. According to these structures, the holding rod 113 can securely be held in the closed position.

FIGS. 63A and 63B show another constitution for fixing the closed position of the holding rod 113. As shown in FIG. 63A, in this constitution, a head portion 113b and neck portion 113c are formed in the tip end of the holding rod 113. On the other hand, an engagement hole 355C disposed in the main unit 21a includes an engagement portion 220 with which the head portion 113b is engaged, and an annular protrusion 222 which is engaged with the neck portion 113c. Therefore, when the tip end of the holding rod 113 is pushed into the engagement hole 355C, as shown in FIG. 63B, the head portion 113b is engaged with the engagement portion 220, and the protrusion 222 is engaged with the neck portion 113c.

FIGS. 64A and 64B show further constitution for fixing the closed position of the holding rod 113. As shown in FIG. 64A, in this constitution, a bent portion 113d directed into the space S is formed on the tip end of the holding rod 113, and a groove-shaped engagement hole 355D is formed by cutting the outer wall of the second support wall 354b along the shape of the bent portion 113d in the main unit 21a. Therefore, when the tip end of the holding rod 113 is pushed into the engagement hole 355D, the bent portion 113d of the holding rod 113 is elastically deformed outwards from the space S, and engaged with and held by the engagement hole 355D.

FIG. 65 shows a first modification example of the blood vessel holder 21 according to the second embodiment. In this modification example, the shaft portion 350 moves forwards/backwards with respect to the sheath main unit 10, and the holding rod 113 is fixed to the sheath main unit 10. It is to be noted that other constitutions are the same as those of the above-described embodiment, and are therefore denoted with the same reference numerals and the description thereof is omitted.

Even with the structure, since the space S can openably be closed, the function/effect similar to that of the above-described embodiment can be obtained.

FIGS. 66A and 66B show a second modification example of the blood vessel holder 21. The main unit 21a of the blood vessel holder 21 according to this modification example is formed by tip-end holding members 230, 232 of a pair of elastic holding rods 116 which move forwards/backwards in the sheath main unit 10. In this case, the tip-end holding members 230, 232 have a symmetric configuration with respect to the center axis of the sheath main unit 10. Moreover, the respective holding rods 116 are symmetrically positioned with respect to the center axis of the sheath main unit 10. Furthermore, a habit (bending habit) of bending outwards in a diametric direction of the sheath main unit 10 is imparted to the tip end of each elastic holding rod 116 (see FIG. 66B). When the tip ends of the respective elastic holding rods 116 project from the sheath main unit 10 in FIG. 66B, the space S for capturing the blood vessel formed between the elastic holding rods 116 is opened.

When the respective holding rods 116 are drawn into the sheath main unit 10, the respective elastic holding rods 116 can forcedly be returned inwards linearly in the diametric direction of the sheath main unit 10, and the tip-end holding members 230, 232 of the respective holding rods 116 can abut on each other to close the space S for capturing the blood vessel formed by the respective holding rods 116 (see FIG. 66A).

Since the space S can openably be closed even in this structure, the function/effect similar to that of the above-described embodiment can be obtained. Further, the holder 21 can be smoothly pulled from the trocar 1 even if the trocar used has a valve (not shown). This helps to enhance the efficiency of the manual operation.

FIGS. 67A to 68C show a third modification example of the blood vessel holder 21. As shown in FIGS. 67A and 67B, the blood vessel holder 21 according to this modification example includes: a pair of shaft portions 350 extending from the sheath main unit 10; support members 235, 236 disposed on the tip end of the respective shaft portions 350; and an opening/closing sheet flap 117 extended between the support members 235, 236 to form the main unit 21a together with the support members 235, 236. In this case, the support members 235, 236 cooperate with each other to form the concave upper surface 348 of the main unit 21a which holds the blood vessel 61, and the flap 117 is extended between the support members 235, 236 on the side of the upper surface 348.

A hook groove 114 is formed between the shaft portion 350 and support members 235, 236 in the same manner as in the above-described embodiment, and the space S for capturing the blood vessel is formed between the shaft portions 350. Moreover, the flap 117 is fixed only to one support member 235 (236). Furthermore, the support members 235, 236 has the symmetric configuration with respect to the center axis of the sheath main unit 10. Additionally, the shaft portions 350 are symmetrically positioned with respect to the center axis of the sheath main unit 10.

In this constitution, the space S is closed as shown in FIGS. 67A and 67B as long as the flap 117 is not forced to be opened. However, when the flap 117 is positioned on the blood vessel 61 as shown in FIG. 68A, and the flap 117 is pressed onto the blood vessel 61 as shown in FIG. 68B, the flap 117 opens upwards as shown in FIG. 68C, and the blood vessel 61 can be drawn into the space S as shown in FIG. 68D, and the flap 117 can be closed again.

Therefore, since the space S can openably be closed even by this constitution, the function/effect similar to that of the above-described embodiment can be obtained. Since the symmetric configuration is formed, the blood vessel holder 21 can be smoothly pulled from the trocar 1 even if the trocar has a valve or the like. This serves to enhance the efficiency of the manual operation.

FIGS. 69A to 72 show a fourth modification example of the blood vessel holder 21. As shown in FIGS. 69A and 69B, the blood vessel holder 21 according to the modification example includes: a pair of function rods 119a, 119b which extend from the sheath main unit 10 and can rotate; and holding members 241, 242 which are disposed in the tip ends of the respective function rods 119a, 119b and cooperate with each other to form the main unit 21a. In this case, the holding members 241, 242 have a symmetric configuration with respect to the center axis of the sheath main unit 10, and the respective function rods 119a, 119b are also symmetrically positioned with respect to the center axis of the sheath main unit 10.

Figure 72:
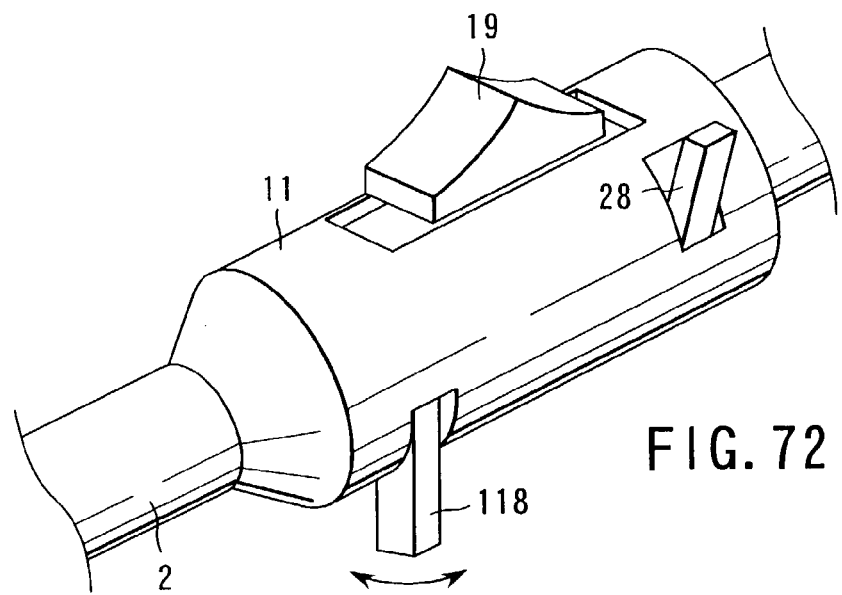
FIG. 72 is a perspective view of an operation portion cover in which the opening/closing mechanism of FIG. 71 is incorporated.
Figure 73:
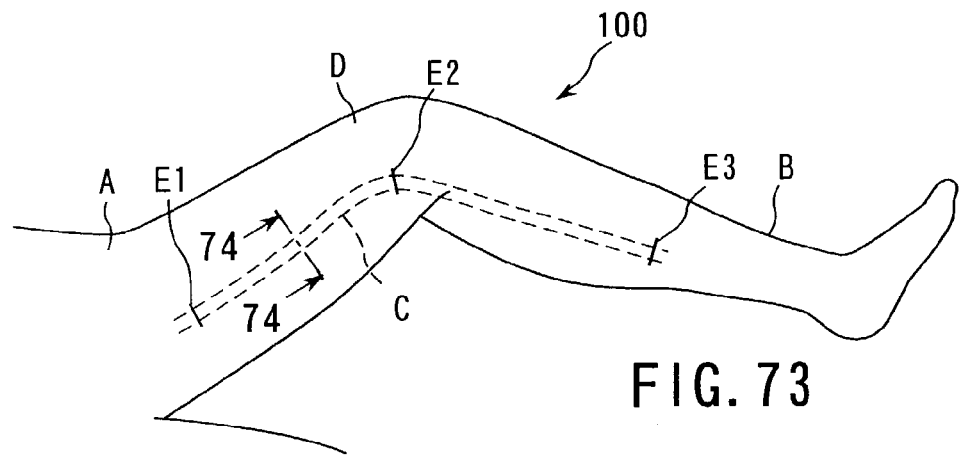
FIG. 73 is a diagram of a state in which the cut skin portion is formed in the leg.
Figure 74:
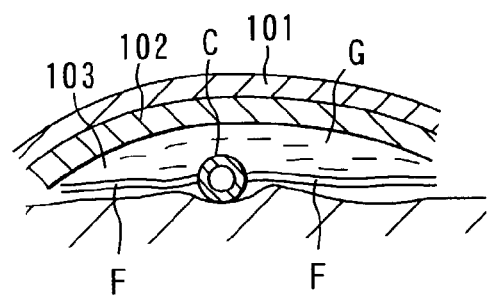
FIG. 74 is a sectional view along line 74—74 of FIG. 73.

As shown in FIG. 71, the first function rod 119a is supported by a bearing main unit 121 of the operation portion cover 11 so as to be rotatable, and fixed to an operation lever 118 rotatably disposed in the bearing main unit 121. Furthermore, a gear 120 is fixed to the first function rod 119a. Furthermore, the second function rod 119b is rotatably supported by the bearing main unit 121, and fixed to a gear 122. Additionally, the gears 120, 122 mesh with each other via two gears 121. It is to be noted that FIG. 72 shows an appearance view of the operation portion cover 11 in which the bearing main unit 121 and gears 120, 121, 122 are assembled.

Therefore, in this constitution, when the operation lever 118 is rotated on one side, the first function rod 119a rotates in the same direction as that of the operation lever 118, the second function rod 119b rotates in a direction opposite to that of the first function rod 119a via the gears 120, 121, 122, and the space S for capturing the blood vessel is opened as shown in FIGS. 70A and 70B. On the other hand, when the operation lever 118 is rotated on the other side, the function rods 119a, 119b similarly rotate, and the space S is closed as shown in FIGS. 69A and 69B.

With this constitution it is possible to close the space S can openably be closed. The function/effect similar to that of the above-described embodiment can be obtained and the symmetric configuration is formed. Hence, the holder 21 can be smoothly pulled from the trocar 1 even if the trocar has a valve or the like. This helps to increase the efficiency of the manual operation.

It is to be noted that, needless to say, the present invention is not limited to the above-described embodiments, and can variously be modified/carried out without departing from the scope. For example, in the above-described embodiments, the present invention is applied to the blood vessel harvesting apparatus, but the present invention can also be applied to the harvesting of living tissues other than the blood vessel. Moreover, in the above-described embodiment, the bipolar cutter is used as a high-frequency treatment device which cuts the side branch, but the monopolar cutter may also be used, and an ultrasonic treatment device or a mechanically cutting cutter may also be used.

What is claimed is:

1. A living tissue harvesting apparatus comprising:
    a sheath which is inserted in a body through a cut skin portion;
    an endoscope which is inserted through the sheath;
    a cutting device which is attached to the sheath so that the cutting device is moved in a longitudinal direction of the sheath by moving the sheath in the longitudinal direction together with the sheath, and movable in the longitudinal direction with respect to the sheath and which can cut a living tissue;
    an operation member for moving the cutting device in the longitudinal direction with respect to the sheath; and
    a holder which is attached to the sheath to be moveable with the sheath and to hold a harvesting object tissue in the body and which includes a press discharge portion to press-discharge the harvesting object tissue in a direction detached from the cutting device, the press discharge portion being movable in the longitudinal direction relative to the sheath;
    wherein the holder includes a hook portion to catch the living tissue in a position disposed opposite to the cutting device; and
    the cutting device and hook portion are movable with respect to each other.

2. The living tissue harvesting apparatus according to claim 1, wherein the holder includes a main unit which includes the press discharge portion, and a single shaft portion attached to the main unit which supports the main unit and moves the main unit in the longitudinal direction is attached to the main unit, and
    the shaft portion is attached to a position eccentric from the center axis of the main unit.

3. The living tissue harvesting apparatus according to claim 1, wherein the hook portion is formed in a taper shape which forms an acute angle and tapers.

4. The living tissue harvesting apparatus according to claim 1, wherein at least one portion of the holder is formed by a transparent material.

5. The living tissue harvesting apparatus according to claim 1, wherein the cutting device and/or holder is movable in the longitudinal direction with respect to the sheath, and
    the sheath includes a slide friction portion to slide on the cutting device or holder and to scrape off foreign materials sticking to the cutting device or holder, when the cutting device or holder is drawn into the sheath.

6. The living tissue harvesting apparatus according to claim 5, wherein a clearance into which a body tissue does not advance is formed between the tip end of the sheath and the cutting device or holder, and thereby the slide friction portion is formed.

7. The living tissue harvesting apparatus according to claim 1, wherein the cutting device has a cutter.

8. The living tissue harvesting apparatus according to claim 1, further comprising:
    an objective lens disposed at the endoscope; and
    a wiper which is disposed at a tip end of the sheath and which scrapes off foreign materials sticking to a surface of the objective lens of the endoscope.

9. The living tissue harvesting apparatus according to claim 1, wherein the holder includes a shaft portion which moves in the sheath in the longitudinal direction, and a main unit which is disposed at a tip end of the shaft portion to hold the harvesting object tissue, and the main unit includes a tip end formed in a taper shape which forms an acute angle and tapers.

10. The living tissue harvesting apparatus according to claim 1, wherein the hook portion has a holding surface having a C shape to hold the hooked tissue.

11. The living tissue harvesting apparatus according to claim 1, wherein the holder includes a space for taking in the harvesting object tissue, and a capturing member which openably closes the space and which captures the harvesting object tissue in the space.

12. The living tissue harvesting apparatus according to claim 11, wherein the holder includes a main unit which has a holding surface to hold the harvesting object tissue before the sheath, and the space is formed between the main unit and sheath.

13. The living tissue harvesting apparatus according to claim 11, further comprising hook grooves disposed on opposite sides of the space.

14. The living tissue harvesting apparatus according to claim 11, further comprising hook grooves disposed opposite to the opposite sides of the center axis of the endoscope.

15. The living tissue harvesting apparatus according to claim 1, wherein the cutting device cuts the living tissue by a high-frequency current.

16. The living tissue harvesting apparatus according to claim 11, wherein the capturing member is fixed in an opened position in which the capturing member opens the space and a closed position in which the capturing member closes the space.

17. The living tissue harvesting apparatus according to claim 16, wherein the opened and closed positions of the capturing member are fixed by a click mechanism.

18. The living tissue harvesting apparatus according to claim 1, wherein the holder forms a symmetric shape with respect to a center axis of the sheath.

19. A method for harvesting a subcutaneous living tissue, comprising:
    incising a skin on a harvesting object tissue to form a cut skin portion;
    inserting a stripping member in a body through the cut skin portion, and stripping the harvesting object tissue from a surrounding tissue by the stripping member;
    stripping the harvesting object tissue by the stripping member and inserting a sheath into the body through the cut skin portion, said sheath including a tissue cutting device, endoscope, and tissue holder having a space for holding a tissue;
    taking the stripped harvesting object tissue into a space by the holder under observation by the endoscope;
    capturing the harvesting object tissue taken into the space in the space by a capturing member which openably closes the space;
    moving the holder together with the sheath along the harvesting object tissue in a state in which the harvesting object tissue is captured in the space; and
    rotating the holder together with the sheath and applying a tension to a tissue not to be harvested, and cutting the tissue not to be harvested by the tissue cutting device, every time the holder abuts on the tissue not to be harvested extending from the harvesting object tissue.

20. An apparatus for harvesting a living tissue, comprising:
    a sheath which is inserted into a body through a cut skin portion;
    an endoscope which is inserted in the sheath;
    a cutting device movable into and from the sheath, for cutting living tissue, the cutting device being attached to the sheath so that the cutting device is moved in a longitudinal direction of the sheath by moving the sheath in the longitudinal direction, together with the sheath and movable in the longitudinal direction with respect to the sheath;

an operation member for moving the cutting device in the longitudinal direction with respect to the sheath; and tissue-catching means for catching and releasing a living tissue to be harvested.

21. An apparatus for harvesting a living tissue, comprising:

a sheath which is inserted into a body through a cut skin portion;

an endoscope which is inserted in the sheath;

a cutting device movable into and from the sheath, for cutting living tissue, the cutting device being attached to the sheath so that the cutting device is moved in a longitudinal direction of the sheath by moving the sheath in the longitudinal direction, and movable in the longitudinal direction with respect to the sheath an operation member for moving the cutting device in the longitudinal direction with respect to the sheath; and a holder for holding a tissue to be harvested and existing in the body, the holder having a space for holding the tissue and a capturing member for catching the tissue.

22. The apparatus according to claim 21, wherein the holder includes a main unit which has a holding surface to hold the harvesting object tissue before the sheath, and the space is formed between the main unit and sheath.

23. The apparatus according to claim 21, further comprising hook grooves are disposed on opposite sides of the space.

24. The apparatus according to claim 23, wherein the hook grooves are disposed opposite to the opposite sides of the center axis of the endoscope.

25. The apparatus according to claim 21, wherein the capturing member is fixed in an opened position in which the capturing member opens the space and a closed position in which the capturing member closes the space.

26. The apparatus according to claim 25, wherein the opened and closed positions of the capturing member are fixed by a click mechanism.

27. The apparatus according to claim 21, wherein the cutting device and the holder are movable relative to each other.

28. The apparatus according to claim 1, wherein the cutting device and the holder are movable in the sheath.

29. A living tissue harvesting apparatus comprising:

a sheath which can be inserted in a body through a cut skin portion;

an endoscope inserted through the sheath;

a cutting device which is disposed at sheath and which can cut a living tissue; and a holder which is disposed at the sheath to hold a harvesting object tissue in the body and which includes a press discharge portion to press-discharge the harvesting object tissue in a direction detached from the cutting device;

wherein the holder includes a hook portion to catch the living tissue in a position disposed opposite to the cutting device; and the cutting device and hook portion can move with respect to each other, and wherein the cutting device and/or holder can move forwards/backwards with respect to the sheath, and the sheath includes a slide friction portion to slide on the cutting device or holder and to scrape off foreign materials sticking to the cutting device or holder, when the cutting device or holder is drawn into the sheath.

30. A living tissue harvesting apparatus comprising:

a sheath which can be inserted in a body through a cut skin portion;

an endoscope inserted through the sheath;

a cutting device which is disposed at sheath and which can cut a living tissue; and a holder which is disposed at the sheath to hold a harvesting object tissue in the body and which includes a press discharge portion to press-discharge the harvesting object tissue in a direction detached from the cutting device;

wherein the holder includes a hook portion to catch the living tissue in a position disposed opposite to the cutting device; and the cutting device and hook portion can move with respect to each other, wherein the holder includes a space for taking in the harvesting object tissue, and a capturing member which openably closes the space and which captures the harvesting object tissue in the space.

* * * * *